(12) United States Patent
Stabach et al.

(10) Patent No.: US 12,344,868 B2
(45) Date of Patent: Jul. 1, 2025

(54) ENPP1 POLYPEPTIDES AND METHODS OF USING SAME

(71) Applicant: YALE UNIVERSITY, New Haven, CT (US)

(72) Inventors: Paul Stabach, Woodbridge, CT (US); Demetrios Braddock, Guilford, CT (US)

(73) Assignee: YALE UNIVERSITY, New Haven, CT (US)

( * ) Notice: Subject to any disclaimer, the term of this patent is extended or adjusted under 35 U.S.C. 154(b) by 908 days.

(21) Appl. No.: 17/271,018

(22) PCT Filed: Aug. 31, 2019

(86) PCT No.: PCT/US2019/049243
§ 371 (c)(1),
(2) Date: Feb. 24, 2021

(87) PCT Pub. No.: WO2020/047520
PCT Pub. Date: Mar. 5, 2020

(65) Prior Publication Data
US 2022/0119782 A1 Apr. 21, 2022

Related U.S. Application Data

(60) Provisional application No. 62/830,247, filed on Apr. 5, 2019, provisional application No. 62/725,607, filed on Aug. 31, 2018.

(51) Int. Cl.
*C12N 9/14* (2006.01)
*A61K 38/00* (2006.01)

(52) U.S. Cl.
CPC .............. *C12N 9/14* (2013.01); *A61K 38/00* (2013.01); *C07K 2319/02* (2013.01); *C07K 2319/30* (2013.01); *C12Y 306/01009* (2013.01)

(58) Field of Classification Search
CPC ...... C12N 9/14; A61K 38/00; C07K 2319/02; C07K 2319/30; C12Y 306/01009
See application file for complete search history.

(56) References Cited

U.S. PATENT DOCUMENTS

| | | | |
|---|---|---|---|
| 5,428,130 A | 6/1995 | Capon et al. | |
| 5,968,508 A | 10/1999 | Goldfine et al. | |
| 6,043,056 A | 3/2000 | Yue et al. | |
| 6,358,923 B1 | 3/2002 | Yue et al. | |
| 7,323,542 B2 | 1/2008 | Balian et al. | |
| 7,888,372 B2 | 2/2011 | Millan et al. | |
| 8,846,603 B2 | 9/2014 | Quinn et al. | |
| 9,744,219 B2 | 8/2017 | Braddock et al. | |
| 9,913,881 B2 | 3/2018 | Braddock et al. | |
| 10,064,917 B2 | 9/2018 | Braddock et al. | |
| 10,213,483 B2 | 2/2019 | Otterlei et al. | |
| 10,213,484 B2 | 2/2019 | Braddock et al. | |
| 10,493,135 B2 | 12/2019 | Braddock et al. | |
| 10,517,927 B2 | 12/2019 | Braddock et al. | |
| 10,583,170 B2 | 3/2020 | Braddock et al. | |
| 10,624,958 B2 | 4/2020 | Braddock et al. | |
| 2003/0190311 A1 | 10/2003 | Dall et al. | |
| 2007/0004913 A1 | 1/2007 | Challita-Eid et al. | |
| 2007/0015145 A1 | 1/2007 | Woolf et al. | |
| 2008/0273206 A1 | 11/2008 | Genge et al. | |
| 2010/0203076 A1 | 8/2010 | Fotin-Mleczek et al. | |
| 2014/0154774 A1 | 6/2014 | Quinn et al. | |
| 2014/0349369 A1 | 11/2014 | Buechler et al. | |
| 2014/0377859 A1 | 12/2014 | Quinn et al. | |
| 2015/0024460 A1 | 1/2015 | Quinn et al. | |
| 2015/0359858 A1 | 12/2015 | Braddock et al. | |
| 2016/0184387 A1 | 6/2016 | Charmot et al. | |
| 2016/0184458 A1 | 6/2016 | Heartlein | |
| 2017/0340713 A1 | 11/2017 | Braddock et al. | |
| 2017/0340714 A1* | 11/2017 | Braddock | A61P 13/12 |
| 2017/0354719 A1 | 12/2017 | Braddock et al. | |

FOREIGN PATENT DOCUMENTS

| | | |
|---|---|---|
| CN | 107109381 A | 8/2017 |
| EP | 3298140 A1 | 3/2018 |
| JP | 2005-501514 A | 1/2005 |
| JP | 2008188015 A | 8/2008 |
| JP | 2018-516566 A | 6/2018 |
| RU | 2013142583 A | 4/2015 |
| RU | 2016107788 A | 11/2018 |
| WO | 0239994 A2 | 5/2002 |
| WO | 02092020 A2 | 11/2002 |
| WO | 03040340 A2 | 5/2003 |

(Continued)

OTHER PUBLICATIONS

Genbank Accession No. XP _006144365.1, Retrieved from the Internet «https://www.ncbi.nlm.nih.gov/protein/XP_006144365.1?report=genbank&log$=protalign&blast_rank=92&RI D=X9E 1 SC3Z016», Retrieved on Feb. 20, 2024.
Dohler, et al. "Crystal structure and substrate binding mode of ectonucleotide phosphodiesterase/pyrophosphatase-3 (NPP3)." Scientific reports 8.1 (2018): 1-13.
Li, et al. "Serum phosphate concentration and incidence of stroke: a systemic review and meta-analysis." Neurological sciences 35.12 (2014): 1877-1882.
Kassim (Clinical Advances in Hematology & Oncology vol. 14, Issue May 5, 2016 pp. 307-309).
Extended European Search Report for European Patent Application No. 20783595.0 dated Jan. 2, 2023.
Nitschke, et al. "ENPP1-Fc prevents neointima formation in generalized arterial calcification of infancy through the generation of AMP." Experimental & Molecular Medicine 50.10 (2018): 1-12.
Albright, et al. "ENPP1-Fc prevents mortality and vascular calcifications in rodent model of generalized arterial calcification of infancy." Nature communications 6.1 (2015): 10006.

(Continued)

*Primary Examiner* — Mark Halvorson
*Assistant Examiner* — Dennis J Sullivan
(74) *Attorney, Agent, or Firm* — Saul Ewing, LLP; Kathryn Doyle; Domingos J. Silva

(57) ABSTRACT

The present invention includes ENPP1 polypeptides with improved in vivo half-lives. The invention further provides an ENPP1 polypeptide fusion comprising an ENPP1 polypeptide fused to a Fc region of an immunoglobulin, wherein the polypeptide fusion comprises at least one point mutation.

18 Claims, 21 Drawing Sheets

Specification includes a Sequence Listing.

(56) References Cited

FOREIGN PATENT DOCUMENTS

| | | | |
|---|---|---|---|
| WO | 2006135925 A2 | 12/2006 | |
| WO | 2008105911 A2 | 9/2008 | |
| WO | 2011113027 A2 | 9/2011 | |
| WO | 2012125182 A1 | 9/2012 | |
| WO | 2014126965 A2 | 8/2014 | |
| WO | 2016100803 A2 | 6/2016 | |
| WO | 2016187408 A1 | 11/2016 | |
| WO | 2017087936 A1 | 5/2017 | |
| WO | 2017191274 A2 | 11/2017 | |
| WO | 2018027024 A1 | 2/2018 | |
| WO | 2018/157165 A1 | 8/2018 | |
| WO | 2019217373 A1 | 11/2019 | |

OTHER PUBLICATIONS

Mackenzie, et al. "New insights into NPP1 function: lessons from clinical and animal studies." Bone 51.5 (2012): 961-968.

Nitschke, Y et al. "Generalized arterial calcification of infancy and pseudoxanthoma elasticum can be caused by mutations in either ENPP1 or ABCC6." The American Journal of Human Genetics 90.1 (2012): 25-39.

Nitschke, et al. "Generalized arterial calcification of infancy and pseudoxanthoma elasticum: two sides of the same coin." Frontiers in genetics 3 (2012): 302.

Rutsch, et al. "Genetics in arterial calcification: pieces of a puzzle and cogs in a wheel." Circulation research 109.5 (2011): 578-592.

Nitschke, et al. "Inherited arterial calcification syndromes: etiologies and treatment concepts." Current osteoporosis reports 15 (2017): 255-270.

European Supplemental Partial Search Report for European Patent Application No. 14751154.7 issued Nov. 7, 2016.

Extended European Search Report for European Patent Application No. 14751154.7 issued Feb. 16, 2017.

Extended European Search Report for European Patent Application No. 16797290.0 issued Jun. 25, 2019.

Extended European Search Report for European Patent Application No. 17837677.8 issued Mar. 24, 2020.

International Search Report and Written Opinion for PCT International Application No. PCT/US2017/045280 issued Dec. 26, 2017.

Mus musculus domesticus ecto-nucleotide pyrophosphatase/phosphodiesterase-1 mRNA, complete cds, GenBank J02700.2, Aug. 12, 2020 searched.

Notice of Panel Decision from Pre-Appeal Brief Review for U.S. Appl. No. 15/812,456 issued Dec. 2, 2020.

Notice of Reasons for Rejection for Japanese Patent Application No. 2017-560327 dated Mar. 30, 2020, 5 pages.

PCT International Search Report and Written Opinion for PCT International Application No. PCT/US2014/015945 issued Jul. 30, 2014.

PCT International Search Report and Written Opinion for PCT International Application No. PCT/US2016/033236 Issued Oct. 27, 2016.

Pre-Appeal Brief for U.S. Appl. No. 15/812,456, filed Oct. 16, 2020.

UniProt Accession No. O14638, ENPP3_Human, Jan. 7, 2015 [online]. [Retrieved on Jan. 19, 2017]. Retrieved from the internet <URL: http://www.uniprot.org/uniprot/O14638.txt?version=133>.

"Chronic Renal Failure: From the Perspective of Internal Medicine", Clinical Imagiology 21(11), 2005, 1142-1149 (Partial Translation).

"Pharmacokinetic Control of Biopharmaceuticals", Journal of Pharmaceutical Science and Technology, Japan, 2014, 27-32 (Partial Translation).

Albright, et al., "ENPP1-Fc prevents mortality and vascular calcifications in rodent model of generalized arterial calcification of infancy", Nat Commun. 6, 2015, 10006.

Albright, et al., "Molecular basis of purinergic signal metabolism by ectonucleotide pyrophosphatase/phosphodiesterases 4 and 1 and implications in stroke", J Biol Chem. 289(6), 2014, 3294-3306.

Albright, et al., "NPP4 is a procoagulant enzyme on the surface of vascular endothelium", Blood. 120(22), 2012, 4432-4440.

Anonymous, "UPI000511D809", Retrieved from the Internet Mar. 7, 2019, <https://www.uniprot.org/uniparc/UPI000 511D809>, Oct. 2014.

Belisário, et al., "Association between ENPP1 K173Q and stroke in a newborn cohort of 395 Brazilian children with sickle cell anemia", Blood. 126(10), 2015, 1259-1260.

Buckley, et al., "Plasma cell membrane glycoprotein PC-1. cDNA cloning of the human molecule, amino acid sequence, and chromosomal location", J Biol Chem. 265(29), Oct. 1990, 17506-17511.

Caballero, et al., "Impaired urinary osteopontin excretion in Npt2a-/-mice", Am J Physiol Renal Physiol. 312(1), 2017, F77-F83.

Calvert, et al., "The Provisional Patent Application: What You Need to Know", Inventors Eye. United States Patent and Trademark Office, Apr. 2010, 5 pages.

Cimpean, et al., "Substrate-specifying determinants of the nucleotide pyrophosphatases/phosphodiesterases NPP1 and NPP2", Biochem J. 381(Pt 1), 2004, 71-77.

Dasgupta, et al., "Mutations in SLC34A3/NPT2c are associated with kidney stones and nephrocalcinosis", J Am Soc Nephrol. 25(10), 2014, 2366-2375.

Eller, et al., "Impact of ENPP1 genotype on arterial calcification in patients with end-stage renal failure", Nephrol Dial Transplant. 23(1), 2008, 321-327.

Flanagan, et al., "Genetic mapping and exome sequencing identify 2 mutations associated with stroke protection in pediatric patients with sickle cell anemia", Blood. 121(16), 2013, 3237-3245.

Fleisch, et al., "Inhibitors and promoters of stone formation", Kidney Int. 13(5), 1978, 361-371.

Gijsbers, et al., "Functional characterization of the non-catalytic ectodomains of the nucleotide pyrophosphatase/phosphodiesterase NPP1", Biochem J. 371(Pt 2), Apr. 15, 2003, 321-330.

Goding, et al., "Physiological and pathophysiological functions of the ecto-nucleotide pyrophosphatase/phosphodiesterase family", Biochim Biophys Acta. 1638(1), 2003, 1-19.

Guo, et al., "Clinical outcomes of various continued antiplatelet therapies in patients who were administered DAPT following the implantation of drug-eluting stents and developed gastrointestinal hemorrhage", Exp Ther Med. 12(2), Aug. 2016, 1125-1129.

Jansen, et al., "ABCC6 prevents ectopic mineralization seen in pseudoxanthoma elasticum by inducing cellular nucleotide release", Proc Natl Acad Sci U S A. 110(50), 2013, 20206-20211.

Jansen, et al., "ABCC6-mediated ATP secretion by the liver is the main source of the mineralization inhibitor inorganic pyrophosphate in the systemic circulation-brief report", Arterioscler Thromb Vasc Biol. 34(9), 2014, 1985-1989.

Jansen, et al., "Proteolytic maturation and activation of autotaxin (NPP2), a secreted metastasis-enhancing lysophospholipase D", J Cell Sci. 118(Pt 14), 2005, 3081-3089.

Jansen, et al., "Structure of NPP1, an ectonucleotide pyrophosphatase/phosphodiesterase involved in tissue calcification", Structure. 20(11), 2012, 1948-1959.

Jin-Hua, et al., "Molecular Coning and Chromosomal Localization of Pd-Iβ (PDNP3), a New Member of the Human Phosphodiesterase I Genes", Genomics 45, 1997, 412-415.

Johnson, et al., "Differential mechanisms of inorganic pyrophosphate production by plasma cell membrane glycoprotein-1 and B10 in chondrocytes", Arthritis Rheum. 42(9), 1999, 1986-1997.

Johnson, et al., "Kabat database and its applications: 30 years after the first variability plot", Nucleic Acids Res. 28 (1), Jan. 2000, 214-218.

Johnson, et al., "Linked deficiencies in extracellular PP(i) and osteopontin mediate pathologic calcification associated with defective PC-1 and ANK expression", J Bone Miner Res. 18(6), 2003, 994-1004.

Johnson, et al., "Matrix vesicle plasma cell membrane glycoprotein-1 regulates mineralization by murine osteoblastic MC3T3 cells", J Bone Miner Res. 14(6), Jun. 1999, 883-892.

Johnson, et al., "The Nucleoside Triphosphate Pyrophosphohydrolase Isozyme PC-1 Directly Promotes Cartilage Calcification Through Chondrocyte Apoptosis and Increased Calcium Precipitation by Mineralizing Vesicles", The Journal of Rheumatology 28 (12), Dec. 2001, 2681-2691.

(56) References Cited

OTHER PUBLICATIONS

Kato, et al., "Crystal structure of Enpp1, an extracellular glycoprotein involved in bone mineralization and insulin signaling", Proc Natl Acad Sci U S A. 109(42), Oct. 2012, 16876-16881.

Lee, et al., "Cloning, chromosomal localization, and tissue expression of autotaxin from human teratocarcinoma cells", Biochem Biophys Res Commun. 218(3, 1996, 714-719.

Li, et al., "Inhibition of Tissue-Nonspecific Alkaline Phosphatase Attenuates Ectopic Mineralization in the Abcc6 -/- Mouse Model of PXE but Not in the Enpp1 Mutant Mouse Models of GACI", J Invest Dermatol. 139(2), Feb. 2019, 360-368.

Li, et al., "Response of Npt2a knockout mice to dietary calcium and phosphorus", PLoS One. 12(4), 2017, e0176232.

Lieben, et al., "Normocalcemia is maintained in mice under conditions of calcium malabsorption by vitamin D-induced inhibition of bone mineralization", J Clin Invest. 122(5), 2012, 1803-1805.

Millán, et al., "Enzyme replacement therapy for murine hypophosphatasia", J Bone Miner Res. 23(6), Jun. 2008, 777-787.

Okawa, et al., "Mutation in Npps in a mouse model of ossification of the posterior longitudinal ligament of the spine", Nat Genet. 19(3), Jul. 1998, 271-273.

Ratkalkar, et al., "Mechanisms of Stone Formation", Clin Rev Bone Miner Metab. 9(3-4), 2011, 187-197.

Schetter, et al., "Nucleoporins NPP-1, NPP-3, NPP-4, NPP-11 and NPP-13 are required for proper spindle prientation in C. elegans", Dev Biol. 289(2), Jan. 15, 2006, 360-371.

Shankar, et al., "Progeria—A Brief Review", International Journal of Pharma and Bio Sciences 2, 2010, 1-14.

Zhang, et al., "The interaction of cationic polymers and their bisphosphonate derivatives with hydroxyapatite", Macromol Biosci. 7(5), May 10, 2007, 656-670 (Abstract Only).

Sheehan, et al., "Genetic modifiers of sickle cell anemia in the Baby Hug cohort: influence on laboratory and clinical phenotypes", Am J Hematol. 88(7), 2013, 571-576.

Silcox, et al., "Measurement of inorganic pyrophosphate in biological fluids. Elevated levels in some patients with osteoarthritis, pseudogout, acromegaly, and uremia", J Clin Invest. 52(8), Aug. 1973, 1863-1870.

Stefan, et al., "NPP-type ectophosphodiesterases: unity in diversity.", Trends Biochem Sci. 30(10), Oct. 2005, 542-550.

Terkeltaub, "Physiologic and pathologic functions of the NPP nucleotide pyrophosphatase/phosphodiesterase family focusing on NPP1 in calcification.", Purinergic Signal. 2(2), Jun. 2, 2006, 371-377.

Tsai, et al., "The Ectoenzyme E-NPP3 Negatively Regulates ATP-Dependent Chronic Allergic Responses by Basophils and Mast Cells", Immunity 42, Feb. 2015, 279-293.

Van Meeteren, et al., "Inhibition of autotaxin by lysophosphatidic acid and sphingosine 1-phosphate", J Biol Chem. 280(22), Jun. 2005, 21155-21161.

Whisstock, et al., "Prediction of proteinfunction fromprotein sequence and structure", Quarterly Reviews of Biophysics 36, 3 (2003), pp. 2003, 307-340.

Witkowski, et al., "Conversion of a Beta-Ketoacyl Synthase to a Malonyl Decarboxylase by Replacement of the Active-Site Cysteine With Glutamine", Biochemistry 38(36), Sep. 1999, 11643-11650.

Sayer "Progress in understanding the genetics of calcium-containing nephrolithiasis." Journal of the American Society of Nephrology 28.3 (2017): 748-759.

Robbie, et al. "A novel investigational Fc-modified humanized monoclonal antibody, motavizumab-YTE, has an extended half-life in healthy adults." Antimicrobial agents and chemotherapy 57.12 (2013): 6147-6153.

International Search Report and Written Opinion for PCT International Application No. PCT/US2019/049243 issued Jan. 21, 2020.

Supplementary European Search Report for European Patent Application No. 19855284.6 dated Apr. 21, 2022.

Yin, et al. "Glycoengineering of Chinese hamster ovary cells for enhanced erythropoietin N-glycan branching and sialylation." Biotechnology and bioengineering 112.11 (2015): 2343-2351.

Rath, et al. "Fc-fusion proteins and FcRn: structural insights for longer-lasting and more effective therapeutics." Critical reviews in biotechnology 35.2 (2015): 235-254.

Dall'Acqua, et al. "Increasing the affinity of a human IgG1 for the neonatal Fc receptor: biological consequences." The Journal of Immunology 169.9 (2002): 5171-5180.

\* cited by examiner

| 4 hr | 7 hr | 18 hr | 25.5 hr | 48 hr | 75 hr | 91 hr |
|---|---|---|---|---|---|---|
| 348 | 1,072 | 1,912 | 1,512 | 1,552 | 892 | 668 |
| 416 | 536 | 1,476 | 1,244 | 1,104 | 844 | 908 |
|  | 492 | 1,628 | 1,488 |  | 904 | 692 |
|  |  | 1,280 | 1,312 |  | 932 | 640 |
|  |  | 1,716 | 1,172 |  | 788 |  |

| Construct | Mutations | | | | | Sialyl Transferase | PK | Area Under Curve (AUC) |
|---|---|---|---|---|---|---|---|---|
| | Signal Sequence | Catalytic Domain | Nuclease Domain | Linker 2 | Fc Domain | | | |
| 770 | | | | | | | 34.2 | 3,027 |
| 930 | | K369N I317T | | | | | 35.4 | 2,545 |
| 951 | | | E592N | | | | 40 | 1,789 |
| 976 | C25N K27T | | | | | | 36.4 | 3,636 |
| 981 | | | | | M883Y S885T T887E | | 84 | 17,587 |
| 1014 | V29N | | E592N | | H1064K N1065F | | 99.9 | 21,752 |
| 1020 | C25N K27T | | | E864N L866T | | | 37 | 12,829 |
| 1024 | C25N K27T | | S766N | | | | 34.9 | 4,537 |
| 1028 | | | E592N | | M883Y S885T T887E | | 80.1 | 16,932 |
| 1030 | | | S766N | | M883Y S885T T887E | | 45.4 | 1,912 |
| 1040 | V29N | | P534N V536T | | M883Y S885T T887E | | 119.4 | 32,391 |
| 1047 | V29N | | | E864N L866T | | | 37.6 | 4,373 |
| 1048 | V29N | | | | H1064K N1065F | | 57.1 | 13,918 |
| 1051 | V29N | | | | H1064K N1065F | | 63.4 | 13,812 |

| Construct | Mutations | | | | | Sialyl Transferase | PK | Area Under Curve (AUC) |
|---|---|---|---|---|---|---|---|---|
| | Signal Sequenc | Catalytic Domain | Nuclease Domain | Linker 2 | Fc Domain | | | |
| 1057 | V29N | | S766N | | H1064K N1065F | | 64.6 | 5,826 |
| 1064 | C25N K27T | | S766N | | H1064K N1065F | | 50.6 | 7,540 |
| 1082 | V29N | | E592N | | M883Y S885T T887E | | 70 | 14,978 |
| 1014-ST | V29N | | E592N | | H1064K N1065F | Y | 96.2 | 13,883 |
| 1028-ST | | | E592N | | M883Y S885T T887E | Y | 100 | 25,500 |
| 1057-ST | V29N | | S766N | | H1064K N1065F | Y | 87.4 | 15,337 |
| 1057-ST-A | V29N | | S766N | | H1064K N1065F | Y | 124.9 | 23,867 |
| 1064-ST | C25N K27T | | S766N | | H1064K N1065F | Y | 70.1 | 20,062 |
| 1089 (trypsin KO) | V29N | | E592N R741D | | H1064K N1065F | | 76.4 | 19,835 |
| 770B | | | | | | | 36.4 | 3,647 |
| 930-ST | | K369N I317T | | | | Y | 36.3 | 4,407 |
| 951-ST | | | E592N | | | Y | 49.3 | 8,379 |
| 981-ST | | | | | M883Y S885T T887E | Y | 122.5 | 30,021 |

ENPP1 POLYPEPTIDES AND METHODS OF USING SAME

CROSS-REFERENCE TO RELATED APPLICATIONS

The present application is a 35 U.S.C. § 371 national phase application from, and claims priority to, International Application No. PCT/US2019/049243, filed Aug. 31, 2019, which claims priority under 35 U.S.C. § 119(e) to U.S. Provisional Patent Application No. 62/725,607, filed Aug. 31, 2018, and U.S. Provisional Patent Application No. 62/830,247, filed Apr. 5, 2019, all of which applications are hereby incorporated by reference in their entireties herein.

BACKGROUND OF THE INVENTION

The human ectonucleotide pyrophosphatase (ENPP) protein family comprises seven extracellular, glycosylated proteins (i.e., ENPP1-ENPP7) that hydrolyze phosphodiester bonds. ENPPs are cell-surface enzymes, with the exception of ENPP2, which is exported to the plasma membrane but is cleaved by furin and released into the extracellular fluid. The ENPP enzymes have high degrees of sequence and structural homology, but exhibit a diverse substrate specificity encompassing nucleotides to lipids.

ENPP1 (also known as PC-1) is a type 2 extracellular membrane-bound glycoprotein located on the mineral-depositing matrix vesicles of osteoblasts and chondrocytes, and hydrolyzes extracellular nucleotides (principally ATP) into adenosine monophosphate (AMP) and inorganic pyrophosphate (PPi). PPi functions as a potent inhibitor of ectopic tissue mineralization by binding to nascent hydroxyapatite (HA) crystals, thereby preventing the future growth of these crystals. ENPP1 generates PPi via hydrolysis of nucleotide triphosphates (NTPs), Progressive Ankylosis Protein (ANK) transports intracellular PPi into the extracellular space, and Tissue Non-specific Alkaline Phosphatase (TNAP) removes PPi via direct hydrolysis of PPi into Pi.

Ectopic tissue mineralization is associated with numerous human diseases, including chronic joint disease and acutely fatal neonatal syndromes. To prevent unwanted tissue calcification, factors that promote and inhibit tissue mineralization must be kept in tight balance. The balance of extracellular inorganic pyrophosphate (PPi) and phosphate (Pi) is an important regulator of ectopic tissue mineralization. The activity of the three extracellular enzymes—TNAP, ANK, and ENPP1—tightly control the concentration of Pi and PPi in mammals at 1-3 mM and 2-3 µM respectively. PPi is a regulator of biomineralization, inhibiting the formation of basic calcium phosphate from amorphous calcium phosphate.

ENPP1 polypeptides have been shown to be effective in treating certain diseases of ectopic tissue calcification. ENPP1-Fc has been shown to reduce generalized arterial calcifications in a mouse model for GACI (generalized arterial calcification of infants), which is a severe disease occurring in infants and involving extensive arterial calcification (Albright, et al., 2015, Nature Comm. 10006). Fusion proteins of ENPP1 have also been described to treat diseases of severe tissue calcification (PCT Application Publications Nos. WO2014/126965 and WO2016/187408), and a fusion protein of ENPP1 comprising a bone targeting domain has been described to treat GACI (PCT Application Publication No. WO/2012/125182).

There is a need in the art for polypeptides that can be used to treat certain calcification or ossification diseases in vivo. Such polypeptides should have in vivo half-lives that allow for convenient and effective dosing of the polypeptides to the subject in need thereof. The present invention fulfills this need.

BRIEF SUMMARY OF THE INVENTION

The present invention provides an ENPP1 polypeptide fusion comprising an ENPP1 polypeptide fused to a Fc region of an immunoglobulin, wherein the polypeptide fusion comprises at least one point mutation as described herein. The present invention further provides an ENPP1 mutant polypeptide comprising at least one point mutation as described elsewhere herein. The present invention further provides a polypeptide fusion and/or mutant polypeptide, either of which is expressed from a CHO cell line stably transfected with human ST6 beta-galactosamide alpha-2,6-sialyltransferase (ST6GAL1). The present invention further provides a polypeptide fusion and/or mutant polypeptide, either of which is grown in a cell culture supplemented with sialic acid and/or N-acetylmannosamine (1,3,4-O-Bu3ManNAc).

The present invention further provides a method of reducing and/or preventing progression of pathological calcification in a subject in need thereof, the method comprising administering to the subject a therapeutically effective amount of the polypeptide fusion and/or the mutant polypeptide of the invention.

The present invention further provides a method of reducing and/or preventing progression of pathological ossification in a subject in need thereof, the method comprising administering to the subject a therapeutically effective amount of the polypeptide fusion and/or the mutant polypeptide of the invention.

The present invention further provides a method of reducing and/or preventing progression of ectopic calcification of soft tissue in a subject in need thereof, the method comprising administering to the subject a therapeutically effective amount of the polypeptide fusion and/or the mutant polypeptide of the invention.

The present invention further provides a method of treating, reversing, and/or preventing progression of ossification of the posterior longitudinal ligament (OPLL) in a subject in need thereof, the method comprising administering to the subject a therapeutically effective amount of the polypeptide fusion and/or the mutant polypeptide of the invention.

The present invention further provides a method of treating, reverting, and/or preventing progression of hypophosphatemic rickets in a subject in need thereof, the method comprising administering to the subject a therapeutically effective amount of the polypeptide fusion and/or the mutant polypeptide of the invention.

The present invention further provides a method of reducing and/or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of the polypeptide fusion and/or the mutant polypeptide of the invention.

The present invention further provides a method of reducing and/or preventing progression of aging related hardening of arteries in a subject in need thereof the method comprising administering to the subject a therapeutically effective amount of the polypeptide fusion and/or the mutant polypeptide of the invention.

The present invention further provides a method of raising pyrophosphate (PPi) levels in a subject having PPi level lower than PPi normal level, the method comprising administering to the subject a therapeutically effective amount of the polypeptide fusion and/or the mutant polypeptide of the invention, whereby upon the administration the level of the PPi in the subject is elevated to a normal level of at least 2 µM and is maintained at approximately the same level.

The present invention further provides a method of reducing and/or preventing the progression of pathological calcification and/or ossification in a subject having pyrophosphate (PPi) level lower than PPi normal level, the method comprising administering to the subject a therapeutically effective amount of the polypeptide fusion and/or the mutant polypeptide of the invention, whereby pathological calcification and/or ossification in the subject is reduced and/or whereby progression of pathological calcification and/or ossification in the subject is prevented.

The present invention further provides a method of treating ENPP1 deficiency manifested by a reduction of extracellular pyrophosphate (PPi) concentration in a subject in need thereof, the method comprising administering to the subject a therapeutically effective amount of the polypeptide fusion and/or the mutant polypeptide of the invention, whereby the level of the PPi in the subject is elevated.

BRIEF DESCRIPTION OF THE DRAWINGS

The following detailed description of illustrative embodiments of the invention will be better understood when read in conjunction with the appended drawings. For the purpose of illustrating the invention, exemplary embodiments are shown in the drawings. It should be understood, however, that the invention is not limited to the precise arrangements and instrumentalities of the embodiments shown in the drawings.

Figure 1:
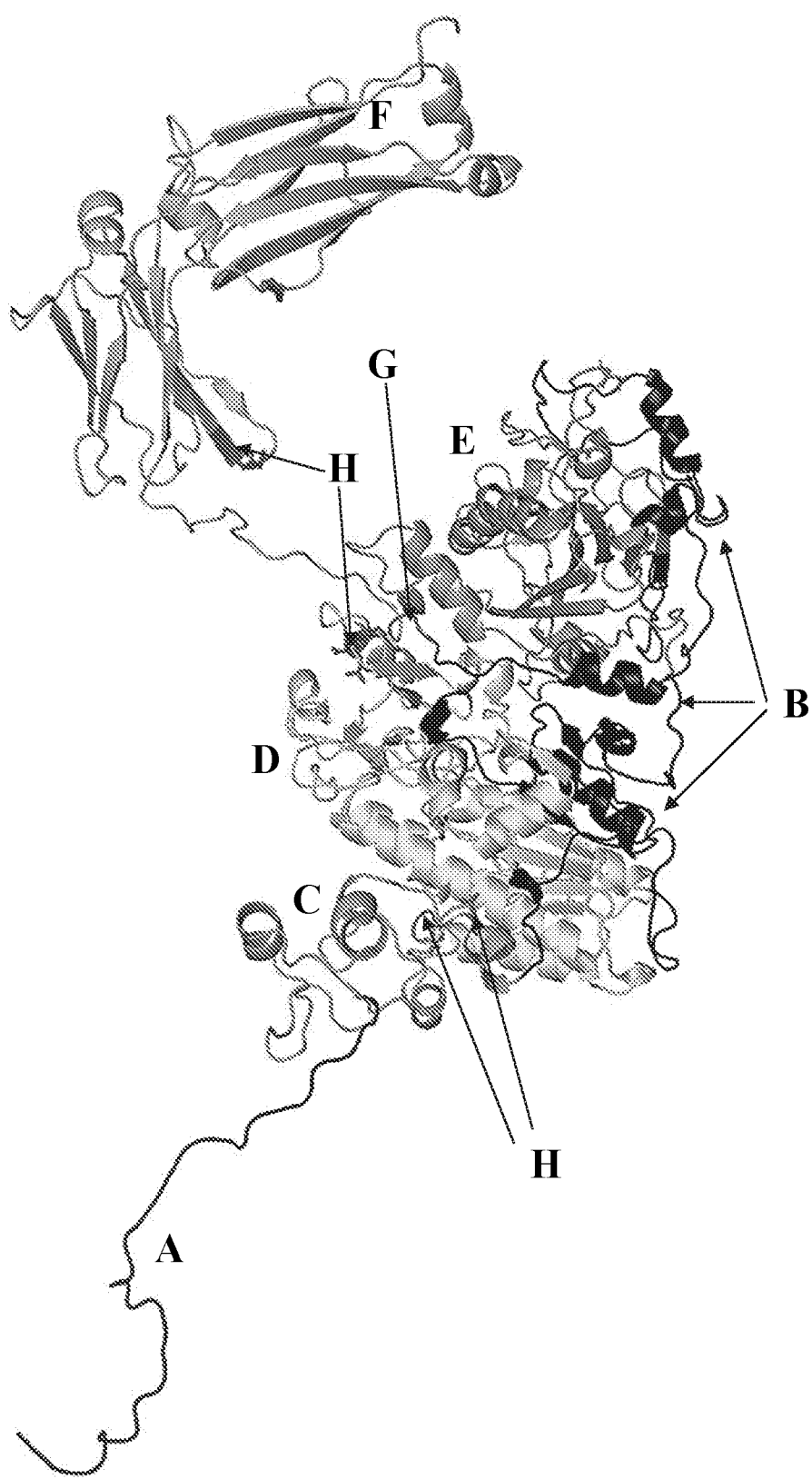
FIG. 1 illustrates an ENPP1 polypeptide contemplated within the invention (SEQ ID NO:7). Point mutations are identified with reference to SEQ ID NO:7, which may also be referred to as the "parent compound" or "Construct #770." The labelling scheme identifies the amino acid number and residue with reference to the numbering scheme illustrated in SEQ ID NO:7 followed by the amino acid that has been substituted for the residue in SEQ ID NO:7. For example, mutation C25N refers to the substitution of an asparagine (Asn or N) for a cysteine (Cys or C) at position 25 of SEQ ID NO:7. Legend: (A)=N-terminal signal sequence from hENPP7; all regions in black (B) represent sequence from hENPP1 that do not have a formal domain definition; (C)=somatomedin B domain of hENPP1; (D)=catalytic domain of hENPP1; (E)=endonuclease domain of hENPP1; (F)=Fc domain from the Invivogen plasmid pFUSE-hIgG1-Fc; (G)=a four amino acid linker between hENPP1 and the Fc domain; (H)=known glycosylation residue.
Figure 2:
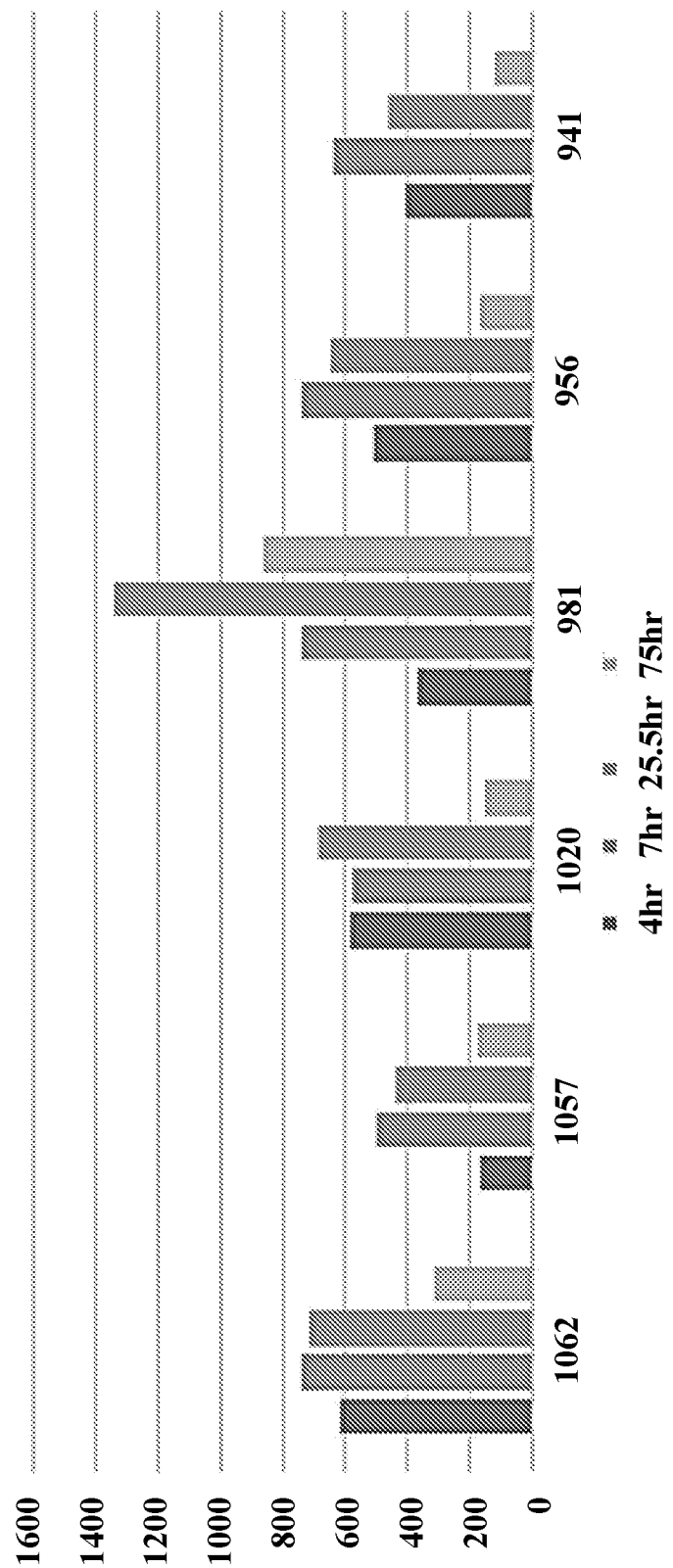
FIG. 2 illustrates a bar graph summarizing plasma phosphodiesterase activity (as measured using the thymidine 5'-monophosphate p-nitrophenyl ester assay, orpNP-TMP assay) after single injection of certain ENPP1 polypeptides in mice (n=3-5). Phosphodiesterase activity in all polypeptides remained elevated after 25 hours, with higher activity at 75 hours observed with Construct #981 (Constructs of interest are outlined in Tables included elsewhere herein).
Figure 3:
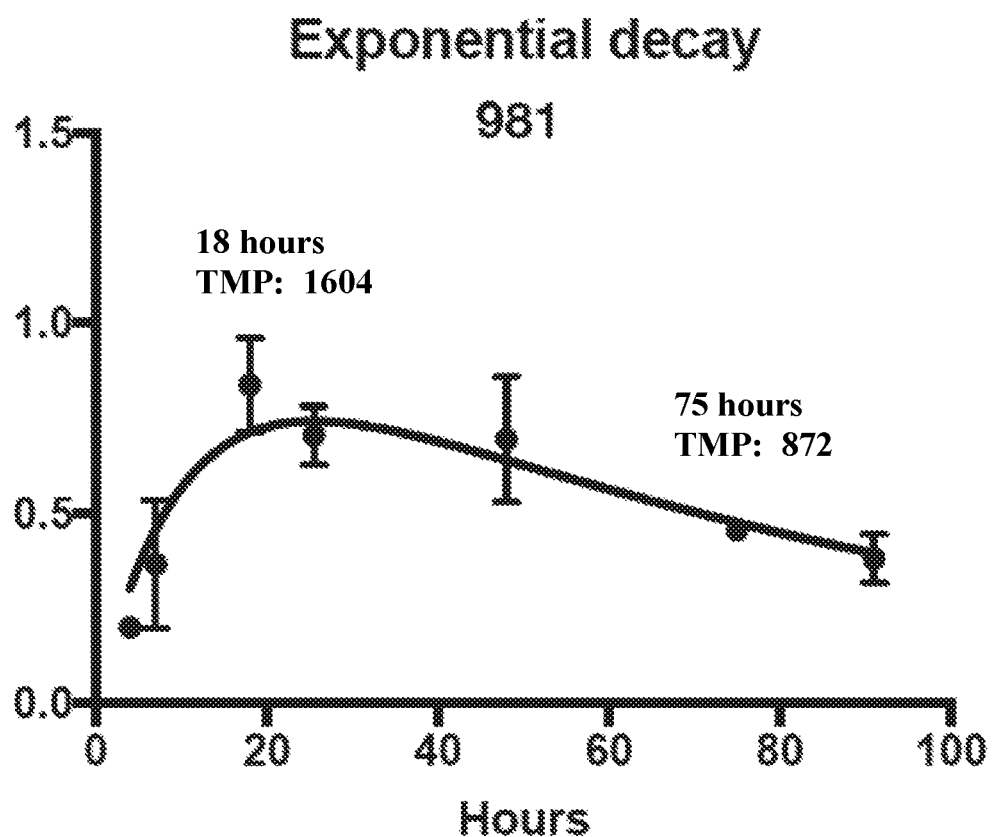
FIG. 3 illustrates in vivo pharmacokinetic data for Construct #981, as measured using the pNP-TMP assay to record enzyme activity in plasma samples of a mouse following subcutaneous injection of the construct. The half-life was estimated to be around 122 hours based on the single subcutaneous bolus injection into 5 mice. Separate experiments to arrive at the half life are described elsewhere herein.
Figure 4:
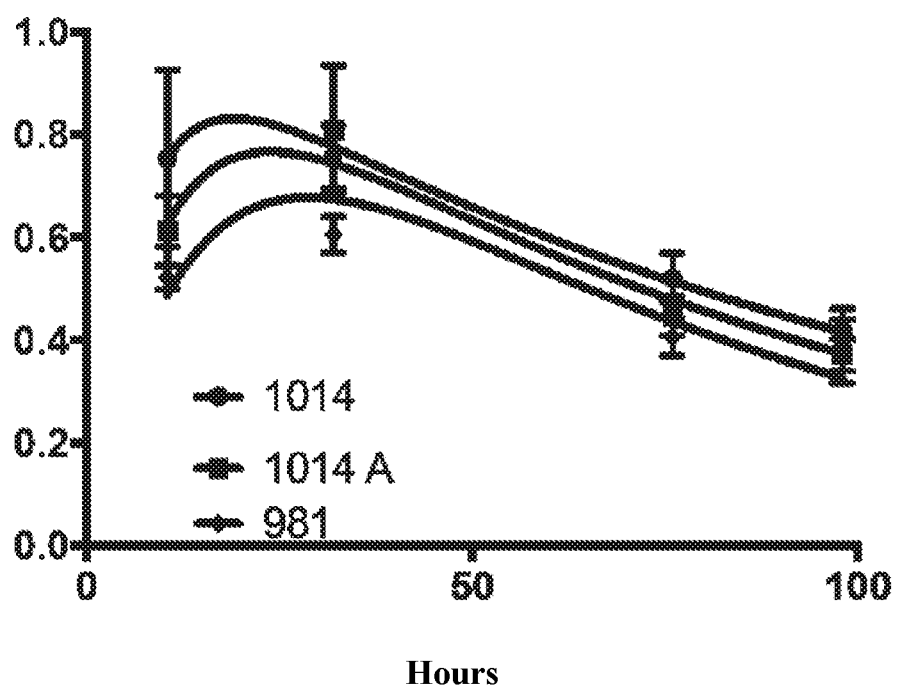
FIG. 4 illustrates selected in vivo pharmacokinetic data for Construct #1014, Construct #1014 prepared in CHO cells grown in culture media supplemented with 1,3,4-O-Bu$_3$ManNAc (denoted as "1014 A" in the graph), and Construct #981. The half-life of constructs can be derived from Equation 1 as described elsewhere herein.
Figure 5:
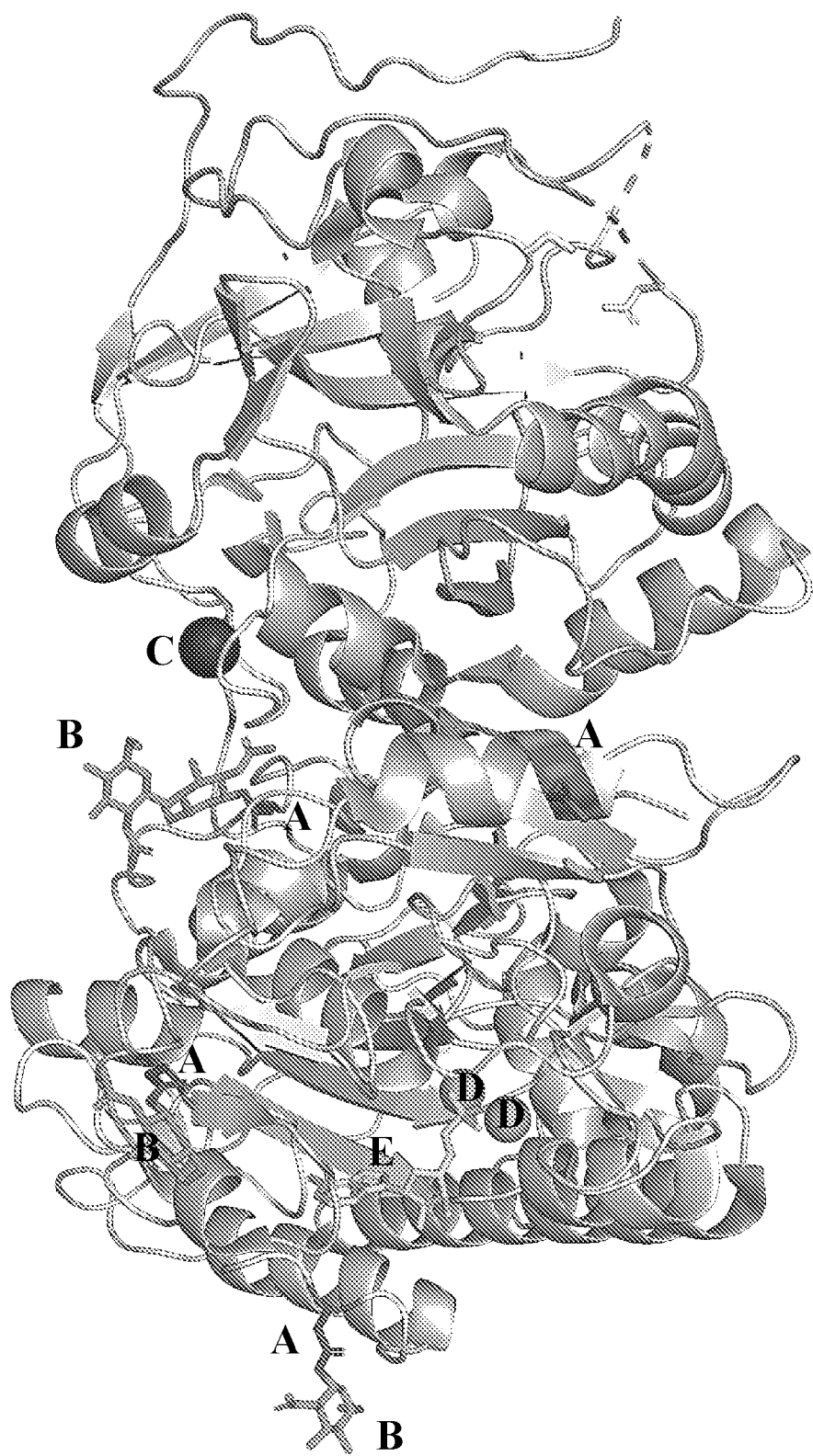
FIG. 5 illustrates three known glycosylation sites in ENPP1, all located in random coil regions: (A)=Asn; (B)=N-acetyl glucosamine. One additional glycosylation site (identified by Surface Glycoprotein Dynamics measurements) is located in Alpha Helix and labeled in red. There is one consensus NLT (Asn Leu Thr) located in PDB area of instability that is yet not known to be glycosylated. There are four more consensus sequences found in hENPP1 whose glycosylation status is unknown. Calcium atom (C); 2 zinc atoms (D); molecule of ATP (E).
Figure 10:
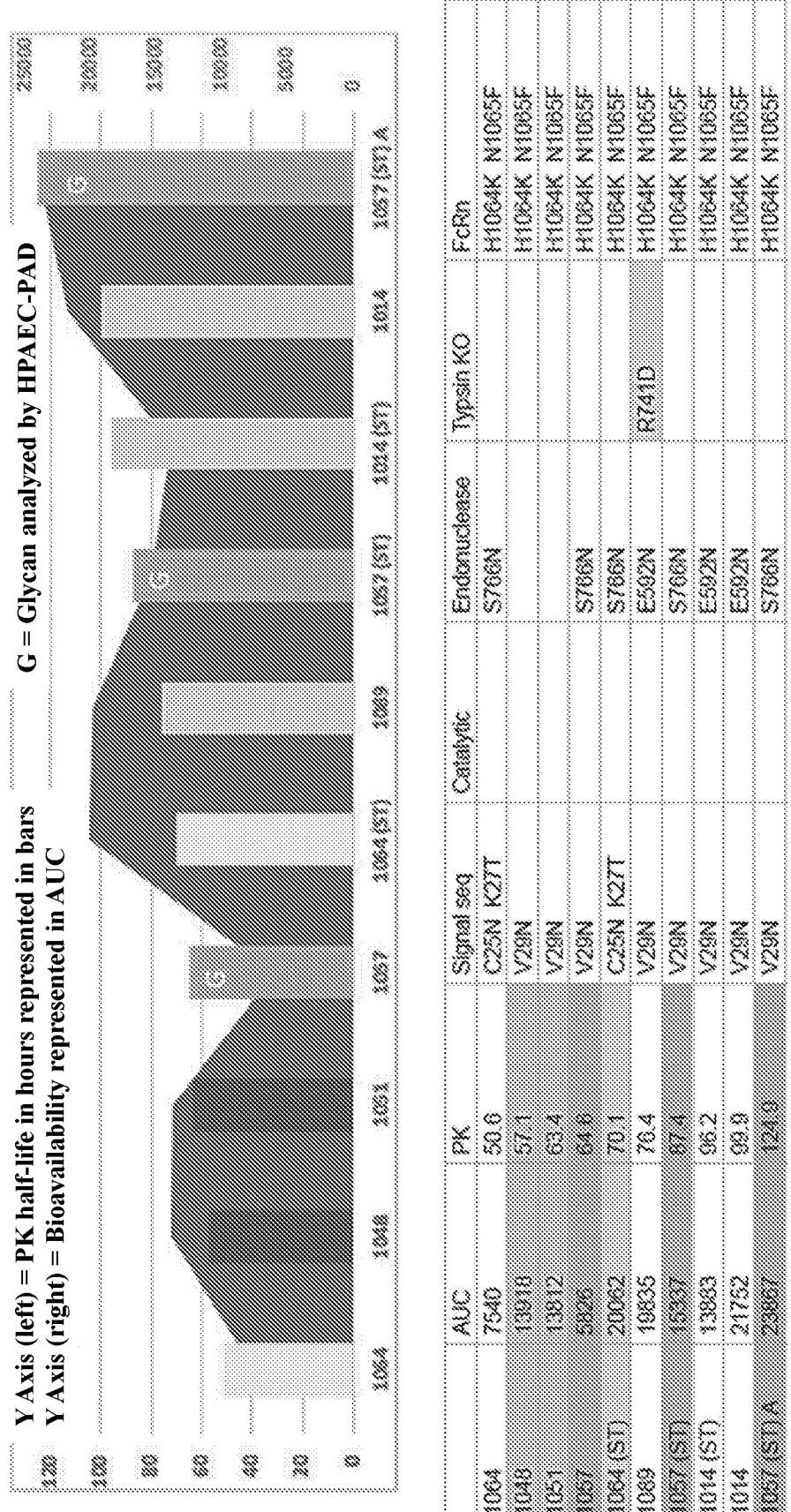

FIG. 10 comprises a graph and a table illustrating the effect of glycosylation and H1064K/N1065F Fc mutations in half-life (PK, in hours) and bioavailability (AUC) of ENPP1 polypeptides. All H1064/N1065-containing Constructs showed improved half-life and AUC values over Construct #770B. Note that Constructs #1048 and #1051 correspond to the same cDNA in two distinct clones, illustrating the reproducibility of the PK/AUC analysis provided herein. Construct #1064 was also grown in cell lines stably transfected with ST6GAL1 (Construct #1064-ST). Construct #1057 was also grown in cell lines stably transfected with ST6GAL1 ("-ST")(Construct #1057-ST) and grown in cell lines stably transfected with ST6GAL1 and supplemented with 1,3,4-O-Bu3-ManNAc ("-A") (Construct #1057-ST-A). Construct #1089 is identical to Construct #1014 but for an added mutation to eliminate a potential trypsin cleavage site. Construct #1014 was also grown in cell lines stably transfected with ST6GAL1 but in this case there was no improvement in PK and bioavailability. PK and bioavailability data are presented in the table, determined as illustrated in FIGS. 3, 4, and 12 and calculated using Equation 1.

Figure 11:
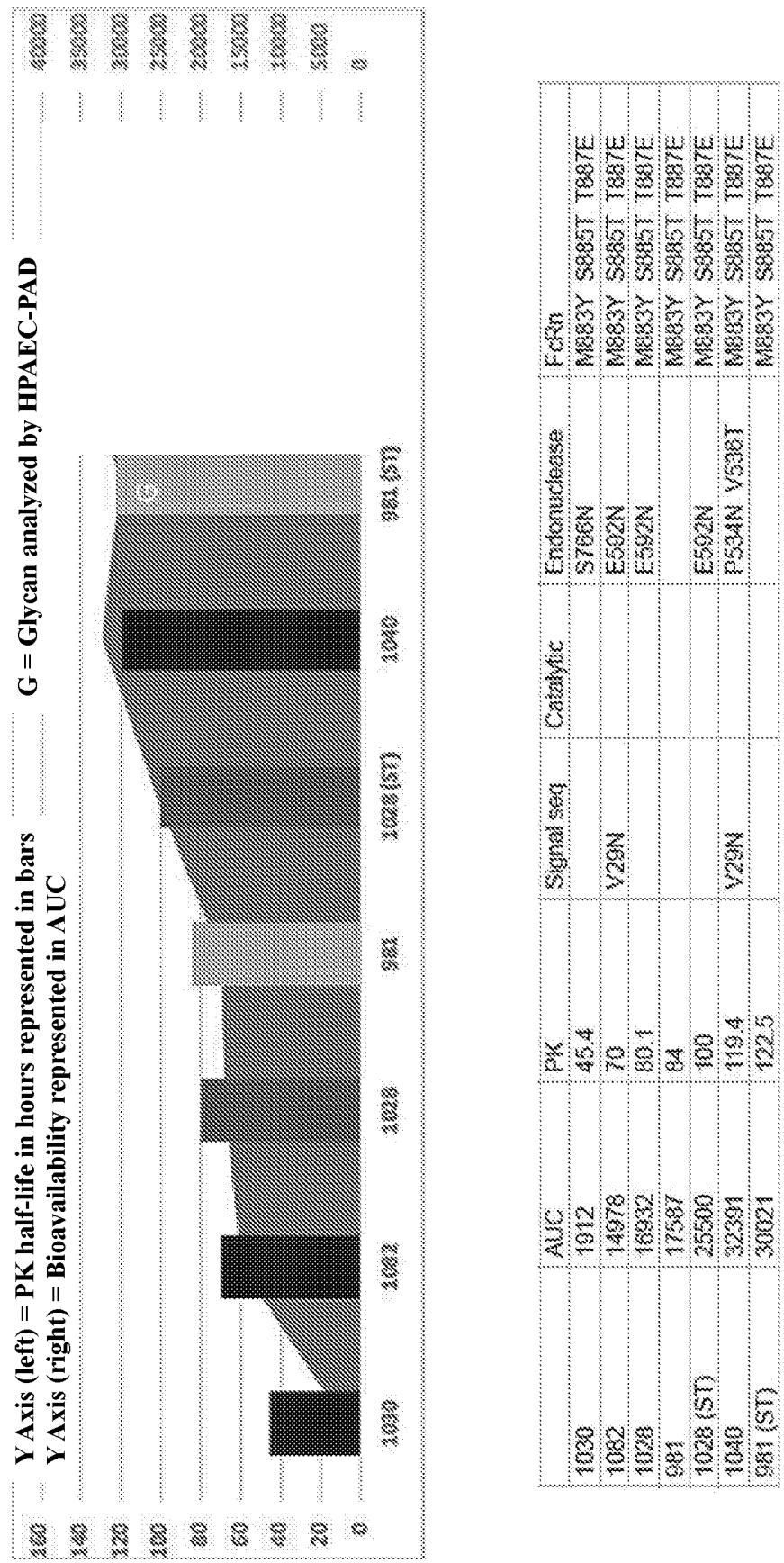

FIG. 11 comprises a graph and a table illustrating the effect of glycosylation and M883Y/S885T/T887E Fc mutation in PK (in terms of half-life, hours) and bioavailability of ENPP1 polypeptides. Construct #1030 has a lower AUC than other Constructs possibly due to the S766N mutation. Constructs #981 and #1028 showed an increase in both PK and AUC values when grown in cell lines stably transfected with ST6GAL1. PK and bioavailability data are presented in the table, determined as illustrated in FIGS. 3, 4, and 12 and calculated using Equation 1.

Figure 12:
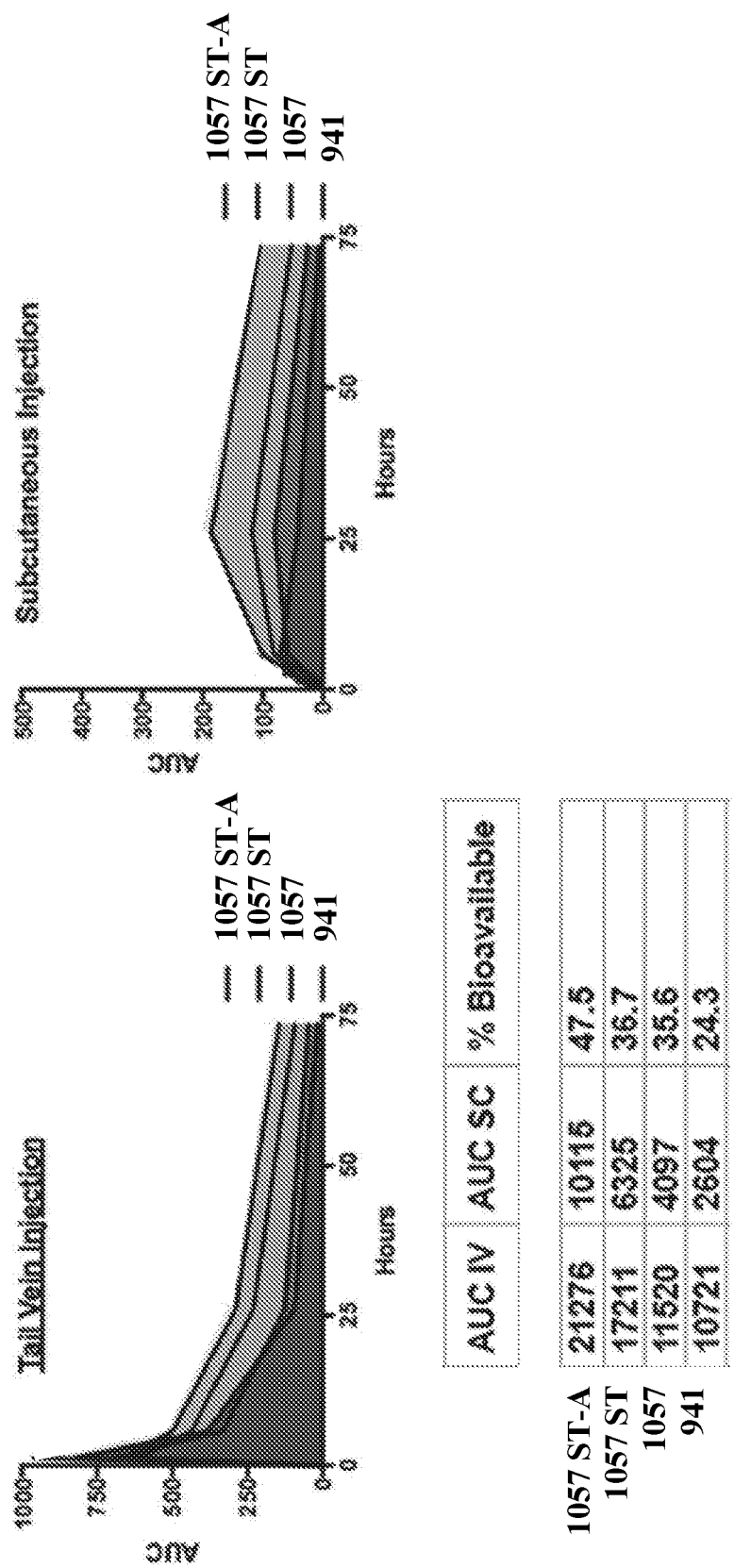

FIG. 12 comprises a set of graphs illustrating the effect of expressing the constructs in CHO cells stably transfected with human α-2,6-ST to produce recombinant biologics with terminal sialic acid residues possessing both alpha-2,3 and alpha-2,6 linkages. These cells are referred to as ST6GAL1 cells or ST cells (denoted as "-ST"). This figure also illustrates the effect of growing constructs in ST6GAL1 cells in the presence of sialic acid, or a high flux precursor of sialic acid known as 1,3,4-O-Bu3-ManNAc (denoted as "-A"). PK and bioavailability data are presented in the table, determined as illustrated in FIGS. 3, 4, and 12 and calculated using Equation 1.

Figure 13A:
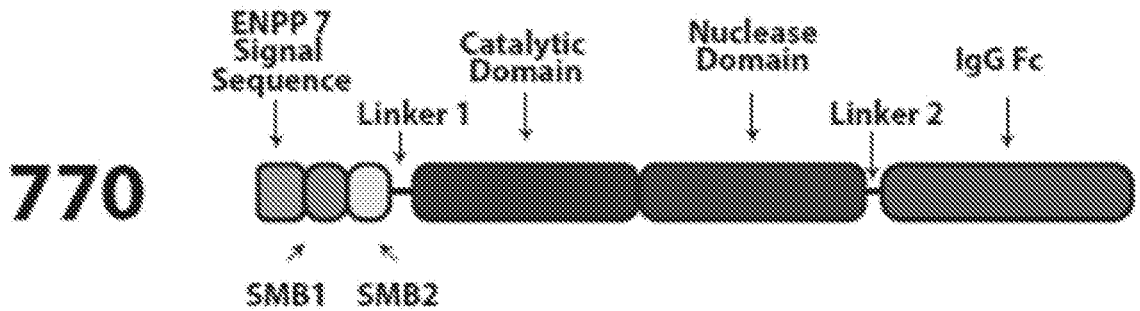
Figure 13B:
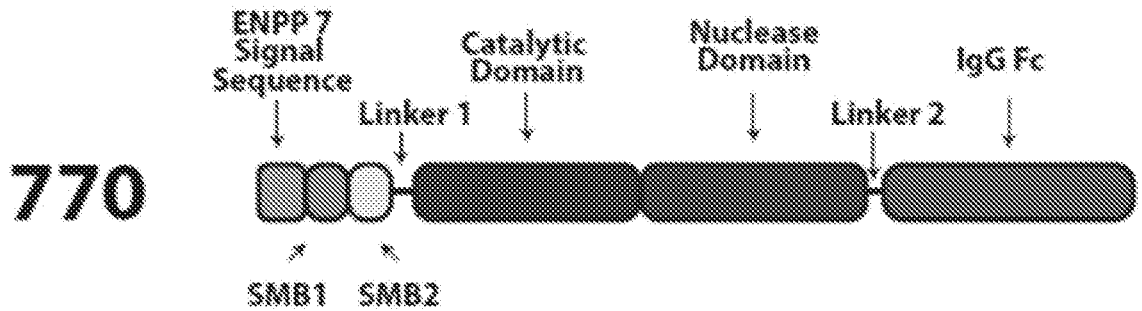

FIG. 13A-13B illustrate domains of ENPP1 and selected point mutations introduced into the parent compound (SEQ ID NO:7). The figure identifies specific point mutations introduced into SEQ ID NO:7. Constructs that have been stably transfected into CHO cells stably transfected with human α-2,6-ST are referred with an "ST". PK and bioavailability data are presented in the table, determined as illustrated in FIGS. 3, 4, and 12 and calculated using Equation 1.

Figure 14:
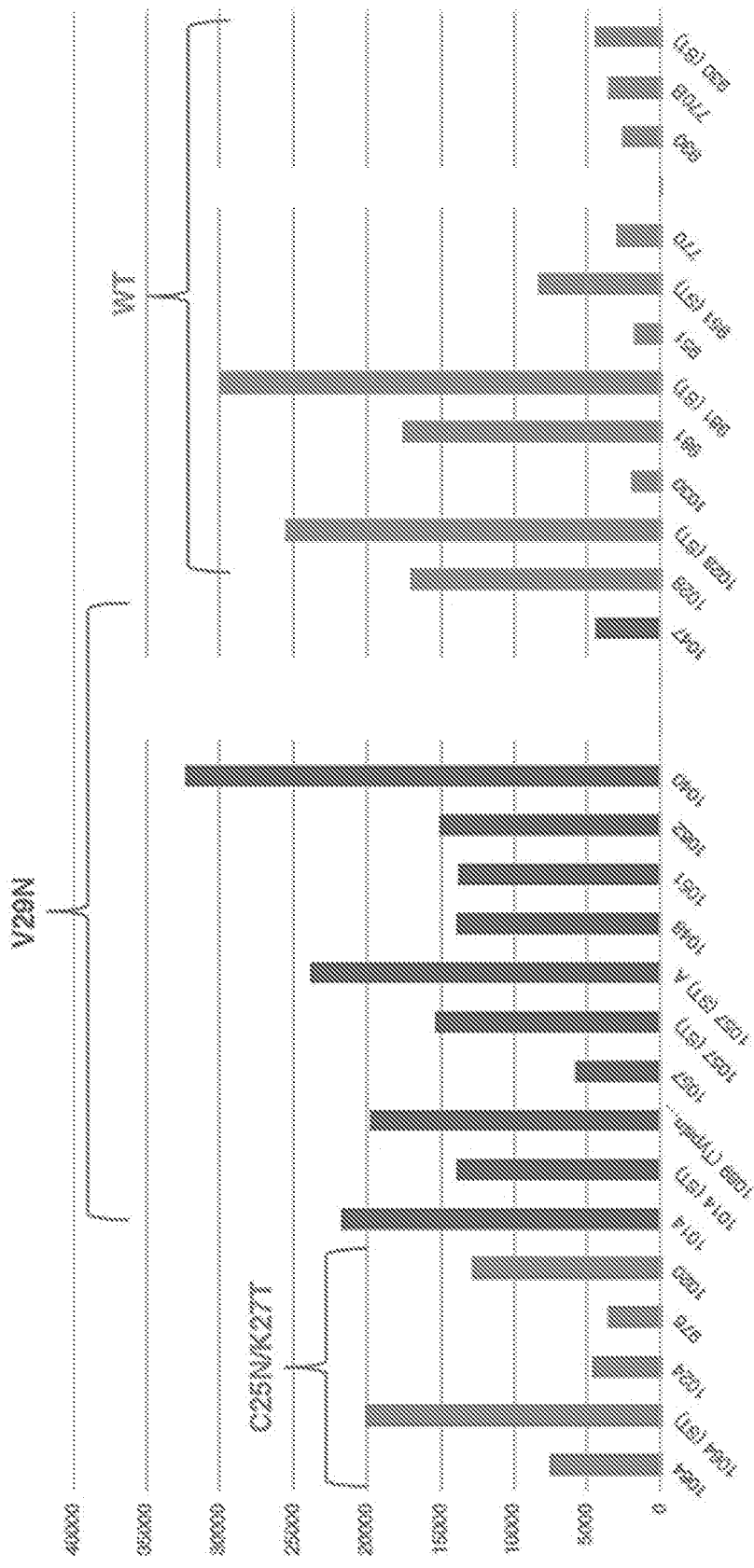

FIG. 14 illustrates bioavailability (as Area Under Curve, or AUC) for certain Constructs of the invention, as sorted by signal sequence (N-terminus region) region mutations.

Figure 15:
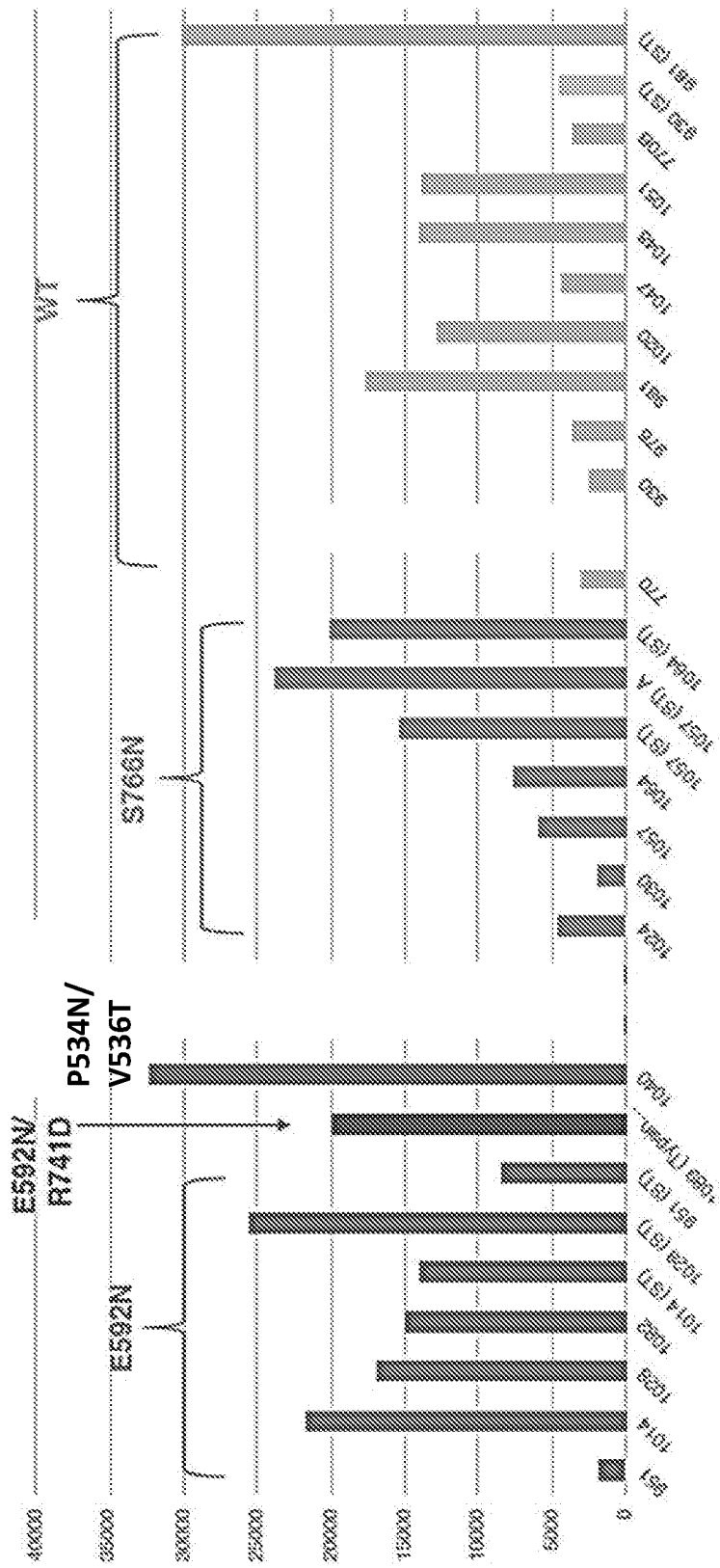

FIG. 15 illustrates bioavailability (as Area Under Curve, or AUC) for certain Constructs of the invention, as sorted by endonuclease region mutations.

DETAILED DESCRIPTION OF THE INVENTION

The present invention relates, in one aspect, to the discovery that certain ENPP1-Fc polypeptides having improved in vivo half-lives as compared to the ENPP1-Fc polypeptides known in the art.

In one aspect, glycosylation was promoted to shield the ENPP1-Fc polypeptides from degradation. This was achieved by introducing additional N-glycan consensus sequences onto the exterior surface of the predicted tertiary structure, guided by three-dimensional models of ENPP1.

In another aspect, pH-dependent FcRn-mediated cellular recycling was increased by mutating the Fc domain to enhance the affinity of the fusion protein for the neonatal receptor (FcRn).

In yet another aspect, sialylation of the fusion protein was enhanced by expressing ENPP1-Fc in CHO cell lines stably transfected with human ST6 beta-galatosamide alpha-2,6-sialyltransferase (also known as ST6GAL1).

In yet another aspect, sialic acid capping was enhanced by supplementing the cell culture media with N-acetylmannosamine (also known as $1,3,4$-O-$Bu_3$ManNAc), which is a "high-flux" precursor of sialic acid.

In certain embodiments, enhancing protein sialyation by expressing the biologic in CHO cells stably transfected with human alpha-2,6-sialyltransferase substantially improved ENPP1-Fc bioavailability ($C_{max}$) when dosed subcutaneously. In other embodiments, increasing the pH-dependent FcRn-mediated cellular recycling by manipulating the Fc domain led to improvements of in vivo biologic half-life. In yet other embodiments, combining CHO cells stably transfected with human α-2,6-sialyltransferase and growing the cells in N-acetylmannosamine led to dramatic increases half-life and/or biologic exposure (AUC). In yet other embodiments, combining two or more methods described herein into a single construct led to dramatic increases in half-life and/or biologic exposure (AUC).

In certain embodiments, the polypeptides of the invention are more highly glycosylated than other ENPP1-Fc polypeptides in the art. In other embodiments, the polypeptides of the invention have higher affinity for the neonatal orphan receptor (FcRn) than other ENPP1-Fc polypeptides in the art. In yet other embodiments, the polypeptides of the invention have higher in vivo half-lives than other ENPP1-Fc polypeptides in the art. In yet other embodiments, the kinetic properties of the parent compound (Construct #770) are altered such that the changes represent a "gain of function" alteration in the enzymatic rate constants. In yet other embodiments, the in vivo half-life of an ENPP1-Fc polypeptide of the invention is at least about 1.5, 2, 2.5, 3, 4, 5, 6, 7, 8, 9, 10, 12, 14, 16, 18, or 20 times higher than the ENPP-1 polypeptides described in the art. In yet other embodiments, the polypeptides of the invention are administered to the subject at a lower dose and/or at a lower frequency than other ENPP1-Fc polypeptides in the art. In yet other embodiments, the polypeptides of the invention are administered to the subject once a month, twice a month, three times a month, and/or four times a month. In yet other embodiments, the lower frequency administration of the polypeptides of the invention results in better patient compliance and/or increased efficacy as compared with other ENPP1-Fc polypeptides in the art.

In certain embodiments, an ENPP1-Fc polypeptide of the invention can be used to raise pyrophosphate (PPi) levels in a subject having PPi level lower than normal level (which is around 2 µM). In other embodiments, an ENPP1-Fc polypeptide of the invention can be used to reduce or prevent progression of pathological calcification or ossification in a subject having PPi levels lower than normal level. In yet other embodiments, an ENPP1-Fc polypeptide of the invention can be used to treat ENPP1 deficiency manifested by a reduction of extracellular PPi concentration in a subject.

In certain embodiment, the steady state level of plasma PPi achieved after administration of a first dosage of a construct of the invention is maintained for a time period of at least 2 days, at least 4 days, at least a week or at least a month.

In certain embodiment, a second dosage of a construct of the invention is administered after a suitable time interval of after two days, after four days, after a week, or after a month to the subject so that the steady state level of plasma PPi is maintained at a constant or steady state level and does not return to the lower level of PPi that the subject had prior to the administration of first dosage of constructs of the invention.

Without wishing to be bound be theory, it is believed that maintaining a steady state concentration of plasma PPi at normal levels reduces and/or prevents progression of pathological calcification and pathological ossification of subjects.

Certain ENPP1 polypeptides, mutants, or mutant fragments thereof, have been previously disclosed in International PCT Application Publications No. WO 2012/125182, WO 2014/126965, WO 2016/187408, and WO 2018/027024, all of which are incorporated by reference in their entireties herein.

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B."

The following notation conventions are applied to the present disclosure for the sake of clarity. In any case, any teaching herein that does not follow this convention is still part of the present disclosure, and can be fully understood in view of the context in which the teaching is disclosed. Protein symbols are disclosed in non-italicized capital letters. As non-limiting examples, 'ENPP1' refer to the protein. In certain embodiments, if the protein is a human protein, an 'h' is used before the protein symbol. In other embodiments, if the protein is a mouse protein, an 'm' is used before the symbol. Hence, human ENPP1 is referred to as 'hENPP1', and mouse ENPP1 is referred to as 'mENPP1'. Human gene symbols are disclosed in italicized capital letters. As a non-limiting example, the human gene corresponding to the protein hENPP1 is ENPP1. Mouse gene symbols are disclosed with the first letter in upper case and the remaining letters in lower case; further, the mouse gene symbol is italicized. As a non-limiting example, the mouse gene that makes the protein mEnpp1 is Enpp1. Notations about gene mutations are shown as uppercase text.

"About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

A disease or disorder is "alleviated" if the severity of a symptom of the disease or disorder, the frequency with which such a symptom is experienced by a patient, or both, is reduced.

As used herein the terms "alteration," "defect," "variation" or "mutation" refer to a mutation in a gene in a cell that affects the function, activity, expression (transcription or translation) or conformation of the polypeptide it encodes, including missense and nonsense mutations, insertions, deletions, frameshifts and premature terminations.

The term "antibody," as used herein, refers to an immunoglobulin molecule that is able to specifically bind to a specific epitope on an antigen. Antibodies can be intact immunoglobulins derived from natural sources or from recombinant sources and can be immunoreactive portions of intact immunoglobulins.

The "ATP hydrolytic activity" of ENPP1 can be determined by using an ATP cleavage assay. ENPP1 readily hydrolyzes ATP into AMP and PPi. The steady-state Michaelis-Menten enzymatic constants of ENPP1 are determined using ATP as a substrate. ENPP1 can be demonstrated to cleave ATP by HPLC analysis of the enzymatic reaction, and the identity of the substrates and products of the reaction are confirmed by using ATP, AMP, and ADP standards. The ATP substrate degrades over time in the presence of ENPP1, with the accumulation of the enzymatic product AMP. Using varying concentrations of ATP substrate, the initial rate velocities for ENPP1 are derived in the presence of ATP, and the data is fit to a curve to derive the enzymatic rate constants. At physiologic pH, the kinetic rate constants of NPP1 are $K_m=144$ µM and $k_{cat}=7.8$ s$^{-1}$.

As used herein, the term "AUC" refers to the area under the plasma drug concentration-time curve (AUC) and correlates with actual body exposure to drug after administration of a dose of the drug. In certain embodiments, the AUC is expressed in mg*h/L. The AUC can be used to measure bioavailability of a drug, which is the fraction of unchanged drug that is absorbed intact and reaches the site of action, or the systemic circulation following administration by any route.

AUC can be calculated used Linear Trapezoidal method or Logarithmic Trapezoidal method. The Linear Trapezoidal method uses linear interpolation between data points to calculate the AUC. This method is required by the OGD and FDA, and is the standard for bioequivalence trials. For a given time interval ($t_1$-$t_2$), the AUC can be calculated as follows:

$$AUC = \frac{1}{2}(C_1 + C_2)(t_2 - t_1)$$

wherein $C_1$ and $C_2$ are the average concentration over the time interval ($t_1$ and $t_2$).

The Logarithmic Trapezoidal method uses logarithmic interpolation between data points to calculate the AUC. This method is more accurate when concentrations are decreasing because drug elimination is exponential (which makes it linear on a logarithmic scale). For a given time interval ($t_1$-$t_2$), the AUC can be calculated as follows (assuming that $C_1>C_2$):

$$AUC = \frac{C_1 - C_2}{\ln(C_1) - \ln(C_2)}(t_2 - t_1)$$

The term "bioavailability" as used herein refers to the extent and rate at which the active moiety (protein or drug or metabolite) enters systemic circulation, thereby accessing the site of action. Bioavailability of an active moiety is largely determined by the properties of the dosage form, which depend partly on its design and manufacture. Differences in bioavailability among formulations of a given drug or protein can have clinical significance; thus, knowing whether drug formulations are equivalent is essential. The most reliable measure of a drug's or protein's bioavailability is area under the plasma concentration-time curve (AUC). AUC is directly proportional to the total amount of unchanged drug or therapeutic protein that reaches systemic circulation. Drug or therapeutic protein may be considered bioequivalent in extent and rate of absorption if their plasma concentration curves are essentially superimposable.

The term "bioavailability" of a drug or therapeutic product is defined as the fraction of unchanged drug that is absorbed intact and reaches the site of action, or the systemic circulation following administration by any route. For an intravenous dose of a drug, bioavailability is defined as unity. For drug administered by other routes of administration, bioavailability is often less than unity. Incomplete bioavailability may be due to a number of factors that can be subdivided into categories of dosage form effects, membrane effects, and site of administration effect. Half-life and AUC provide information about the bioavailability of a drug or biologic.

As used herein, the terms "conservative variation" or "conservative substitution" as used herein refers to the replacement of an amino acid residue by another, biologically similar residue. Conservative variations or substitutions are not likely to change the shape of the peptide chain. Examples of conservative variations, or substitutions, include the replacement of one hydrophobic residue such as isoleucine, valine, leucine or methionine for another, or the substitution of one polar residue for another, such as the substitution of arginine for lysine, glutamic for aspartic acid, or glutamine for asparagine.

As used herein, a "construct" of the invention refers to a fusion polypeptide comprising an ENPP1 polypeptide, or a fragment or site directed mutant thereof.

A "disease" is a state of health of an animal wherein the animal cannot maintain homeostasis, and wherein if the disease is not ameliorated then the animal's health continues to deteriorate.

A "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "ENPP" or "NPP" refers to ectonucleotide pyrophosphatase/phosphodiesterase.

As used herein, the term "ENPP1 protein" or "ENPP1 polypeptide" refers to ectonucleotide pyrophosphatase/phosphodiesterase-1 protein encoded by the ENPP1 gene. The encoded protein is a type II transmembrane glycoprotein and cleaves a variety of substrates, including phosphodiester bonds of nucleotides and nucleotide sugars and pyrophosphate bonds of nucleotides and nucleotide sugars. ENPP1 protein has a transmembrane domain and soluble extracellular domain. The extracellular domain is further subdivided into somatomedin B domain, catalytic domain, and the nuclease domain. The sequence and structure of wild-type ENPP1 is described in detail in PCT Application Publication No. WO 2014/126965 to Braddock, et al., which is incorporated herein in its entirety by reference.

The term "functional equivalent" or "functional derivative" denotes, in the context of a functional derivative of an amino acid sequence, a molecule that retains a biological activity (either function or structural) that is substantially similar to that of sequences of ENPP1-Fc constructs shown herein. A functional derivative or equivalent may be a natural derivative or is prepared synthetically. The functionally-equivalent polypeptides of the invention can also be polypeptides identified using one or more techniques of structural and or sequence alignment known in art.

Exemplary functional derivatives include amino acid sequences having substitutions, deletions, or additions of one or more amino acids, provided that the biological activity of the protein is conserved. The substituting amino acid desirably has chemico-physical properties which are similar to that of the substituted amino acid. Desirable similar chemico-physical properties include, similarities in charge, bulkiness, hydrophobicity, hydrophilicity, and the like. Typically, greater than 30% identity between two polypeptides is considered to be an indication of functional equivalence. Preferably, functionally equivalent polypeptides of the invention have a degree of sequence identity with the ENPP1-Fc constructs of greater than 80%. More preferred polypeptides have degrees of identity of greater than 85%, 90%, 95%, 98% or 99%, respectively. Method for determining whether a functional equivalent or functional derivative has the same or similar or higher biological activity than the ENPP1-Fc construct can be determined by using the Enzymology assays involving ATP cleavage described in WO2016/187408.

As used herein, the term "human ENPP1" refers to the human ENPP1 sequence as described in NCBI accession NP 006199. As used herein, the term "soluble human ENPP1" refers to the polypeptide corresponding to residues 96 to 925 of NCBI accession NP_006199. As used herein, the term "enzymatically active" with respect to ENPP1 is defined as being capable of binding and hydrolyzing ATP into AMP and PPi and/or AP3a into ATP.

As used herein, the term "ENPP1 precursor protein" refers to ENPP1 with its signal peptide sequence at the ENPP1 N-terminus. Upon proteolysis, the signal sequence is cleaved from ENPP1 to provide the ENPP1 protein. Signal peptide sequences useful within the invention include, but are not limited to, ENPP1 signal peptide sequence, ENPP2 signal peptide sequence, ENPP7 signal peptide sequence, and/or ENPP5 signal peptide sequence.

As used herein, the term "ENPP1-Fc" refers to ENPP1 recombinantly fused and/or chemically conjugated (including both covalent and non-covalent conjugations) to an FcR binding domain of an IgG molecule (preferably, a human IgG). In certain embodiments, the C-terminus of ENPP1 is fused or conjugated to the N-terminus of the FcR binding domain.

As used herein, the term "Fc" refers to a human IgG (immunoglobulin) Fc domain. Subtypes of IgG such as IgG1, IgG2, IgG3, and IgG4 are contemplated for usage as Fc domains.

As used herein, the "Fc region" is the portion of an IgG molecule that correlates to a crystallizable fragment obtained by papain digestion of an IgG molecule. The Fc region comprises the C-terminal half of the two heavy chains of an IgG molecule that are linked by disulfide bonds. It has no antigen binding activity but contains the carbohydrate moiety and the binding sites for complement and Fc receptors, including the FcRn receptor. The Fc fragment contains the entire second constant domain CH2 (residues 231-340 of human IgG1, according to the Kabat numbering system) and the third constant domain CH3 (residues 341-447). The term "IgG hinge-Fc region" or "hinge-Fc fragment" refers to a region of an IgG molecule consisting of the Fc region (residues 231-447) and a hinge region (residues 216-230) extending from the N-terminus of the Fc region. The term "constant domain" refers to the portion of an immunoglobulin molecule having a more conserved amino acid sequence relative to the other portion of the immunoglobulin, the variable domain, which contains the antigen binding site. The constant domain contains the CH1, CH2 and CH3 domains of the heavy chain and the CHL domain of the light chain.

As used herein, the term "Fc receptors" refer to proteins found on the surface of certain cells (including, among others, B lymphocytes, follicular dendritic cells, natural killer cells, macrophages, neutrophils, eosinophils, basophils, human platelets, and mast cells) that contribute to the protective functions of the immune system. Fc receptors bind to antibodies that are attached to infected cells or invading pathogens. Immunoglobulin Fc receptors (FcRs) are expressed on all hematopoietic cells and play crucial roles in antibody-mediated immune responses. Binding of immune complexes to FcR activates effector cells, leading to phagocytosis, endocytosis of IgG-opsonized particles, releases of inflammatory mediators, and antibody-dependent cellular cytotoxicity (ADCC). Fc receptors have been described for all classes of immunoglobulins: Fc$\gamma$R and neonatal FcR (FcRn) for IgG, Fc$\epsilon$R for IgE, Fc$\alpha$R for IgA, Fc$\delta$R for IgD and Fc$\mu$R for IgM. All known Fc receptors structurally belong to the immunoglobulin superfamily, except for FcRn and Fc$\epsilon$RII, which are structurally related to class I Major Histocompatibility antigens and C-type lectins, respectively (*Fc Receptors*, Neil A. Fangera, et al., in Encyclopedia of Immunology ($2^{nd}$ Edition), 1998).

As used herein, the term "FcRn Receptor" refers to the neonatal Fc receptor (FcRn), also known as the Brambell receptor, which is a protein that in humans is encoded by the FCGRT gene. An FcRn specifically binds the Fc domain of an antibody. FcRn extends the half-life of IgG and serum albumin by reducing lysosomal degradation in endothelial cells. IgG, serum albumin, and other serum proteins are continuously internalized through pinocytosis. Generally, serum proteins are transported from the endosomes to the lysosome, where they are degraded. FcRn-mediated transcytosis of IgG across epithelial cells is possible because FcRn binds IgG at acidic pH (<6.5) but not at neutral or higher pH. IgG and serum albumin are bound by FcRn at the slightly acidic pH (<6.5), and recycled to the cell surface where they are released at the neutral pH (>7.0) of blood. In this way IgG and serum albumin avoid lysosomal degradation.

The Fc portion of an IgG molecule is located in the constant region of the heavy chain, notably in the CH2 domain. The Fc region binds to an Fc receptor (FcRn), which is a surface receptor of a B cell and also proteins of the complement system. The binding of the Fc region of an IgG molecule to an FcRn activates the cell bearing the receptor and thus activates the immune system. The Fc residues critical to the mouse Fc-mouse FcRn and human Fc-human FcRn interactions have been identified (Dall'Acqua et al., 2002, J. Immunol. 169(9):5171-80). An FcRn binding domain comprises the CH2 domain (or a FcRn binding portion thereof) of an IgG molecule.

As used herein, the term "fragment," as applied to a nucleic acid, refers to a subsequence of a larger nucleic acid. A "fragment" of a nucleic acid can be at least about 15, 50-100, 100-500, 500-1000, 1000-1500 nucleotides, 1500-2500, or 2500 nucleotides (and any integer value in between). As used herein, the term "fragment," as applied to a protein or peptide, refers to a subsequence of a larger protein or peptide, and can be at least about 20, 50, 100, 200, 300 or 400 amino acids in length (and any integer value in between).

As used herein, the term "in vivo half-life" for a protein and/or polypeptide contemplated within the invention (such as, for example, an ENPP1 polypeptide containing FcRn binding sites) refers to the time required for half the quantity administered in the animal to be cleared from the circulation and/or other tissues in the animal. When a clearance curve of an ENPP1-Fc fusion protein is constructed as a function of time, the curve is usually biphasic with a rapid α-phase (which represents an equilibration of the administered molecules between the intra- and extra-vascular space and which is, in part, determined by the size of molecules), and a longer β-phase (which represents the catabolism of the molecules in the intravascular space). In certain embodiments, the term "in vivo half-life" in practice corresponds to the half-life of the molecules in the β-phase.

"Instructional material," as that term is used herein, includes a publication, a recording, a diagram, or any other medium of expression that can be used to communicate the usefulness of the nucleic acid, peptide, and/or compound of the invention in the kit for identifying or alleviating or treating the various diseases or disorders recited herein.

"Isolated" means altered or removed from the natural state. For example, a nucleic acid or a polypeptide naturally present in a living animal is not "isolated," but the same nucleic acid or polypeptide partially or completely separated from the coexisting materials of its natural state is "isolated." An isolated nucleic acid or protein can exist in substantially purified form, or can exist in a non-native environment such as, for example, a host cell.

An "oligonucleotide" or "polynucleotide" is a nucleic acid ranging from at least 2, in certain embodiments at least 8, 15 or 25 nucleotides in length, but may be up to 50, 100, 1000, or 5000 nucleotides long or a compound that specifically hybridizes to a polynucleotide.

As used herein, the term "patient," "individual" or "subject" refers to a human.

As used herein, the term "pharmaceutical composition" or "composition" refers to a mixture of at least one compound useful within the invention with a pharmaceutically acceptable carrier. The pharmaceutical composition facilitates administration of the compound to a patient. Multiple techniques of administering a compound exist in the art including, but not limited to, subcutaneous, intravenous, oral, aerosol, inhalational, rectal, vaginal, transdermal, intranasal, buccal, sublingual, parenteral, intrathecal, intragastrical, ophthalmic, pulmonary, and topical administration.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof.

As used herein the term "plasma pyrophosphate (PPi) levels" refers to the amount of pyrophosphate present in plasma of animals. In certain embodiments, animals include rat, mouse, cat, dog, human, cow and horse. It is necessary to measure PPi in plasma rather than serum because of release from platelets. There are several ways to measure PPi, one of which is by enzymatic assay using uridine-diphosphoglucose (UDPG) pyrophosphorylase (Lust & Seegmiller, 1976, Clin. Chim. Acta 66:241-249; Cheung & Suhadolnik, 1977, Anal. Biochem. 83:61-63) with modifications. Typically normal PPi levels in healthy subjects range from about 1 μm to about 3 μM, in some cases between 1-2 μM. Subjects with defective ENPP1 expression tend to exhibit low PPi levels ranging from at least 10% below normal levels, at least 20% below normal levels, at least 30% below normal levels, at least 40% below normal levels, at least 50% below normal levels, at least 60% below normal levels, at least 70% below normal levels, at least 80% below normal levels, and any combinations thereof. In patients afflicted with diseases of pathological calcification or ossification, the PPi levels in blood plasma are found to be less than 1 μM and in some cases are below detection levels. In some cases, the plasma PPi levels of subjects afflicted with diseases of pathological calcification or ossification are below 0.5 μM (Arterioscler Thromb Vasc Biol. 2014, 34(9):1985-9; Braddock et al., 2015, Nat Commun. 6:10006.)

As used herein, the term "polypeptide" refers to a polymer composed of amino acid residues, related naturally occurring structural variants, and synthetic non-naturally occurring analogues thereof linked via peptide bonds.

As used herein, the term "PPi" refers to pyrophosphate.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

"Sample" or "biological sample" as used herein means a biological material isolated from a subject. The biological sample may contain any biological material suitable for detecting a mRNA, polypeptide or other marker of a physiologic or pathologic process in a subject, and may comprise fluid, tissue, cellular and/or non-cellular material obtained from the individual.

As used herein, the term "signal peptide" refers to a sequence of amino acid residues (ranging in length from, for example, 10-30 residues) bound at the amino terminus of a nascent protein of interest during protein translation. The signal peptide is recognized by the signal recognition particle (SRP) and cleaved by the signal peptidase following transport at the endoplasmic reticulum. (Lodish, et al., 2000, Molecular Cell Biology, 4$^{th}$ edition).

As used herein, "substantially purified" refers to being essentially free of other components. For example, a substantially purified polypeptide is a polypeptide that has been separated from other components with which it is normally associated in its naturally occurring state. Non-limiting embodiments include 95% purity, 99% purity, 99.5% purity, 99.9% purity and 100% purity.

As used herein, the term "treatment" or "treating" is defined as the application or administration of a therapeutic agent, i.e., a compound useful within the invention (alone or in combination with another pharmaceutical agent), to a patient, or application or administration of a therapeutic agent to an isolated tissue or cell line from a patient (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder, or the potential to develop the disease or disorder. Such treatments may be specifically tailored or modified, based on knowledge obtained from the field of pharmacogenomics.

A "vector" is a composition of matter that comprises an isolated nucleic acid and that may be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

As used herein, the term "wild-type" refers to a gene or gene product isolated from a naturally occurring source. A wild-type gene is most frequently observed in a population and is thus arbitrarily designed the "normal" or "wild-type" form of the gene. In contrast, the term "modified" or "mutant" refers to a gene or gene product that displays modifications in sequence and/or functional properties (i.e., altered characteristics) when compared to the wild-type gene or gene product. Naturally occurring mutants can be isolated; these are identified by the fact that they have altered characteristics (including altered nucleic acid sequences) when compared to the wild-type gene or gene product.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Polypeptides

In one aspect, the invention provides an ENPP1-Fc polypeptide. The invention contemplates that the polypeptide of the invention can have one or more of the mutations described herein.

In certain embodiments, the ENPP1 polypeptide comprises at least one mutation in the signal sequence region as recited in FIG. 13A and/or FIG. 13B. In certain embodiments, the mutation is selected from the group consisting of C25N, K27T, and V29N as relating to SEQ ID NO:7. In certain embodiments, the mutation is C25N as relating to SEQ ID NO:7. In certain embodiments, the mutation is K27T as relating to SEQ ID NO:7. In certain embodiments, the mutation is V29N as relating to SEQ ID NO:7. In certain embodiments, the ENPP1 polypeptide comprises at least one mutation selected from the group consisting of C25N/K27T and V29N as relating to SEQ ID NO:7.

In certain embodiments, the ENPP1 polypeptide comprises at least one mutation in the catalytic region as recited in FIG. 13A and/or FIG. 13B. In certain embodiments, the mutation is selected from the group consisting of K369N and I371T as relating to SEQ ID NO:7. In certain embodiments, the mutation is K369N as relating to SEQ ID NO:7. In certain embodiments, the mutation is I371T as relating to SEQ ID NO:7. In certain embodiments, the ENPP1 polypeptide comprises the mutation K369N/I371T as relating to SEQ ID NO:7.

In certain embodiments, the ENPP1 polypeptide comprises at least one mutation in the endonuclease domain as recited in Table 1, Table 2, Table 3, Table 4, Table 5, FIG. 6A, FIG. 13A, FIG. 13B, FIG. 14, and/or FIG. 15. In certain embodiments, the mutation is selected from the group consisting of P534N, V536T, R545T, P554L, E592N, R741D, and S766N as relating to SEQ ID NO:7. In certain embodiments, the mutation is P534N as relating to SEQ ID NO:7. In certain embodiments, the mutation is V536T as relating to SEQ ID NO:7. In certain embodiments, the mutation is R545T as relating to SEQ ID NO:7. In certain embodiments, the mutation is P554L as relating to SEQ ID NO:7. In certain embodiments, the mutation is E592N as relating to SEQ ID NO:7. In certain embodiments, the mutation is R741D as relating to SEQ ID NO:7. In certain embodiments, the mutation is S766N as relating to SEQ ID NO:7. In certain embodiments, the ENPP1 polypeptide comprises at least one mutation selected from the group consisting of P534N/V536T, P554L/R545T, E592N, E592N/R741D, and S766N as relating to SEQ ID NO:7.

In certain embodiments, the ENPP1 polypeptide comprises at least one mutation in the linker region as recited in FIG. 13A and/or FIG. 13B. In certain embodiments, the mutation is selected from the group consisting of E864N and L866T as relating to SEQ ID NO:7. In certain embodiments, the mutation is E864N as relating to SEQ ID NO:7. In certain embodiments, the mutation is L866T as relating to SEQ ID NO:7.

In certain embodiments, the ENPP1 polypeptide comprises at least the mutation E864N/L866T as relating to SEQ ID NO:7.

In certain embodiments, the polypeptide comprises an ENPP1 polypeptide and an FcRn binding domain, wherein the FcRn binding domain comprises any mutation recited in Table 1, Table 2, FIG. 6A, FIG. 13A, FIG. 13B, FIG. 14, and/or FIG. 15. In certain embodiments, the mutation is selected from the group consisting of M883Y, S885N, S885T, T887E, H1064K, and N1065F as relating to SEQ ID NO:7. In certain embodiments, the mutation is M883Y as relating to SEQ ID NO:7. In certain embodiments, the mutation is S885N as relating to SEQ ID NO:7. In certain embodiments, the mutation is S885T as relating to SEQ ID NO:7. In certain embodiments, the mutation is T887E as relating to SEQ ID NO:7. In certain embodiments, the mutation is H1064K as relating to SEQ ID NO:7. In certain embodiments, the mutation is N1065F as relating to SEQ ID NO:7. In certain embodiments, the FcRn binding domain comprises at least one mutation selected from the group consisting of S885N, M883Y, M883Y/S885T/T887E, and H1064K/N1065F as relating to SEQ ID NO:7.

In certain embodiments, the ENPP1 polypeptide comprises at least one mutation selected from the group consisting of C25N, K27T, V29N, C25N/K27T, K369N, I371T, K369N/I371T, P534N, V536T, R545T, P554L, E592N, R741D, S766N, P534N/V536T, P554L/R545T, E592N/R741D, E864N, L866T, E864N/L866T, M883Y, S885N, S885T, T887E, H1064K, N1065F, M883Y/S885T/T887E, H1064K/N1065F as relating to SEQ ID NO:7.

In certain embodiments, the polypeptide comprises at least one mutation selected from the group consisting of S885N, S766N, M883Y/S885T/T887E, E864N/L866T, P534N/V536T/H1064K/N1065F, P554L/R545T, S766N/H1064K/N1065F, E592N/H1064K/N1065F, and P534N/V536T/M883Y/S885T/T887E as relating to SEQ ID NO:7.

In certain embodiments, the polypeptide comprises an ENPP1 polypeptide and an FcRn binding domain, the polypeptide comprising mutations M883Y, S885T, and T887E as relating to SEQ ID NO:7.

In certain embodiments, the polypeptide comprises an ENPP1 polypeptide and an FcRn binding domain, the polypeptide comprising mutations P534N, V536T, M883Y, S885T, and T887E as relating to SEQ ID NO:7.

In certain embodiments, the polypeptide comprises an ENPP1 polypeptide and an FcRn binding domain, the polypeptide comprising mutations E592N, H1064K, and N1065F as relating to SEQ ID NO:7.

In certain embodiments, the polypeptide comprises an ENPP1 mutant polypeptide, wherein the mutant polypeptide comprises an ENPP1 mutation selected from the group consisting of S766N, P534N, V536T, P554L, R545T, and E592N as relating to SEQ ID NO:7.

In certain embodiments, the ENPP1 mutant polypeptide comprises at least one mutation selected from the group consisting of S766N, P534N/V536T, P554L/R545T, and E592N as relating to SEQ ID NO:7.

In certain embodiments, the polypeptide further comprises an FcRn binding domain of an IgG.

In certain embodiments, the polypeptide comprises mutations selected from the group consisting of: S885N, S766N, M883Y/S885T/T887E, P534N/V536T/H1064K/N1065F, P554L/R545T, S766N/H1064K/N1065F, E592N/H1064K/N1065F, and P534N/V536T/M883Y/S885T/T887E as relating to SEQ ID NO:7.

In certain embodiments, the polypeptide comprises an S885N mutation in the FcRn binding domain as relating to SEQ ID NO:7.

In certain embodiments, the polypeptide comprises an S766N mutation in the ENPP1 mutant polypeptide as relating to SEQ ID NO:7.

In certain embodiments, the polypeptide comprises mutations M883Y, S885T, and T887E in the FcRn binding domain as relating to SEQ ID NO:7.

In certain embodiments, the polypeptide comprises mutations P534N and V536T in the ENPP1 mutant polypeptide and mutations H1064K and N1065F in the FcRn binding domain as relating to SEQ ID NO:7.

In certain embodiments, the polypeptide comprises mutations P554L and R545T in the ENPP1 mutant polypeptide as relating to SEQ ID NO:7.

In certain embodiments, the polypeptide comprises mutation S766N in the ENPP1 mutant polypeptide and mutations H1064K and N1065F in the FcRn binding domain as relating to SEQ ID NO:7.

In certain embodiments, the polypeptide comprises mutation E592N in the ENPP1 mutant polypeptide and mutations H1064K and N1065F in the FcRn binding domain as relating to SEQ ID NO:7.

In certain embodiments, the polypeptide comprises mutations P534N and V536T in the ENPP1 mutant polypeptide and mutations M883Y, S885T and T887E in the FcRn binding domain as relating to SEQ ID NO:7.

In certain embodiments, the ENPP1 polypeptide lacks a nuclease domain. In other embodiments, the ENPP1 polypeptide is truncated to remove the nuclease domain. In yet other embodiments, the ENPP1 polypeptide is truncated to remove the nuclease domain from about residue 524 to about residue 885 relative to SEQ ID NO:1, leaving only the catalytic domain from about residue 186 to about residue 586 relative to SEQ ID NO:1, which serves to preserve the catalytic activity of the protein.

In certain embodiments, the ENPP1 polypeptide is modified with a segment of the extracellular region of ENPP1 containing a peptidase cleavage site after the signal peptide, and between the transmembrane and extracellular domain, as compared to SEQ ID NO:1.

In certain embodiments, the ENPP1 polypeptide is modified with a segment of the extracellular region of ENPP1 containing a furin cleavage site between the transmembrane and extracellular domain, as compared to SEQ ID NO:1. In other embodiments, the ENPP1 polypeptide is not modified with a segment of the extracellular region of ENPP1 containing a furin cleavage site between the transmembrane and extracellular domain, as compared to SEQ ID NO:1.

In certain embodiments, the ENPP1 polypeptide is modified with a segment of the extracellular region of ENPP2 containing a signal peptidase cleavage site, as compared to SEQ ID NO:1. In other embodiments, the ENPP1 polypeptide is not modified with a segment of the extracellular region of ENPP2 containing a signal peptidase cleavage site, as compared to SEQ ID NO:1.

In certain embodiments, the polypeptide is soluble. In other embodiments, the polypeptide is a recombinant polypeptide. In yet other embodiments, the polypeptide comprises an ENPP1 polypeptide that lacks the ENPP1 transmembrane domain. In yet other embodiments, the polypeptide comprises an ENPP1 polypeptide wherein the ENPP1 transmembrane domain has been removed (and/or truncated) and replaced with the transmembrane domain of another polypeptide, such as, by way of non-limiting example, ENPP2, ENPP5, or ENPP7.

In certain embodiments, the polypeptide comprises a signal peptide resulting in the secretion of a precursor of the ENPP1 polypeptide, which undergoes proteolytic processing to yield a polypeptide comprising the ENPP1 polypeptide. In other embodiments, the signal peptide is selected from the group consisting of signal peptides of ENPP2, ENPP5, and ENPP7. In yet other embodiments, the polypeptide comprises an ENPP1 polypeptide comprising transmembrane domains of ENPP1 and another polypeptide, such as, by way of non-limiting example, ENPP2. In yet other embodiments, the ENPP1 polypeptide comprises a cleavage product of a precursor ENPP1 polypeptide comprising an ENPP2 transmembrane domain. In yet other embodiments, the ENPP2 transmembrane domain comprises residues 12-30 of SEQ ID NO:7, which corresponds to IISLFTFAVGVNICLGFTA.

In certain embodiments, the ENPP1 polypeptide is C-terminally fused to the Fc domain of human immunoglobulin 1 (IgG1), human immunoglobulin 2 (IgG2), human immunoglobulin 3 (IgG3), and/or human immunoglobulin 4 (IgG4). In other embodiments, the ENPP1 polypeptide is N-terminally fused to the Fc domain of human immunoglobulin 1 (IgG1), human immunoglobulin 2 (IgG2), human immunoglobulin 3 (IgG3), and/or human immunoglobulin 4 (IgG4). In yet other embodiments, the presence of IgFc domain improves half-life, solubility, reduces immunogenicity, and increases the activity of the ENPP1 polypeptide.

In certain embodiments, the ENPP1 polypeptide is C-terminally fused to human serum albumin. Human serum albumin may be conjugated to ENPP1 protein through a chemical linker, including but not limited to naturally occurring or engineered disulfide bonds, or by genetic fusion to ENPP1, or a fragment and/or variant thereof.

In certain embodiments, the polypeptide is further pegylated (fused with a poly(ethylene glycol) chain).

In certain embodiments, the polypeptide has a $k_{cat}$ value for the substrate ATP greater than or equal to about 3.4 (±0.4) $s^{-1}$ $enzyme^{-1}$, wherein the $k_{cat}$ is determined by measuring the rate of hydrolysis of ATP for the polypeptide.

In certain embodiments, the polypeptide has a $K_M$ value for the substrate ATP less than or equal to about 2 μM, wherein the $K_M$ is determined by measuring the rate of hydrolysis of ATP for the polypeptide.

In certain embodiments, the polypeptide is formulated as a liquid formulation. In other embodiments, the invention provides a dry product form of a pharmaceutical composition comprising a therapeutic amount of a polypeptide of the invention, whereby the dry product is reconstitutable to a solution of the compound in liquid form.

The invention provides a kit comprising at least one polypeptide of the invention, or a salt or solvate thereof, and instructions for using the polypeptide within the methods of the invention.

In certain embodiments, the polypeptide lacks a negatively-charged bone-targeting sequence. In yet other embodiments, a polyaspartic acid domain (from about 2 to about 20 or more sequential aspartic acid residues) is a non-limiting example of a negatively-charged bone-targeting sequence. In other embodiments, the polypeptide has a negatively-charged bone-targeting sequence.

It will be understood that an ENPP1 polypeptide according to the invention includes not only the native human proteins, but also any fragment, derivative, fusion, conjugate or mutant thereof having ATP hydrolytic activity of the native protein. As used herein in this disclosure, the phrase "an ENPP1 polypeptide, mutant, or mutant fragment thereof" also includes any compound or polypeptide (such as, but not limited to, a fusion protein) comprising an ENPP1 polypeptide, mutant, or mutant fragment thereof. Fusion proteins according to the invention are considered biological equivalents of ENPP1, but are intended to provide longer half-life or greater potency due to increased in vivo biologic exposure, as judged by the "area under the curve" (AUC) or increased half-life in pharmacokinetic experiments.

Vectors and Cells

The invention further provides an autonomously replicating or an integrative mammalian cell vector comprising a recombinant nucleic acid encoding a polypeptide of the invention. In certain embodiments, the vector comprises a plasmid or a virus. In other embodiments, the vector comprises a mammalian cell expression vector. In yet other embodiments, the vector further comprises at least one nucleic acid sequence that directs and/or controls expression of the polypeptide. In yet other embodiments, the recombinant nucleic acid encodes a polypeptide comprising an ENPP1 polypeptide of the invention and to a signal peptide, wherein the polypeptide is proteolytically processed upon secretion from a cell to yield the ENPP1 polypeptide of the invention.

In yet another aspect, the invention provides an isolated host cell comprising a vector of the invention. In certain embodiments, the cell is a non-human cell. In other embodiments, the cell is mammalian. In yet other embodiments, the vector of the invention comprises a recombinant nucleic acid encoding a polypeptide comprising a ENPP1 polypeptide of the invention and a signal peptide. In yet other embodiments, the polypeptide is proteolytically processed upon secretion from a cell to yield the ENPP1 polypeptide of the invention.

Cloning and Expression of ENPP1

ENPP1, or a ENPP1 polypeptide, is prepared as described in US 2015/0359858 A1, which is incorporated herein in its entirety by reference. ENPP1 is a transmembrane protein localized to the cell surface with distinct intramembrane domains. In order to express ENPP1 as a soluble extracellular protein, the transmembrane domain of ENPP1 may be swapped for the transmembrane domain of ENPP2, which results in the accumulation of soluble, recombinant ENPP1 in the extracellular fluid of the baculovirus cultures.

Signal sequences of any other known proteins may be used to target the extracellular domain of ENPP1 for secretion as well, such as but not limited to the signal sequence of the immunoglobulin kappa and lambda light chain proteins. Further, the invention should not be construed to be limited to the polypeptides described herein, but also includes polypeptides comprising any enzymatically active truncation of the ENPP1 extracellular domain.

ENPP1 is made soluble by omitting the transmembrane domain. Human ENPP1 (SEQ ID NO:1) was modified to express a soluble, recombinant protein by replacing its transmembrane region (e.g., residues 77-98) with the corresponding subdomain of human ENPP2 (NCBI accession NP_00112433 5, e.g., residues 12-30). The modified ENPP1 sequence was cloned into a modified pFastbac FIT vector possessing a TEV protease cleavage site followed by a C-terminus 9-F1lS tag, and cloned and expressed in insect cells, and both proteins were expressed in a baculovirus system as described previously (Albright, et al., 2012, Blood 120:4432-4440; Saunders, et al., 2011, J. Biol. Chem. 18:994-1004; Saunders, et al., 2008, Mol. Cancer Ther. 7:3352-3362), resulting in the accumulation of soluble, recombinant protein in the extracellular fluid.

Production and Purification of ENPP1 and ENPP1 Fusion Proteins

In certain embodiments, a soluble ENPP1 polypeptide, including IgG Fc domain or enzymatically/biologically active fragments thereof, are efficacious in treating, reducing, and/or preventing progression of diseases or disorders contemplated herein. In other embodiments, the soluble ENPP1 polypeptide does not include a bone targeting domain, such as 2-20 consecutive polyaspartic acid residues or 2-20 consecutive polyglutamic acid residues.

To produce soluble, recombinant ENPP1 for in vitro use, ENPP1 was fused to the Fc domain of IgG (referred to as "NPP1-Fc") and the fusion protein was expressed in stable CHO cell lines. The protein can also be expressed from HEK293 cells, Baculovirus insect cell system or CHO cells or Yeast *Pichia* expression system using suitable vectors. The protein can be produced in either adherent or suspension cells. Preferably the fusion protein is expressed in CHO cells. To establish stable cell lines the nucleic acid sequence encoding ENPP1 constructs are cloned into an appropriate vector for large scale protein production.

Many expression systems are known can be used for the production of ENPP1 fusion protein, including bacteria (for example *E. coli* and *Bacillus subtilis*), yeasts (for example *Saccharomyces cerevisiae, Kluyveronmyces lactis* and *Pichia pastoris*), filamentous fungi (for example *Aspergillus*), plant cells, animal cells and insect cells. The desired protein can be produced in conventional ways, for example from a coding sequence inserted in the host chromosome or on a free plasmid.

The yeasts can be transformed with a coding sequence for the desired protein in any of the usual ways, for example electroporation. Methods for transformation of yeast by electroporation are disclosed in Becker & Guarente, 1990, Methods Enzymol. 194: 182. Successfully transformed cells, i.e., cells that contain a DNA construct of the present invention, can be identified by well-known techniques. For example, cells resulting from the introduction of an expression construct can be grown to produce the desired polypeptide. Cells can be harvested and lysed and their DNA content examined for the presence of the DNA using a method, such as that described by Southern, 1975, J. Mol. Biol, 98:503 and/or Berent, et al., 1985, Biotech 3:208. Alternatively, the presence of the protein in the supernatant can be detected using antibodies.

Useful yeast plasmid vectors include pRS403-406 and pRS413-416 and are generally available fron1 Strat:1.gene Cloning Systems, La Jolla, CA, USA Plasmids pRS403, pRS404, pRS405 and pRS406 are Yeast Integrating plasmids (Y1ps) and incorporate the yeast selectable markers I-11S3, TRP1, LEU2 and 1JRA3. Plasmids pRS413-416 are Yeast Centromere plasmids (YCps).

A variety of methods have been developed to operably link DNA to vectors via complementary cohesive termini. For instance, complementary homopolymer tract can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion, is treated with bacteriophage T4 DNA polymerase or *E. coli* DNA polymerase I, which are enzymes that remove protruding, 3'-single-stranded termini with their 3'-5'-exonucleolytic activities, and fill in recessed 3'-ends with their polymerizing activities.

The combination of these activities thus generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Clones of single, stably transfected cells are then established and screened for high expressing clones of the desired fusion protein. Screening of the single cell clones for ENPP3 protein expression can be accomplished in a high-throughput manner in 96 well plates using the synthetic enzymatic substrate pNP-TMP as previously described (Albright, et al., 2015, Nat. Commun. 6:10006). Upon identification of high expressing clones through screening, protein production can be accomplished in shaking flasks or bio-reactors are previously described in Albright, et al., 2015, Nat. Commun. 6:10006.

Purification of ENPP1 can be accomplished using a combination of standard purification techniques known in the art. Examples of which are described above in production of ENPP3 protein. Following purification, ENPP1-Fc was dialyzed into PBS supplemented with $Zn^{2+}$ and $Mg^{2+}$ (PBSplus) concentrated to between 5 and 7 mg/ml, and frozen at −80° C. in aliquots of 200-500 µl. Aliquots were thawed immediately prior to use and the specific activity of the solution was adjusted to 31.25 au/ml (or about 0.7 mg/ml depending on the preparation) by dilution in PBSplus.

SEQUENCES

SEQ ID NO: 1: hENPP1 Amino Acid Sequence
MERDGCAGGGSRGGEGGRAPREGPAGNGRDRGRSHAAEAPGDPQAAASLLAPMDVGEEPLEKAARART
AKDPNTYKVLSLVLSVCVLTTILGCIFGLKPSCAKEVKSCKGRCFERTFGNCRCDAACVELGNCCLDY
QETCIEPEHIWTCNKFRCGEKRLTRSLCACSDDCKDKGDCCINYSSVCQGEKSWVEEPCESINEPQCP
AGFETPPTLLFSLDGFRAEYLHTWGGLLPVISKLKKCGTYTKNMRPVYPTKTFPNHYSIVTGLYPESH
GIIDNKMYDPKMNASFSLKSKEKFNPEWYKGEPIWVTAKYQGLKSGTFFWPGSDVEINGIFPDIYKMY
NGSVPFEERILAVLQWLQLPKDERPHFYTLYLEEPDSSGHSYGPVSSEVIKALQRVDGMVGMLMDGLK
ELNLHRCLNLILISDHGMEQGSCKKYIYLNKYLGDVKNIKVIYGPAARLRPSDVPDKYYSFNYEGIAR
NLSCREPNQHFKPYLKHFLPKRLHFAKSDRIEPLTFYLDPQWQLALNPSERKYCGSGFHGSDNVFSNM
QALFVGYGPGFKHGIEADTFENIEVYNLMCDLLNLTPAPNNGTHGSLNHLLKNPVYTPKHPKEVHPLV
QCPFTRNPRDNLGCSCNPSILPIEDFQTQFNLTVAEEKIIKHETLPYGRPRVLQKENTICLLSQHQFM
SGYSQDILMPLWTSYTVDRNDSFSTEDFSNCLYQDFRIPLSPVHKCSFYKNNTKVSYGFLSPPQLNKN
SSGIYSEALLTTNIVPMYQSFQVIWRYFHDTLLRKYAEERNGVNVVSGPVFDFDYDGRCDSLENLRQK
RRVIRNQEILIPTHFFIVLTSCKDTSQTPLHCENLDTLAFILPHRTDNSESCVHGKHDSSWVEELLML
HRARITDVEHITGLSFYQQRKEPVSDILKLKTHLPTFSQED SEQ ID NO: 2: ENPP2 Amino Acid Sequence
MARRSSFQSCQIISLFTFAVGVNICLGFTAHRIKRAEGWEEGPPTVLSDSPWTNISGSCKGRCFELQE
AGPPDCRCDNLCKSYTSCCHDFDELCLKTARGWECTKDRCGEVRNEENACHCSEDCLARGDCCTNYQV
VCKGESHWVDDDCEEIKAAECPAGFVRPPLIIFSVDGFRASYMKKGSKVMPNIEKLRSCGTHSPYMRP
VYPTKTFPNLYTLATGLYPESHGIVGNSMYDPVFDATFHLRGREKFNHRWWGGQPLWITATKQGVKAG
TFFWSVVIPHERRILTILQWLTLPDHERPSVYAFYSEQPDFSGHKYGPFGPEMTNPLREIDKIVGQLM
DGLKQLKLHRCVNVIFVGDHGMEDVTCDRTEFLSNYLTNVDDITLVPGTLGRIRSKFSNNAKYDPKAI
IANLTCKKPDQHFKPYLKQHLPKRLHYANNRRIEDIHLLVERRWHVARKPLDVYKKPSGKCFFQGDHG

SEQUENCES

FDNKVNSMQTVFVGYGSTFKYKTKVPPFENIELYNVMCDLLGLKPAPNNGTHGSLNHLLRTNTFRPTM
PEEVTRPNYPGIMYLQSDFDLGCTCDDKVEPKNKLDELNKRLHTKGSTEAETRKFRGSRNENKENING
NFEPRKERHLLYGRPAVLYRTRYDILYHTDFESGYSEIFLMPLWTSYTVSKQAEVSSVPDHLTSCVRP
DVRVSPSFSQNCLAYKNDKQMSYGFLFPPYLSSSPEAKYDAFLVTNMVPMYPAFKRVWNYFQRVLVKK
YASERNGVNVISGPIFDYDYDGLHDTEDKIKQYVEGSSIPVPTHYYSIITSCLDFTQPADKCDGPLSV
SSFILPHRPDNEESCNSSEDESKWVEELMKMHTARVRDIEHLTSLDFFRKTSRSYPEILTLKTYLHTY
ESEI

SEQ ID NO: 3 hIgG Fc domain, Fc
DKTHTCPPCPAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQVYTLPPSRE
EMTKNQVSLTCLVKGFYPSDIAVEWESNGQPENNYKTTPPVLDSDGSFFLYSKLTVDKSRWQQGNVFS
CSVMHEALHNHYTQKSLSLSPGK SEQ ID NO: 4: hENPP5 protein export signal sequence
MTSKFLLVSFILAALSLSTTFS-Xaa$_{23}$Xaa$_{24}$,
wherein Xaa$_{23}$ is absent or L, and
wherein Xaa$_{24}$ is absent if Xaa$_{23}$ is absent and Xaa$_{24}$ is absent or
Q if Xaa$_{23}$ is L SEQ ID NO: 5: hENPP7 protein export signal sequence
MRGPAVLLTV ALATLLAPGA GA SEQ ID NO: 6: hENPP7 protein export signal sequence
MRGPAVLLTV ALATLLAPGA SEQ ID NO: 7: ENPP1-Fc
MRGPAVLLTVALATLLAPGAGAPSCAKEVKSCKGRCFERTEGNCRCDAACVELGNCCLDYQE
TCIEPEHIWTCNKFRCGEKRLTRSLCACSDDCKDKGDCCINYSSVCQGEKSWVEEPCESINE
PQCPAGFETPPTLLFSLGDFRAEYLHTWGGLLPVISKLKKCGTYTKNMRPVYPTKTFPNHYS
IVTGLYPESHGIIDNKMYDPKMNASFSLKSKEKFNPEWYKGEPIWVTAKYQGLKSGTFFWPG
SDVEINGIFPDIYKMYNGSVPFEERILAVLQWLQLPKDERPHFYTLYLEEPDSSGHSYGPVS
SEVIKALQRVDGMVGMLMDGLKELNLHRCLNLILISDHGMEQGSCKKYIYLNKYLGDVKNIK
VIYGPAARLRPSDVPDKYYSFNYEGIARNLSCREPNQHFKPYLKHFLPKRLHFAKSDRIEPL
TFYLDPQWQLALNPSERKYCGSGFHGSDNVFSNMQALFVGYGPGFKHGIEADTFENIEVYNL
MCDLLNLTPAPNNGTHGSLNHLLKNPVYTPKHPKEVHPLVQCPFTRNPRDNLGCSCNPSILP
IEDFQTQFNLTVAEEKIIKHETLPYGRPRVLQKENTICLLSQHQFMSGYSQDILMPLWTSYT
VDRNDSFSTEDFSNCLYQDFRIPLSPVHKCSFYKNNTKVSYGFLSPPQLNKNSSGIYSEALL
TTNIVPMYQSFQVIWRYFHDTLLRKYAEERNGVNVVSGPVFDFDYDGRCDSLENLRQKRRVI
RNQEILIPTHFFIVLTSCKDTSQTPLHCENLDTLAFILPHRTDNSESCVHGKHDSSWVEELL
MLHRARITDVEHITGLSFYQQRKEPVSDILKLKTHLPTFSQED*RSDKTHTCPPCPAPELLGG
PSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVF
SCSVMHEALHNHYTQKSLSLSPGK*

Bold: signal sequence
Regular: ENPP1 extracellular domain
Underlined: linker sequence
Italics: Fc domain

Methods

The invention includes a method of reducing or preventing progression of pathological calcification in a subject in need thereof, the method comprising administering to the subject a therapeutically effective amount of a polypeptide of the invention.

The invention further includes a method of reducing or preventing progression of pathological ossification in a subject in need thereof, the method comprising administering to the subject a therapeutically effective amount of a polypeptide of the invention.

The invention further includes a method of reducing or preventing progression of ectopic calcification of soft tissue, including reducing, ameliorating, or preventing vascular calcification, in a subject in need thereof, the method comprising administering to the subject a therapeutically effective amount of a polypeptide of the invention.

The invention further includes a method of reducing or preventing progression of diseases caused by ENPP1 deficiency. ENPP1 deficiency is characterized by reduced levels of ENPP1 activity and or defective expression of ENPP1 levels (compared to that of ENPP1 activity levels or ENPP1 expression levels respectively in normal healthy subjects) in a subject in need thereof, the method comprising administering to the subject a therapeutically effective amount of a polypeptide of the invention.

The invention further includes a method of reducing or preventing progression of diseases caused by lower levels of plasma PPi in a subject in need thereof, the method comprising administering to the subject a therapeutically effective amount of the polypeptides of the invention to increase the plasma PPi of the subjects to normal (1-3 μM) or above (30-50% higher than) normal levels and then to maintain the plasma PPi at a constant normal or above normal level thereafter. The method further comprises administering additional therapeutic effective amounts at intervals of two days, three days, one week or one month in order to maintain the Plasma PPi of the subject at a constant normal or above normal level to reduce or prevent the progression of pathological calcification or ossification.

The invention further includes a method of treating, reversing, or preventing progression of ossification of the posterior longitudinal ligament (OPLL) in a subject in need thereof, the method comprising administering to the subject a therapeutically effective amount of a polypeptide of the invention.

The invention further includes a method of treating, reverting, or preventing progression of hypophosphatemic rickets in a subject in need thereof, the method comprising administering to the subject a therapeutically effective amount of a polypeptide of the invention.

The invention further includes a method of reducing or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of a polypeptide of the invention.

The invention further includes a method of reducing or preventing progression of aging related hardening of arteries in a subject in need thereof, the method comprising administering to the subject a therapeutically effective amount of a polypeptide of the invention.

The invention further includes a method of reducing or preventing progression of a disease caused by ENPP1 deficiency (for example, reduced levels of ENPP1 activity and/or defective expression of ENPP1 levels, as compared to that of ENPP1 activity levels or ENPP1 expression levels, respectively, in normal healthy subjects) in a subject in need thereof, the method comprising administering to the subject a therapeutically effective amount of a polypeptide of the invention.

The invention further includes a method of reducing or preventing progression of a disease caused by lower than normal levels of plasma PPi in a subject in need thereof, the method comprising administering to the subject a therapeutically effective amount of a polypeptide of the invention to increase and/or sustain the plasma PPi of the subjects to a level that is about 90%, 95%, 100%, 105%, 110%, 120%, 130%, 140%, or 150% of the normal PPi level (about 1-3 µM). In certain embodiments, the method further comprises further administration of the polypeptide of the invention every two days, three days, one week, or one month in order to maintain the plasma PPi levels at a level that is about 90%, 95%, 100%, 105%, 110%, 120%, 130%, 140%, or 150% of the normal PPi level, thus preventing the progression of pathological calcification or ossification.

The invention further includes a method of treating, reversing, or preventing progression of Pseudoxanthoma Elasticum (PXE) in a subject in need thereof, the method comprising administering to the subject a therapeutically effective amount of a polypeptide of the invention.

The invention further includes a method of treating, reversing, or preventing progression of calcification of atherosclerotic plaques in vascular arteries in a subject in need thereof, the method comprising administering to the subject a therapeutically effective amount of a polypeptide of the invention.

The invention further includes a method of treating, reversing, or preventing progression of osteoarthritis in a subject in need thereof, the method comprising administering to the subject a therapeutically effective amount of a polypeptide of the invention.

The invention further includes a method of treating, reversing, or preventing progression of hardening of arteries due to progeria in a subject in need thereof, the method comprising administering to the subject a therapeutically effective amount of a polypeptide of the invention.

The invention further includes a method of treating, reversing, or preventing progression of X-linked hypophosphatemic rickets (XLH), hereditary hypophosphatemic rickets (HHRH), hypophosphatemic bone disease (HBD), autosomal dominant hypophosphatemic rickets (ADHR), and/or and autosomal recessive hypophosphatemic rickets in a subject in need thereof, the method comprising administering to the subject a therapeutically effective amount of a polypeptide of the invention.

The invention further includes a method of treating, reversing, or preventing progression of age-related osteopenia in a subject in need thereof, the method comprising administering to the subject a therapeutically effective amount of a polypeptide t of the invention.

The invention further includes a method of treating, reversing, or preventing progression of ankylosing spondylitis in a subject in need thereof, the method comprising administering to the subject a therapeutically effective amount of a polypeptide of the invention.

The invention further includes a method of treating, reversing, or preventing progression of strokes in pediatric sickle cell anemia in a subject in need thereof, the method comprising administering to the subject a therapeutically effective amount of a polypeptide of the invention.

In certain embodiments, the pathological calcification is selected from the group consisting of idiopathic infantile arterial calcification (IIAC) and calcification of atherosclerotic plaques.

In certain embodiments, the pathological ossification is selected from the group consisting of ossification of the posterior longitudinal ligament (OPLL), hypophosphatemic rickets, and osteoarthritis.

In certain embodiments, the soft tissue calcification is selected from the group consisting of IIAC and osteoarthritis. In other embodiments, the soft tissue comprises atherosclerotic plaques. In yet other embodiments, the soft tissue comprises muscular arteries. In yet other embodiments, the soft tissue is selected from the group consisting of joint and spine. In yet other embodiments, the joint is selected from the group consisting of joints of the hands and joints of the feet. In yet other embodiments, the soft tissue is selected from the group consisting of articular cartilage and vertebral disk cartilage. In yet other embodiments, the soft tissue comprises vessels. In yet other embodiments, the soft tissue comprises connective tissue.

In certain embodiments, the subject is diagnosed with progeria.

In certain embodiments, the polypeptide of the invention is a secreted product of a ENPP1 precursor protein expressed in a mammalian cell. In other embodiments, the ENPP1 precursor protein comprises a signal peptide sequence and an ENPP1 polypeptide, wherein the ENPP1 precursor protein undergoes proteolytic processing to the polypeptide of the invention. In yet other embodiments, in the ENPP1 precursor protein the signal peptide sequence is conjugated to the ENPP1 polypeptide N-terminus. Upon proteolysis, the signal sequence is cleaved from the ENPP1 precursor protein to provide the ENPP1 polypeptide. In certain embodiments, the signal peptide sequence is selected from the group consisting of ENPP1 signal peptide sequence, ENPP2 signal peptide sequence, ENPP7 signal peptide sequence, and ENPP5 signal peptide sequence.

In certain embodiments, the polypeptide is administered acutely or chronically to the subject. In other embodiments, the polypeptide is administered locally, regionally, parenterally or systemically to the subject In certain embodiments, the subject is a mammal. In other embodiments, the mammal is human.

In certain embodiments, the polypeptide, or its precursor protein, is administered by at least one route selected from the group consisting of subcutaneous, oral, aerosol, inhalational, rectal, vaginal, transdermal, subcutaneous, intranasal, buccal, sublingual, parenteral, intrathecal, intragastrical, ophthalmic, pulmonary and topical. In other embodiments, the polypeptide, or its precursor protein, is administered to the subject as a pharmaceutical composition further comprising at least one pharmaceutically acceptable carrier.

In certain embodiments, the polypeptide, or its precursor protein, is administered acutely or chronically to the subject. In other embodiments, the polypeptide, or its precursor protein, is administered locally, regionally or systemically to the subject. In yet another embodiment, the polypeptide, or its precursor protein, is delivered on an encoded vector, wherein the vector encodes the protein and it is transcribed and translated from the vector upon administration of the vector to the subject.

It will be appreciated by one of skill in the art, when armed with the present disclosure including the methods detailed herein, that the invention is not limited to treatment of a disease or disorder once it is established. Particularly, the symptoms of the disease or disorder need not have manifested to the point of detriment to the subject; indeed, the disease or disorder need not be detected in a subject before treatment is administered. That is, significant pathology from disease or disorder does not have to occur before the present invention may provide benefit.

Thus, the present invention, as described more fully herein, includes a method for preventing diseases and disorders in a subject, in that a polypeptide of the invention, as discussed elsewhere herein, can be administered to a subject prior to the onset of the disease or disorder, thereby preventing the disease or disorder from developing. Particularly, where the symptoms of the disease or disorder have not manifested to the point of detriment to the subject; indeed, the disease or disorder need not be detected in a subject before treatment is administered. That is, significant pathology from the disease or disorder does not have to occur before the present invention may provide benefit. Therefore, the present invention includes methods for preventing or delaying onset, or reducing progression or growth, of a disease or disorder in a subject, in that a polypeptide of the invention can be administered to a subject prior to detection of the disease or disorder. In certain embodiments, the polypeptide of the invention is administered to a subject with a strong family history of the disease or disorder, thereby preventing or delaying onset or progression of the disease or disorder.

Armed with the disclosure herein, one skilled in the art would thus appreciate that the prevention of a disease or disorder in a subject encompasses administering to a subject a polypeptide of the invention as a preventative measure against the disease or disorder.

Pharmaceutical Compositions and Formulations

The invention provides pharmaceutical compositions comprising a polypeptide of the invention within the methods described herein.

Such a pharmaceutical composition is in a form suitable for administration to a subject, or the pharmaceutical composition may further comprise one or more pharmaceutically acceptable carriers, one or more additional ingredients, or some combination of these. The various components of the pharmaceutical composition may be present in the form of a physiologically acceptable salt, such as in combination with a physiologically acceptable cation or anion, as is well known in the art.

In an embodiment, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 500 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between about 0.1% and about 100% (w/w) active ingredient.

Pharmaceutical compositions that are useful in the methods of the invention may be suitably developed for inhalational, oral, rectal, vaginal, parenteral, topical, transdermal, pulmonary, intranasal, buccal, ophthalmic, intrathecal, intravenous or another route of administration. Other contemplated formulations include projected nanoparticles, liposomal preparations, resealed erythrocytes containing the active ingredient, and immunologically-based formulations. The route(s) of administration is readily apparent to the skilled artisan and depends upon any number of factors including the type and severity of the disease being treated, the type and age of the veterinary or human patient being treated, and the like.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Administration/Dosing

The regimen of administration may affect what constitutes an effective amount. For example, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation. In certain embodiments, administration of the compound of the invention to a subject elevates the subject's plasma PPi to a level that is close to normal, where a normal level of PPi in mammals is 1-3 µM. "Close to normal" refers to 0 to 1.2 µM or 0-40% below or above normal, 30 nM to 0.9 µM or 1-30% below or above normal, 0 to 0.6 μM or 0-20% below or above normal, or 0 to 0.3 μM or 0-10% below or above normal.

Administration of the compositions of the present invention to a patient, such as a mammal, such as a human, may be carried out using known procedures, at dosages and for periods of time effective to treat a disease or disorder in the patient. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. Dosage is determined based on the biological activity of the therapeutic compound which in turn depends on the half-life and the area under the plasma time of the therapeutic compound curve. The polypeptide according to the invention is administered at an appropriate time interval of every 2 days, or every 4 days, or every week or every month so as to achieve a continuous level of plasma PPi that is either close to the normal (1-3 μM) level or above (30-50% higher than) normal levels of PPi. Therapeutic dosage of the polypeptides of the invention may also be determined based on half-life or the rate at which the therapeutic polypeptide is cleared out of the body. The polypeptide according to the invention is administered at appropriate time intervals of either every 2 days, or every 4 days, every week or every month so as to achieve a constant level of enzymatic activity of ENPP1.

For example, several divided doses may be administered daily or the dose may be proportionally reduced as indicated by the exigencies of the therapeutic situation. A non-limiting example of an effective dose range for a therapeutic compound of the invention is from about 0.01 and 50 mg/kg of body weight/per day. In some embodiments, the effective dose range for a therapeutic compound of the invention is from about 50 ng to 500 ng/kg, preferably 100 ng to 300 ng/kg of bodyweight. One of ordinary skill in the art would be able to study the relevant factors and make the determination regarding the effective amount of the therapeutic compound without undue experimentation.

The compound can be administered to an patient as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon any number of factors, such as, but not limited to, the type and severity of the disease being treated, and the type and age of the patient.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In certain embodiments, the compositions of the invention are administered to the patient in dosages that range from one to five times per day or more. In other embodiments, the compositions of the invention are administered to the patient in range of dosages that include, but are not limited to, once every day, every two, days, every three days to once a week, and once every two weeks. The frequency of administration of the various combination compositions of the invention varies from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physical taking all other factors about the patient into account.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

Routes of Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. The formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Single unit dosage forms suitable for oral administration, such as tablets, capsules, gelcaps, and caplets, which are adapted for controlled-release are encompassed by the present invention.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form. For sustained release, the compounds may be formulated with a suitable polymer or hydrophobic material that provides sustained release properties to the compounds. As such, the compounds for use the method of the invention may be administered in the form of microparticles, for example, by injection or in the form of wafers or discs by implantation. In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that mat, although not necessarily, includes a delay of from about 10 minutes up to about 12 hours. The term pulsatile release is used herein in its conventional sense to refer to a drug formulation that provides release of the drug in such a way as to produce pulsed plasma profiles of the drug after drug administration. The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction and preparation conditions, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Methods and Materials

Unless specifically mentioned, expression of constructs in CHO cells or modified CHO cells with and without supplementation, $V_{max}$ Assay, $K_m/K_{at}$ Assay, AUC assay, half-life assay were carried out using protocols described elsewhere herein Generation of ENPP1-Fc Mutant Constructs Human NPP1 (Human: NCBI accession NP_006199) was modified to express soluble, recombinant protein was fused to IgG1 by sub cloning into pFUSE-hIgG1-Fc1 or pFUSE-mIgG1-Fc1 plasmids (InvivoGen, San Diego CA), respectively. The constructs were generated from SEQ ID NO:7) using site-directed mutagenesis using commercially available kits. (Q5® Site-Directed Mutagenesis Kit/New England Biolabs). The constructs thus generated were sequenced to verify the nucleic acid sequence and then used for expression of protein.

Expression of ENPP1-Fc Mutant Constructs

Stable transfections of the ENPP1-Fc constructs were established in CHO K1 cells (Sigma Aldrich, 85051005) under Zeocin/gentamycin selection, and were adapted for suspension growth. Adapted cells were used to seed liquid culture growths in CD FortiCHO™ medium (A1148301, Thermo Fischer) in shaker flasks at 37° C. and 5% $CO_2$, agitated at 120 rpm with high humidity. The culture was gradually expanded to the desired target volume and then maintained for another 2 days to accumulate extracellular protein Expression of ENPP1-Fc Mutant Constructs in Modified CHO Cells CHO-K1 cells were modified to generated CHO-K1-MOD cells stably expressing human α-2,6-sialytransferase (α-2,6-ST) enzyme. Stable transfections of the ENPP1-Fc constructs were established in CHO K1-MOD cells, and protein was expressed following the same protocol as described above. Optionally in some constructs, the cell culture medium of CHO-K1-MOD cells expressing the corresponding constructs were supplemented with sialic acid or a "high-flux" precursor of sialic acid called 1,3,4-O-Bu3ManNAc to facilitate higher levels of glycosylate during protein production Purification of ENPP1-Fc Mutant Constructs The liquid cultures were centrifuged at 4300×g for 5 mm and the supernatants were filtered through a 0.2 μm membrane and concentrated via tangential flow using a Pellicon® 3 0.0.11 m² Ultracell® 30 D cassette (Millipore, Billerica MA). The concentrated supernatant was then purified by a combination of chromatographic techniques in a multi-step process. These techniques are performed sequentially and may include any of the following: affinity chromatography with protein A or protein G, cation-exchange chromatography, anion-exchange chromatography, size exclusion chromatography, hydrophobic exchange chromatography, high-pressure liquid chromatography (HPLC), precipitation steps, extractions steps, lyophylizations steps, and/or crystallization steps. Using any one of these steps in series, one skilled in the art of protein chemistry can purify the compositions of matter described to homogeneity such that there are no contaminating protein bands on a silver stained gel. The resulting protein samples then tested with Pierce LAL Chromogenic Endotoxin Quantitation Kit (cat. 88282) to verify that all were free of endotoxin.

In order to quantitate the biological impact of clone optimization, the pharmacodynamics effects of select ENPP1-Fc isoforms were quantitated by determining plasma PPi concentrations at multiple time points following a single subcutaneous dose of each isoform.

$K_m/K_{cat}$ Determination

The steady state hydrolysis of ATP by ENPP1 constructs was determined by HPLC. Briefly, enzyme reactions were started by addition of 10 nM PPi to varying concentrations of ATP in the reaction buffer containing 20 mM Tris, pH 7.4, 150 mM NaCl, 4.5 nM KCl, 14 mM $ZnCl_2$, 1 mM $MgCl_2$, and 1 mM $CaCl_2$. At various time points, 50 μl reaction solution were removed and quenched with an equal volume of 3M formic acid. The quenched reaction solution was loaded on a C-18 (5 m t 250×4.6 mm) column (Higgins Analytical) equilibrated in 5 mM ammonium acetate (pH 6.0) solution and eluted with a 0% to 20% methanol gradient. Substrate and products were monitored by UV absorbance at 259 nm and quantified according to the integration of their correspondent peaks and standard curves.

$V_{max}$ Assay

For each of the mutants prepared, phosphodiesterase activity was analyzed using thymidine 5'-monophosphate p-nitrophenyl ester (pNP-TMP) (Saunders, et al., 2008, Mol. Cancer Ther. 7(10):3352-62; Albright, et al., 2015, Nat Commun. 6:10006).

Area Under the Curve Assay

The area under the plasma concentration versus time curve, also called the area under the curve (AUC) can be used as a means of evaluating the volume of distribution (V), total elimination clearance (CL), and bioavailability (F) for extravascular drug delivery. Area under plasma time curve for each expressed and purified ENPP1-Fc construct were carried out using the standard equation to determine half-life and bioavailability after a single subcutaneous injection of biologic, as described in Equation 1.

Half-Life Determination

The drug half-life ($t_{1/2}$) is the time it takes for the plasma concentration or the amount of drug or biologic in the body to be reduced by 50%. Half-life values for each expressed and purified ENPP1-Fc construct were carried out following protocols described in the prior art and/or herein, such as Equation 1, which allows for determining half-life and bioavailability after a single subcutaneous injection of biologic.

Drug half-life can be calculated using Equation 1, which correlates the relationship between systemic fractional concentration and time of a drug administered to a subcutaneous depot in a single injection. Plotting the data as fraction of drug absorbed (F) over time (t) allows for the determination of the elimination ($k_e$) and absorption ($k_a$) constants by fitting the data to the equation for the total systemic absorption of a drug administered at a subcutaneous depot at time t=0.

$$F = \frac{k_a}{(k_a - k_e)}[e^{-k_e t} - e^{-k_a t}] \qquad \text{(Equation 1)}$$

Example 1: Selection and Optimization of Glycosylation Mutations

A ENPP1-Fc construct was subjected to mutations so as to introduce putative additional glycosylation sites and/or increase affinity of the Fc for the neonatal orphan receptor (FcRn). Mutations tested are illustrated elsewhere herein, and specific Constructs of the discussion are illustrated below.

Figure 6A:
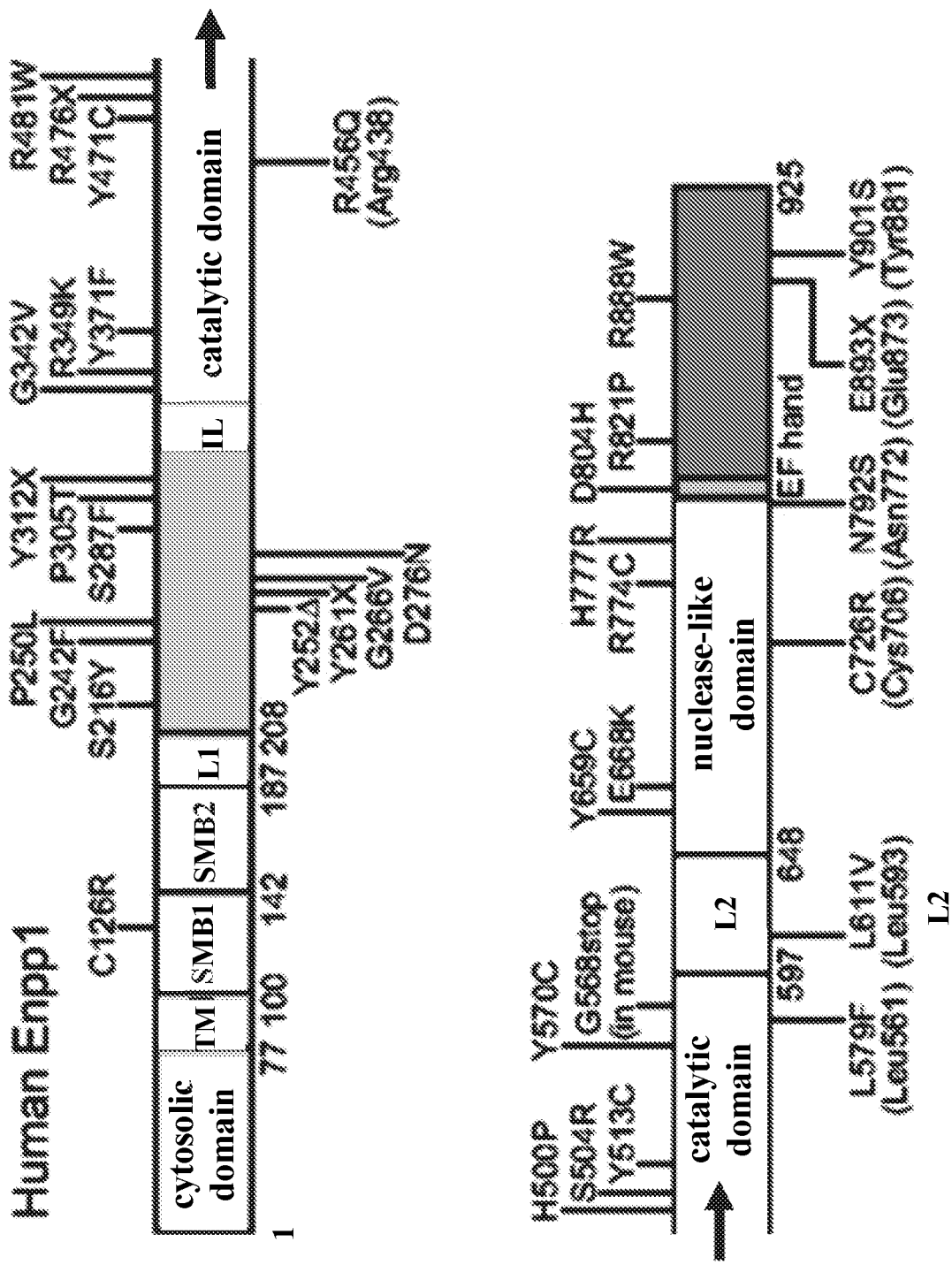
FIG. 6A illustrates certain domains of human ENPP1 with known loss of function mutations that result in the human disease "Generalized Arterial Calcification of Infancy" (GACI). In certain embodiments, glycosylation sites are not introduced near regions with known loss of function mutations that result in GACI (illustrated in FIG. 6A).
Figure 6B:
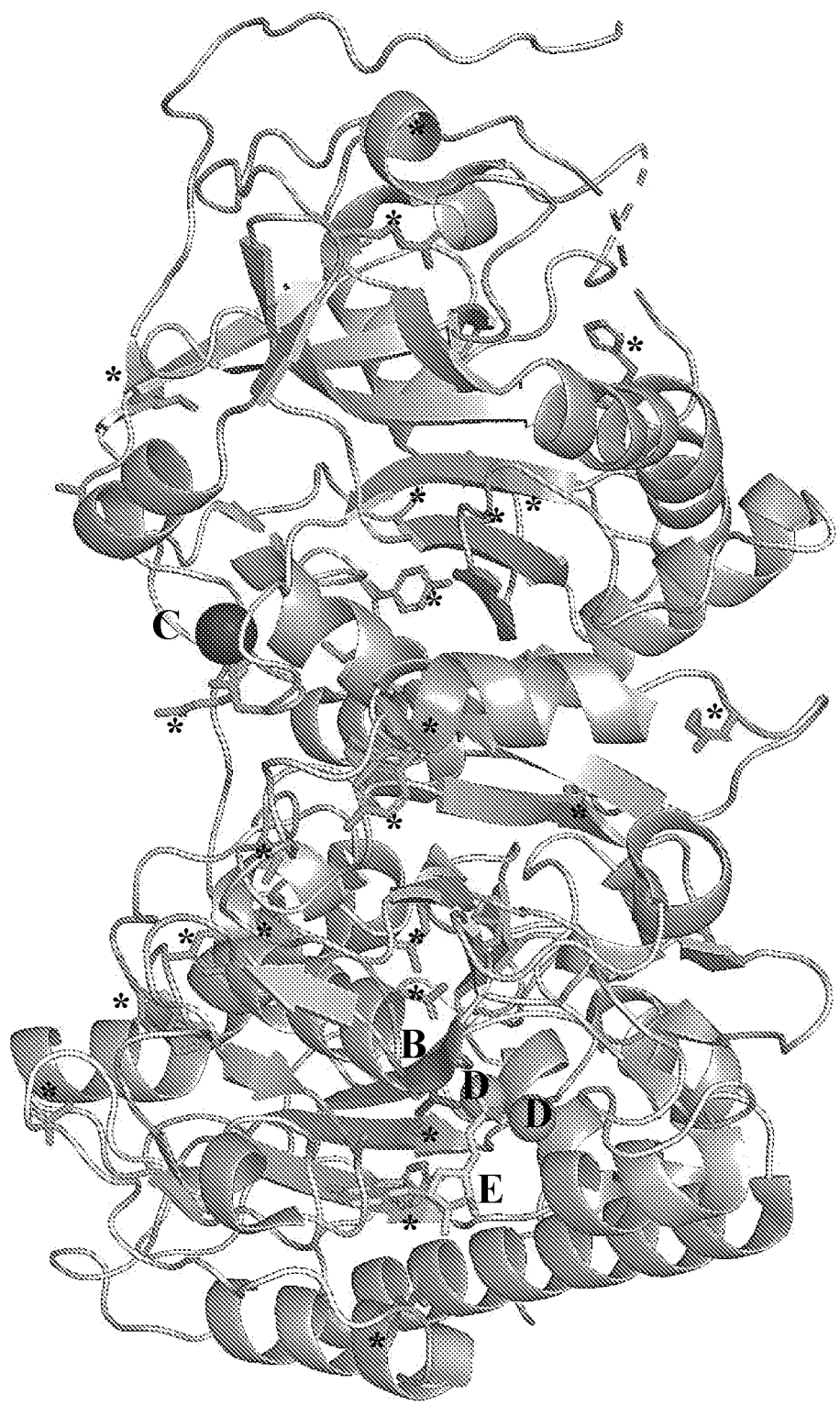
FIG. 6B illustrates the crystal structure of ENPP1, with residues where known loss of function mutations resulting in GACI are highlighted (and marked with *). The residue in (B) is located in the catalytic domain and corresponds to T238A. As in FIG. 5: calcium atom (C); 2 Zinc atoms (D); ATP molecule (E).
Figure 7A:
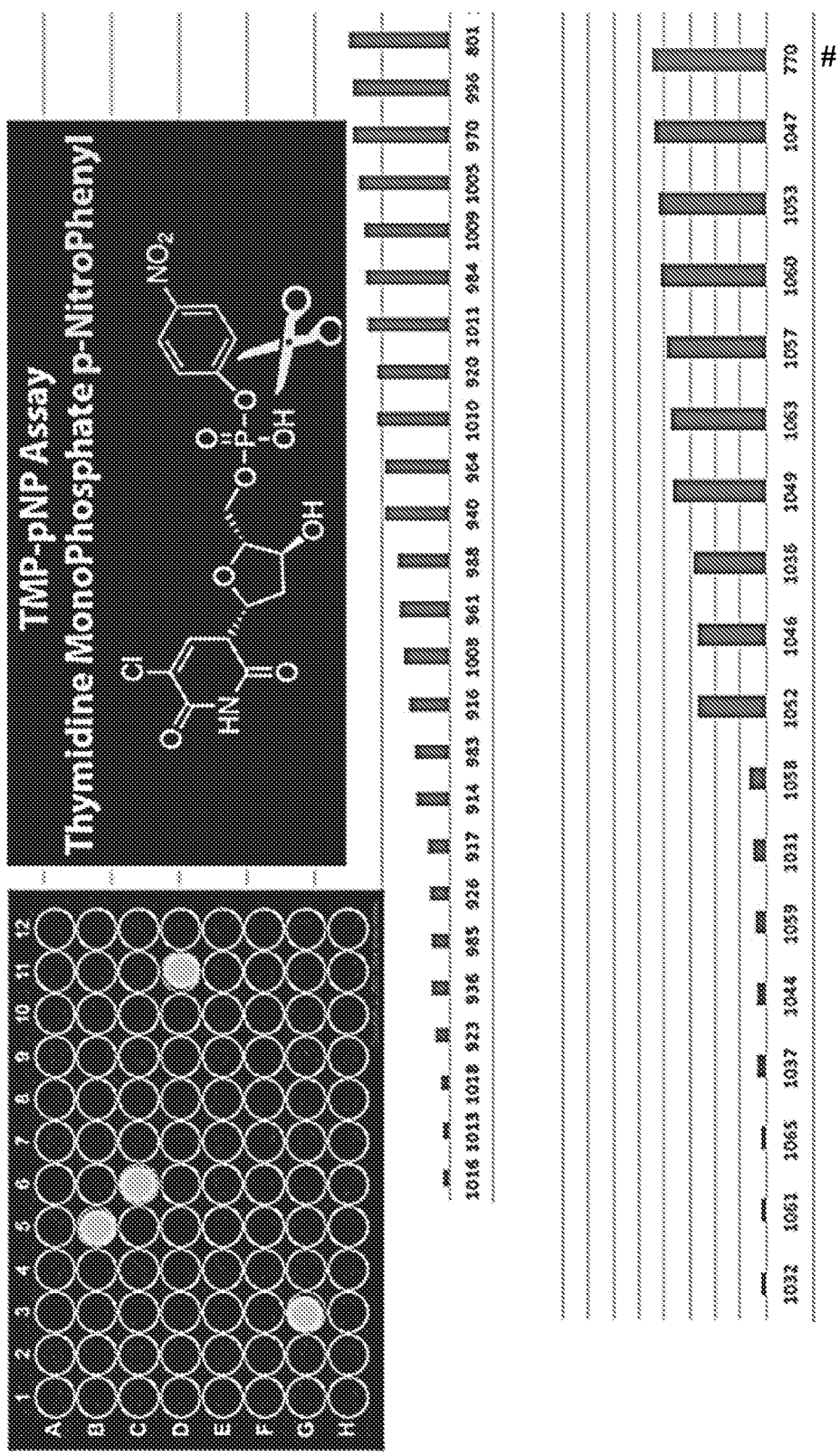
FIGS. 7A-7D illustrate selected results from high throughput TMP-pNP (thymidine monophosphate-p-nitrophenyl) assays of ENPP1 polypeptides for phosphodiesterase activity. This is a high throughput assay designed be the inventors to rapidly screen glycosylation isoforms introduced into Construct #770. The figure illustrates designing and executing a high throughput screen that is capable of rapid assessment of biological efficacy of mutants forms of the parent compound—Construct #770. Construct numbers in (#) represent the original WT clone before mutations were introduced. Construct numbers in (*) show clones with possible gain of function mutations.
Figure 7B:
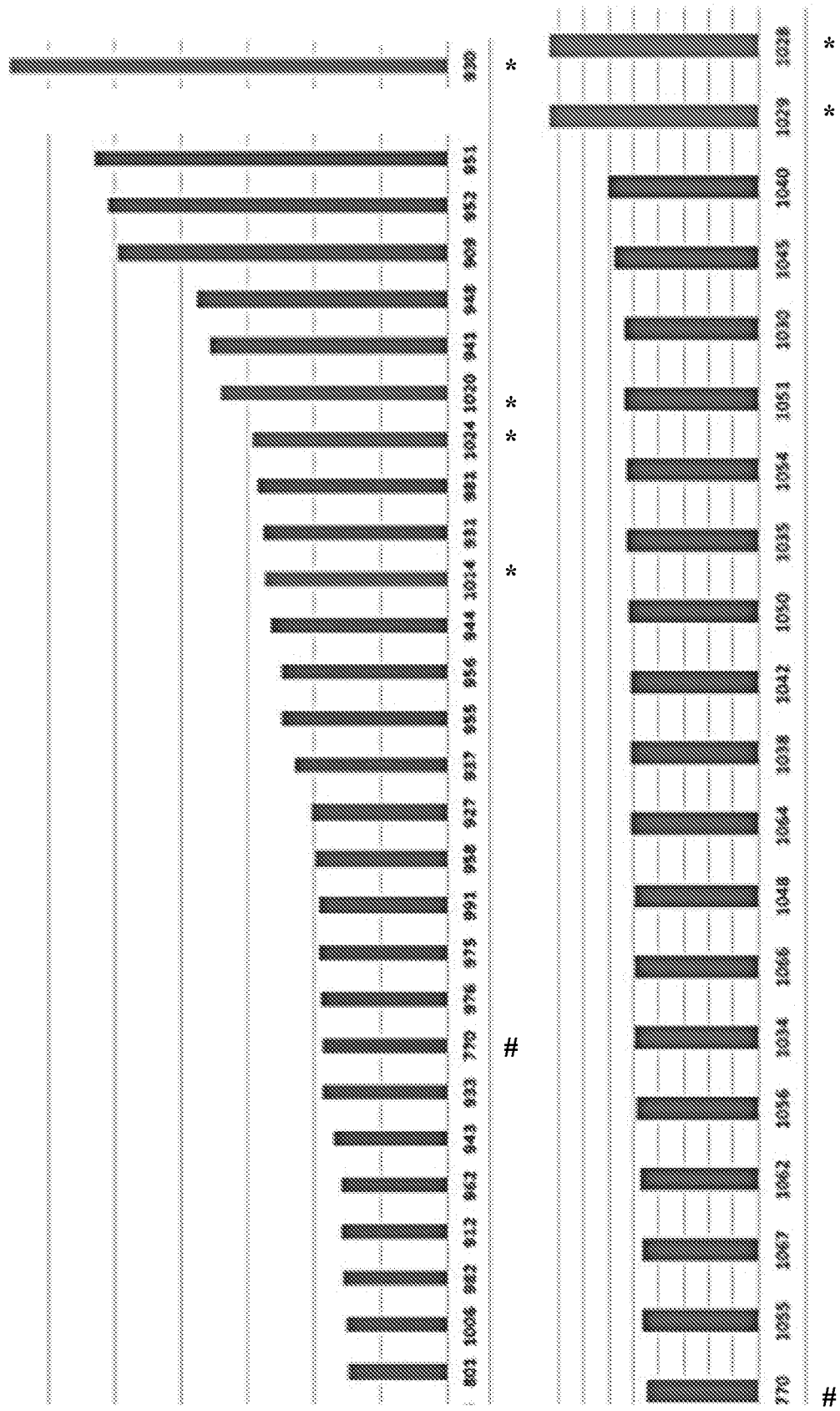
Figure 7C:
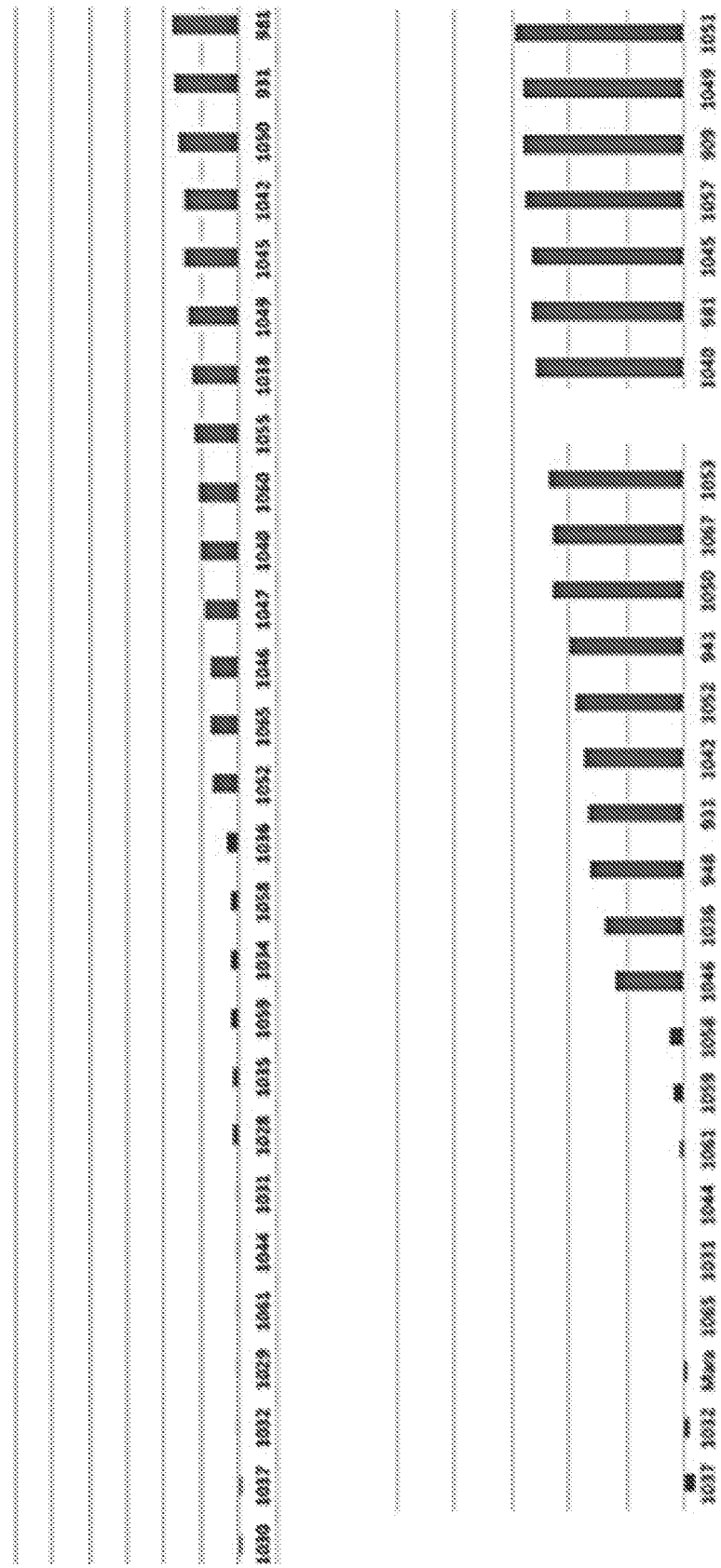
Figure 7D:
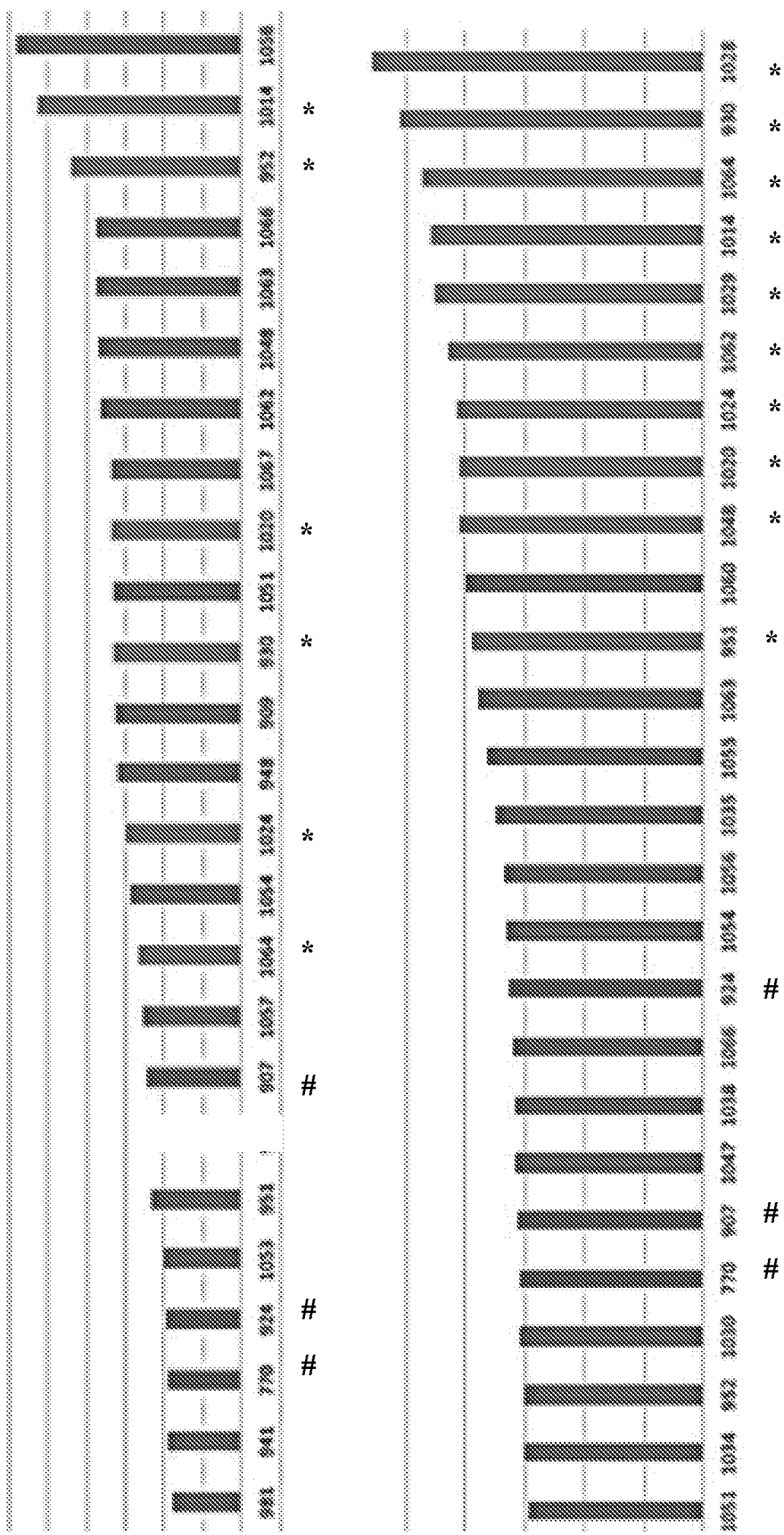

Improvement of the pharmacokinetic properties of the ENPP1-Fc was sought by introducing additional N-linked glycosylation sites and enhancing the pH dependent recycling of the fusion protein. As a way to guide the selection of additional N-linked glycosylation sites, electron density maps derived from X-ray diffraction of mouse Enpp1 crystals were used, and this revealed 4 glycosylation sites in Enpp1. These sites were assumed to be present in the highly homologous human ENPP1, and in addition, human ENPP1 contains an additional four N-linked glycosylation consensus sequences whose glycosylation status in unknown (FIG. 6B).

To identify regions of ENPP1 amenable to hyperglycosylation that would not adversely impact catalytic activity a combination of structural modeling, clinical data, and genetic data on ENPP1 in GACI patients was used. First, N-linked glycosylation consensus sequences were identified in ENPP2-7, and sequences that would easily permit the introduction of a glycosylation site via the alteration of a single adjacent residues were evaluated. ENPP2-7 was then structurally modeled using standard software to thread the sequences through the mouse Enpp1 structure (PDB ID code 4GTW). The location of proposed glycosylation sites were compared sites of known inactivating ENPP1 mutations in GACI (FIGS. 6A-6B) as well as the locations of di-sulfide bonds in the enzyme. If the spatial location of the proposed glycosylation sites were predicted to interfere with either, the sites were discarded. These modeling studies resulted in identification of 53 potential sites for additional N-linked glycosylation procedures which could easily be introduced into ENPP1 that were not expected to disrupt the folding or enzymatic activity of the protein (FIGS. 7, 13, and 14).

The additional N-linked glycosylation consensus sequences were then introduced into human ENPP1-Fc (hENPP1-Fc, Construct #770) via site directed mutagenesis. The proteins were transiently expressed in CHO cells in 96 well plates and the enzymatic activity of the extracellular supernatant from each clone was screened in triplicate in a high throughput assay using pNP-TMP as a chromogenic substrate as described in the methods (FIGS. 7A-7D). The rate of pNP-TMP hydrolysis in 10 of 53 possible ENPP1-Fc isoforms was equal to or better than Construct #770 (FIGS. 7A-7D), and these 10 glycoforms were selected for combinatorial optimization with one-another and the IgG1 Fc domain as described below.

Figure 8A:
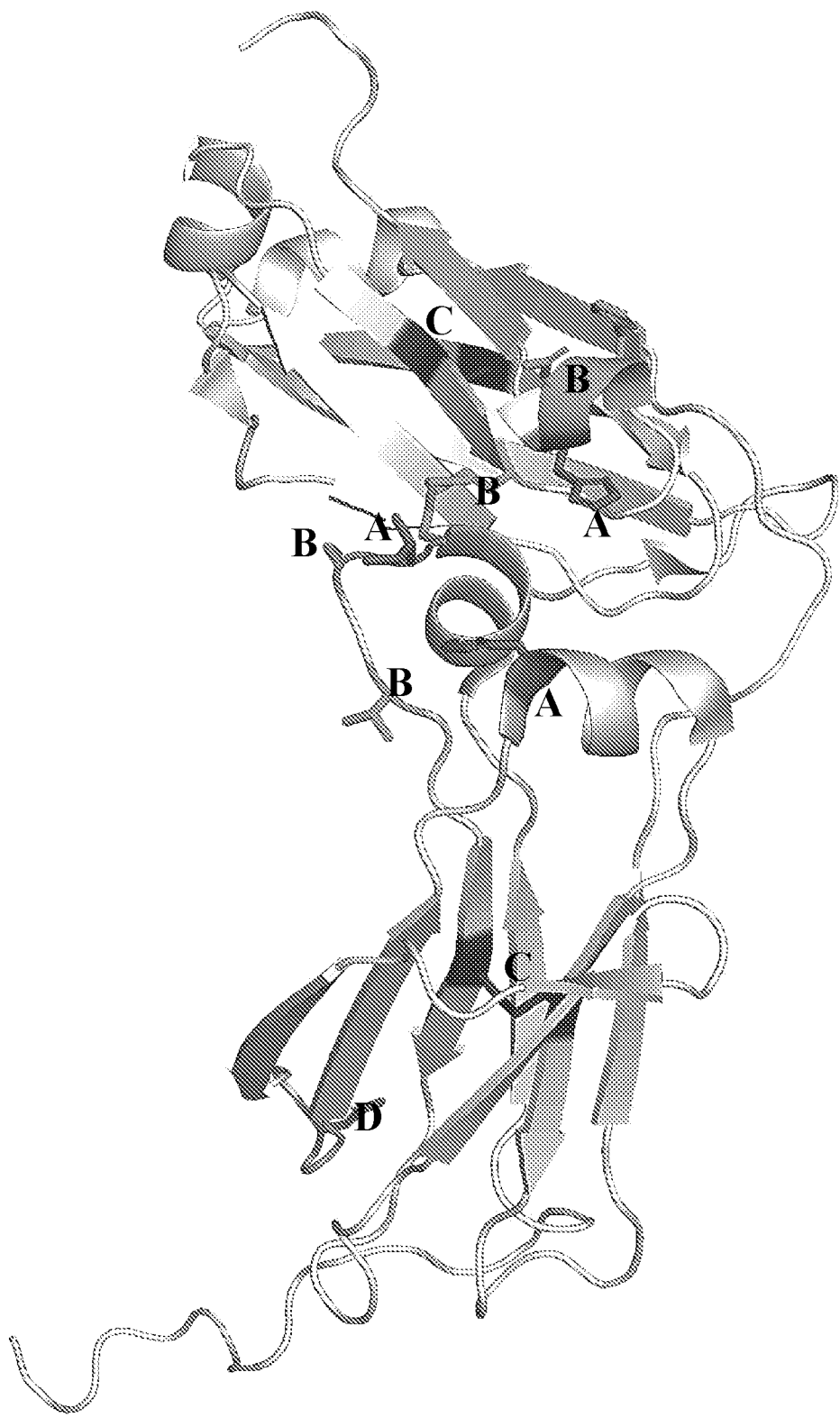
FIG. 8A is ribbon diagram illustrating the Fc domain of human IgG1. This domain is fused onto the C-terminal portion of ENPP1 to increase efficacy. Mutations in Fc domain were introduced to enhance pH-dependent recycling by FcRn. (A)=sites that abrogate binding of acidic dependence. (B)=sites that enhance binding. (C)=cysteine disulfide bonds. Magenta=known glycosylation sites.
Figure 8B:
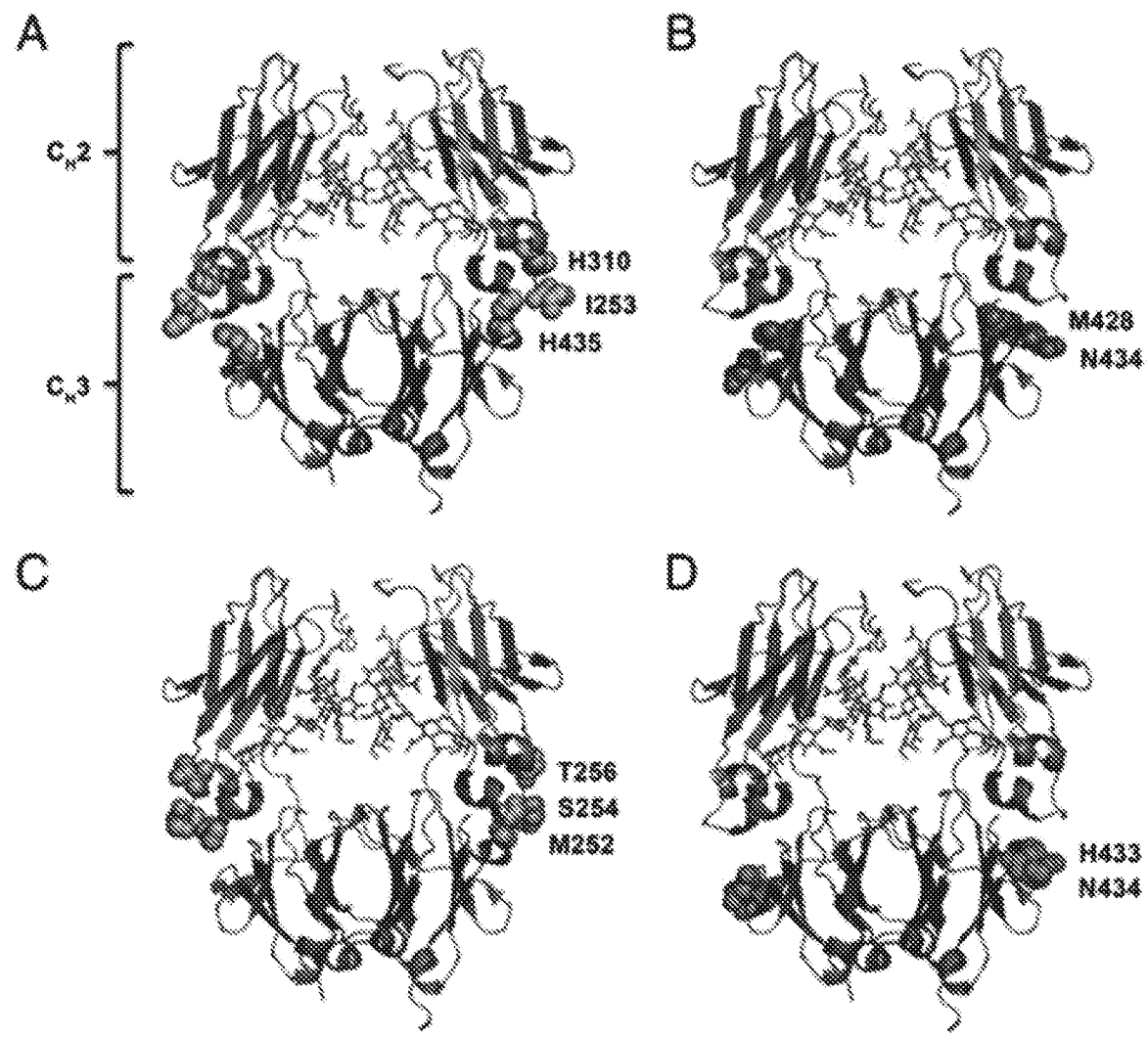
FIG. 8B illustrates mutations in the Fc domain of human IgG1 known to enhance pH dependent recycling by FcRn.
Figure 9:
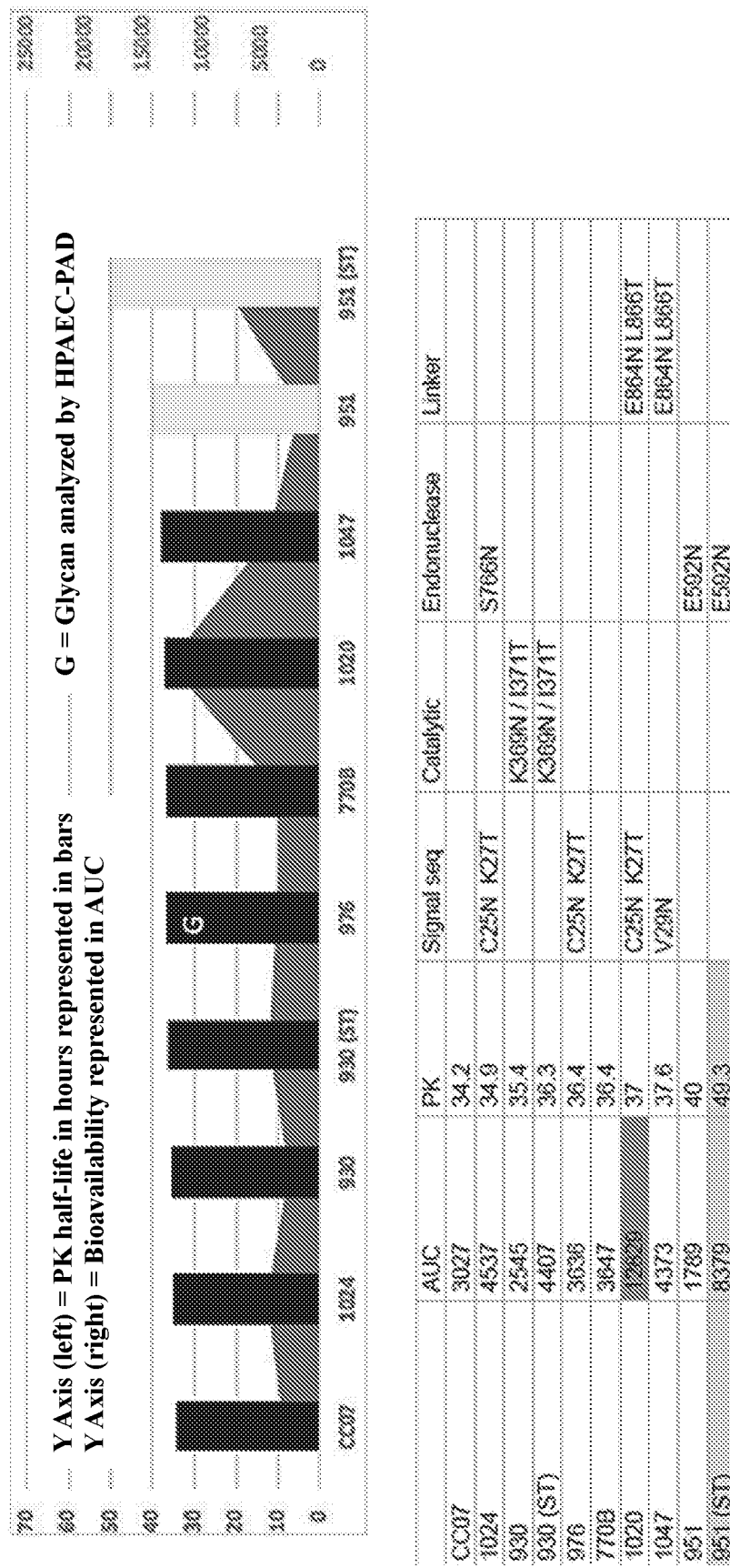
FIG. 9 comprises a graph and a table illustrating the effect of glycosylation in PK (in terms of half-life, hours) and bioavailability of ENPP1 polypeptides. The PK for all the mutations were comparable to that of Construct #CC07 (770B). Further, Construct #951 showed similar PK value to that of Construct #CC07, but Construct #951 grown in cell lines stably transfected with ST6GAL1 (Construct #951-ST) showed improved PK and bioavailability. Construct #930 had similar half-life, but lower bioavailability, than Construct #CC07. In contrast, Construct #1020 had higher bioavailability than Construct #CC07. PK and bioavailability data are presented in the table, determined as illustrated in FIGS. 3, 4, and 12 and calculated using Equation 1.

FcRn is the main homeostatic regulator of human IgG1 Fc serum half-life, and mutations in the Fc domain which enhance the pH dependent interactions of Fc with FcRn extend the circulatory half-life of biologic antibodies. Effects of two Fc mutations reported to enhance pH dependent recycling were examined herein—H433K/N434F, hereafter referred to as HN mutations, and M242Y/S254T/T246E, hereafter referred to as MST mutations (FIGS. 8A-8B). Either of the two variants of the Fc domain were combined randomly with one or more of the 10 ENPP1-Fc glycoforms demonstrating acceptable hydrolysis rates to create 12 additional ENPP1-Fc clones (Table 3). Some of these clones were chosen to test the effects of multiple glycoforms on pharmacokinetics of ENPP1-Fc, where two spatially distinct putative glycosylation sites on different protein domains were selected to enhance potential glycan shielding effects on protein surface area (Table 3; Constructs #1057, #1064, #1014, #1040). Other clones tested only the effect of Fc mutations on pK properties alone or in the presence of a single additional putative glycosylation (Table 3; Constructs #981 and #1051, respectively).

Example 2: Expression Using CHO Cell Lines and Growth Conditions

Non-human Chinese Hamster Ovary (CHO) cells are widely employed for the production of biologics due to the similarity of the CHO and human glycosylation patterns in recombinantly produced protein. Nevertheless, glycosylation differences between the two exist, most notably, human N-linked glycans contain terminal sialic acid residues with both α-2,3 and α-2,6 linkages while CHO cells contain only α-2,3 linkages.

To test whether terminal sialyation differences between CHO and human cells impact the PK and bioavailability in the present system, a CHO cell line stably expressing human α-2,6-sialytransferase (α-2,6-ST) was established as a host, and this clone was used for the production of 7 ENPP1 isoforms to compared the effect of α-2,6 linkages on PK and bioavailability in the various Constructs (Table 5; Construct numbers ending in '-ST'). To explore the effects of growth conditions on PK and bioavailability, cells stably transfected with select ENPP1-Fc isoforms (both CHO K1 cells and CHO K1 cells stably transfected with human α-2,6-ST) were supplemented with a "high-flux" precursor of sialic acid called 1,3,4-O-$Bu_3$ManNAc during protein production (Table 5).

The ENPP1-Fc isoforms were purified to homogeneity using an identical purification scheme and the Michaelis-Menton enzymatic rate constants and pharmacokinetic properties were determined as described elsewhere herein. Finally, to quantitate the biological impact of clone optimization, the pharmacodynamic effects of select ENPP1-Fc isoforms were quantitated by determining plasma PPi concentrations at multiple time points following a single subcutaneous dose of each isoform.

Example 3: Pharmacokinetic Effects of Additional N-Linked Glycosylation Sites

The addition of N-linked glycosylation sites using the in silico prediction and HTS methods described above increased the in vivo exposure of mice to ENPP1-Fc significantly in a glycoform—by 4-fold in Construct #1020. The size of the ENPP1-Fc isoforms in Table 2 were compared by SDS-PAGE gels to determine which sequence variation resulted in increased glycosylation, and showed increases in the molecular weight consistent with the addition of glycosylations. To determine whether the sequence changes in Construct #1020 successfully introduced glycosylations MALDI-TOF was used, which also confirmed the presence of glycosylations at these sites.

Example 4: Pharmacokinetic Effects Fc IgG1 Mutations (FIGS. 10-11)

Antibodies containing mutations in the Fc domain that enhance their affinity for the FcRn and increase the pH dependent antibody recycling have never been used in therapeutic enzymes fused to the Fc domain. Some Fc mutations successfully increased affinity of the Fc domain for the FcRn receptor but resulted in unfavorable PK properties in antibody PK in vivo, while others were shown to enhance PK properties in vivo.

To determine whether analogous Fc changes enhance the PK properties of enzyme fusion proteins, two specific IgG1 mutations in Fc previously used in biologic antibodies were investigated—H433K/N434F and M242Y/S254T/T246E. In general, the M242Y/S254T/T246E mutations were found to be superior to H433K/N434F at improving the properties of ENPP1-Fc. For example, Construct #981, possessing only the M242Y/S254T/T246E mutation when compared to Construct #770, increased the half-life by 3.3 fold and the AUC by 5.8 fold. In contrast, constructs with the H433K/N434F mutation in the context of various ENPP1 mutations achieved more modest half-life increases of between 1.2-1.7 fold.

Example 5: Effect of Host Cells and Growth Conditions

Expressing proteins in CHO cells stably transfected with human α-2,6-ST to produce recombinant biologics with terminal sialic acid residues possessing both alpha-2,3 and alpha-2,6 linkages has been used with variable success, with reports of increased and decreased PK properties depending on the biologic.

To determine if alpha-2,6 linkages would impact the PK properties of ENPP1-Fc the in vivo exposure (AUC) and half-life of seven ENPP1-Fc isoforms produced in either CHOK1 cells or CHOK1 cells stably transfected with human α-2,6-ST were directly compared (Table 4). A general trend that emerged producing the biologic in CHOK1 cells stably transfected with human α-2,6-ST was beneficial. The strongest effects were noted in exposure of organism to drug (AUC) which demonstrated increases in AUC of 1.7-4.6 fold in the isoforms that responded (Constructs #1057, #1028, #951, #930, and #981). Another trend was that the magnitude of effect in AUC was greater in isoforms with lower initial AUC (Constructs #951 and #1057). However, the effect in the longer acting isoforms (Constructs #1028 and #981) was sizable, yielding AUC values 8-10 fold greater than the parent compound produced in CHOK1 cells.

The effects of α-2,6 linkages on half-life were more modest, with increases of 20-30% in the Constructs that responded. To understand the differential effects of α-2,6 linkages on AUC and half-life protein activity vs time of isoforms produced in CHOk1 cells and 1078 cells were compared.

Example 6: Pharmacokinetic Effects of Growth with High-Flux Sialic Acid Precursor To determine the effect of growth conditions on PK properties, culture media of select clones were supplemented with a "high-flux" precursor of sialic acid, 1,3,4-O-Bu$_3$ManNAc, or sialic acid itself. Supplementation of CHOK1 cells with 1,3,4-O-Bu$_3$ManNAc did little to improve the PK properties of ENPP1-Fc, but when the biologic was produced in CHOK1 cells stably transfected with human α-2,6-ST, the effects on half-life and AUC were noticeable (FIG. 12 and Table 4). For example, supplementing cell culture media of CHOK1 cells producing Construct #1014 with 1,3,4-O-Bu$_3$ManNAc did little to enhance AUC and appeared to degrade the half-life of the isoform. In contrast, when 1,3,4-O-Bu$_3$ManNAc was added to the cell culture media of Construct #1057 produced in CHOK1 cells stably transfected with α-2,6-ST, the effects were more dramatic. These effects yielded net increases in AUC and half-life of 4-fold and 2-fold compared to the same isoform produced in CHOK1 grown in media not supplemented with 1,3,4-O-Bu$_3$ManNAc (FIG. 12 and Table 4).

TABLE 1

| Construct # | Mutation | Mutated Domains |
|---|---|---|
| 970 | S885N | Fc |
| 956 | S766N | Endonuclease |
| 981 | M883Y, S885T, T887E | Fc |
| 1020 | C25N, K27T, E864N, L866T | N-terminus region |
| 1062 | C25N, K27T, P534N, V536T, H1064K, N1065F | N-terminus region; Endonuclease; Fc |
| 941 | P554L, R545T | Endonuclease |
| 1057 | V29N, S766N, H1064K, N1056F | N-terminus region; Endonuclease; Fc |
| 1014 | V29N, E592N, H1064K, N1065F | N-terminus region; Endonuclease; Fc |
| 1040 | V29N, P534N, V536T, M883Y, S885T, T887E | N-terminus region; Endonuclease; Fc |

TABLE 2

Effect of additional N-linked glycosylation on pharmacokinetics (PK).

| Construct | Mutation | Domain | AUC | Half-Life (hours) |
|---|---|---|---|---|
| 770 | None | | 3027 | 36.4 |
| 970 | S885N | Fc | | |
| 956 | S766N | Endonuclease | | |
| 941 | P544L, R545T | Endonuclease | | |
| 951 | E592N | Endonuclease | 1,789 | 40 |
| 930 | K369N, I371T | Catalytic | 2,545 | 35.4 |
| 976 | C25N, K27T | N-terminus region | 3,636 | 36.4 |
| 1047 | V29N; E864N, L866T | N-terminus region & Linker | 4,373 | 37.6 |
| 1024 | C25N, K27T; S766N | N-terminus region & Endonuclease | 4,537 | 34.9 |
| 1020 | C25N, K27T and E864N, L866T | N-terminus region & Linker | 12,829 | 37 |

TABLE 3

Effect of Fc mutations on pharmacokinetics (PK).

| Construct | Mutation | Glycan Domain | $V_{max}$ | AUC | Half-Life (hours) |
|---|---|---|---|---|---|
| 1062 | C25N and K27T; P534N and V536T; H1064K/N1065F | N-terminus region & Endonuclease | | | |
| 1063 | C25N, K27T; E864N, L866T; H1064K/N1065F | N-terminus region & Endonuclease | | | |
| 1030 | S766N M883Y/S885T/T887E | Endonuclease | | 1,912 | 45.4 |
| 1057 | V29N; S766N; H1064K, N1065F | N-terminus region & Endonuclease | | 5,826 | 64.6 |
| 1064 | C25N, K27T; S766N, H1064K/N1065F | N-terminus region & Endonuclease | | 7,540 | 50.6 |
| 1051 | V29N H106K/N1065F | N-terminus region & Endonuclease | | 13,812 | 63.4 |
| 1082 | V29N; E592N M883Y/S885T/T887E | Endonuclease | | 14,978 | 70 |
| 1028 | E592N M883Y/S885T/T887E | Endonuclease | | 16,932 | 80.1 |
| 981 | M883Y/S885T/T887E | None | | 17,587 | 122.5 |
| 1014 | V29N; E592N; H1064K/N1065F | N-terminus region & Endonuclease | | 21,752 | 99.9 |
| 1040 | V29N; P534N, V536T; M883Y/S885T/T887E | N-terminus region & Endonuclease | | 32,391 | 119.4 |

Table 4: Effect of cell lines and mutations on pharmacokinetics (PK). Those Constructs marked as "-ST" were prepared using a modified CHO cells line stably transfected with human α-2,6-sialyltransferase (α-2,6-ST); this enhances the amount of sialyation of the fusion protein when compared with the fusion protein expressed in normal CHO cell lines. Enhanced sialyation of the Constructs resulted in improvements in AUC and half-life values.

| Construct | Mutation | Domain | AUC | Half-Life (hours) |
|---|---|---|---|---|
| 1057 * | V29N; S766N; H1064K, N1065F | N-terminus region & Endonuclease | 5,826 | 64.6 |
| 1057-ST ** | V29N; S766N H1064K/N1065F | N-terminus region & Endonuclease | 15,337 | 87.4 |
| 1028 * | E592N M883Y/S885T/T887E | Endonuclease | 16,932 | 80.1 |
| 1028-ST ** | E592N M883Y/S885T/T887E | Endonuclease | 25,500 | 100 |
| 951 | E592N | Endonuclease | 1,789 | 40 |
| 951-ST ** | E592N | Endonuclease | 8,379 | 49.3 |
| 930 | K369N, I371T | Catalytic | 2,545 | 35.4 |
| 930-ST ** | K369N, I371T | Catalytic | 4,407 | 36.3 |
| 981 * | M883Y/S885T/T887E | None | 17,587 | 122.5 |
| 981-ST ** | M883Y/S885T/T887E | None | 30,021 | 122.5 |
| 1014 * | V29N; E592N; H1064K/N1065F | N-terminus region & Endonuclease | 21,752 | 99.9 |
| 1014-ST ** | V29N; E592N H1064K/N1065F | N-terminus region & Endonuclease | 13,882 | 96.2 |

\* Constructs transfected into CHO-K1 cells
\*\* Constructs transfected into CHO-K1-MOD cells

TABLE 5

Effect of sialic acid supplementation on pharmacokinetics (PK). Those Constructs marked as "-ST" were prepared using a modified CHO cells line stably transfected with human α-2,6-sialyltransferase (α-2,6-ST); this enhances the amount of sialyation of the fusion protein when compared with the fusion protein expressed in normal CHO cell lines. Those Constructs marked as "-A" were prepared in cells grown in culture media supplemented with 1,3,4-O-Bu$_3$ManNAc, a "high-flux" precursor of sialic acid, during protein production.

| Construct | Mutation | Domain | AUC | Half-Life (hours) |
|---|---|---|---|---|
| 1057 | V29N; S766N; H1064K, N1065F | N-terminus region & Endonuclease | 5,826 | 64.6 |
| 1057-ST | V29N; S766N; H1064K/N1065F | N-terminus region & Endonuclease | 15,337 | 87.4 |
| 1057-ST-A | V29N; S766N; H1064K/N1065F | N-terminus region & Endonuclease | 23,867 | 124.9 |
| 1014 | V29N; E592N; H1064K/N1065F | N-terminus region & Endonuclease | 21,752 | 99.9 |
| 1014-A | V29N; E592N; H1064K/N1065F | N-terminus region & Endonuclease | | |

TABLE 6

List of polypeptides and corresponding mutations

| Polypeptide | Region of Mutation | Mutated Residues |
|---|---|---|
| 970 | Fc | S885N |
| 956 | Endonuclease | S766N |
| 981 | Fc | M883Y, S885T, T887E |
| 1020 | N terminal region and linker region | C25N, K27T, E864N, L866T |
| 1062 | N terminal, Endonuclease, and Fc | C25N, K27T, P534N, V536T, H1064K, N1065F |
| 941 | Endonuclease | P554L and R545T |
| 1057 | N terminal, Endonuclease and Fc | V29N, S766N, H1064K, N1065F |
| 1014 | N terminal, Endonuclease and Fc | V29N, E592N, H1064K, N1065F |
| 1040 | N terminal, Endonuclease and Fc | V29N, P534N, V536T, M883Y, S885T, T887E |
| 930 | Catalytic | K369N and I371T |
| 951 | Endonuclease | E592N |
| 976 | N terminal | C25N, K27T |
| 1024 | N terminal and Endonuclease | C25N, K27T, S766N |
| 1028 | Endonuclease and Fc | E592N, M883Y, S885T, T887E |
| 1030 | Endonuclease and Fc | S766N, M883Y, S885T, T887E |
| 1047 | N terminal and linker region | V29N, E864N, L866T |
| 1051 | N terminal and Fc | V29N, H1064K, N1065F |
| 1062 | N terminal region, Endonuclease and Fc | C25N, K27T, P534N, V536T, H1064K, N1065F |
| 1063 | N terminal region, linker and Fc | C25N, K27T, E864N, L866T, H1064K, N1065F |
| 1064 | N terminal region, Endonuclease and Fc | C25N, K27T/S766N/H1064K, N1065F |
| 1082 | N terminal region, Endonuclease and Fc | V29N, E592N, M883Y, S885T, T887E |
| 1089 | N terminal region, Endonuclease, Trypsin KO and Fc | V29N, E592N, R741A, H1064K, N1065F |

TABLE 7

List of mutations in ENPP1 polypeptide

| Residue of Mutation | Residue of Mutation |
|---|---|
| C25N | P558N |
| K27T | E560T |
| V29N | E591N |
| E115N | E592K |
| P117T | E592N |
| P125T | P643T |
| A276N | S645T |
| L278T | S765N |
| D285N | S766N |
| R287T | S885N |
| Y364T | R741A |
| K369N | V793N |
| I371T | H794S |
| H409T | G795T |
| P448L | G795N |
| S449T | H797T |
| P521L | E864N |
| V522T | L866T |
| V522N | H1064K |
| K526N | N1065K |
| P528T | M883Y |
| P534N | S885T |
| V536T | T887E |
| P543L | M1059L |
| R544T | N1065S |
| R545T | I884A |
| G548T | H941A |
| P554H | H1066A |
| P554L | |

ENUMERATED EMBODIMENTS

The following exemplary embodiments are provided, the numbering of which is not to be construed as designating levels of importance.

Embodiment 1 provides an ENPP1 polypeptide fusion comprising an ENPP1 polypeptide fused to a Fc region of an immunoglobulin, wherein the Fc region comprises at least one mutation selected from the group consisting of M883Y, S885N, S885T, T887E, H1064K, and N1065F as relating to SEQ ID NO:7.

Embodiment 2 provides the polypeptide fusion of Embodiment 1, wherein the Fc region comprises at least one mutation selected from the group consisting of S885N, M883Y, M883Y/S885T/T887E, and H1064K/N1065F as relating to SEQ ID NO:7.

Embodiment 3 provides an ENPP1 polypeptide fusion comprising an ENPP1 polypeptide fused to a Fc region of an immunoglobulin, wherein the ENPP1 polypeptide comprises at least one mutation selected from the group consisting of C25N, K27T, and V29N as relating to SEQ ID NO:7.

Embodiment 4 provides the polypeptide fusion of Embodiment 3, wherein the ENPP1 polypeptide comprises at least one mutation selected from the group consisting of C25N/K27T and V29N as relating to SEQ ID NO:7.

Embodiment 5 provides an ENPP1 polypeptide fusion comprising an ENPP1 polypeptide fused to a Fc region of an immunoglobulin, wherein the ENPP1 polypeptide comprises at least one mutation selected from the group consisting of K369N, and I371T as relating to SEQ ID NO:7.

Embodiment 6 provides the polypeptide fusion of Embodiment 5, wherein the ENPP1 polypeptide comprises at least the mutation K369N/I371T as relating to SEQ ID NO:7.

Embodiment 7 provides an ENPP1 polypeptide fusion comprising an ENPP1 polypeptide fused to a Fc region of an immunoglobulin, wherein the ENPP1 polypeptide comprises at least one mutation selected from the group consisting of P534N, V536T, R545T, P554L, E592N, R741D, and S766N as relating to SEQ ID NO:7.

Embodiment 8 provides the polypeptide fusion of Embodiment 7, wherein the ENPP1 polypeptide comprises at least one mutation selected from the group consisting of P534N/V536T, P554L/R545T, E592N, E592N/R741D, and S766N as relating to SEQ ID NO:7.

Embodiment 9 provides an ENPP1 polypeptide fusion comprising an ENPP1 polypeptide fused to a Fc region of an immunoglobulin, wherein the ENPP1 polypeptide comprises at least one mutation selected from the group consisting of E864N and L866T as relating to SEQ ID NO:7.

Embodiment 10 provides the polypeptide fusion of Embodiment 9, wherein the ENPP1 polypeptide comprises at least the mutation E864N/L866T as relating to SEQ ID NO:7.

Embodiment 11 provides the polypeptide fusion of any of Embodiments 1-10, comprising at least one mutation selected from the group consisting of C25N, K27T, V29N, C25N/K27T, K369N, I371T, K369N/I371T, P534N, V536T, R545T, P554L, E592N, R741D, S766N, P534N/V536T, P554L/R545T, E592N/R741D, E864N, L866T, E864N/L866T, M883Y, S885N, S885T, T887E, H1064K, N1065F, M883Y/S885T/T887E, H1064K/N1065F as relating to SEQ ID NO:7.

Embodiment 12 provides the polypeptide fusion of any of Embodiments 1-11, wherein the Fc region is of an IgG.

Embodiment 13 provides the polypeptide fusion of any of Embodiments 1-12, comprising at least one mutation selected from the group consisting of P534N, V536T, R545T, P554L, S766N, and E592N as relating to SEQ ID NO:7.

Embodiment 14 provides the polypeptide fusion of any of Embodiments 1-12, comprising at least one mutation selected from the group consisting of S766N, P534N/Y536T, P554L/R545T, and E592N as relating to SEQ ID NO:7.

Embodiment 15 provides the polypeptide fusion of any of Embodiments 1-12, comprising at least one mutation selected from the group consisting of S885N, S766N, M883Y/S885T/T887E, E864N/L866T, P534N/V536T/H1064K/N1065F, P554L/R545T, S766N/H1064K/N1065F, E592N/H1064K/N1065F, and P534N/V536T/M883Y/S885T/T887E as relating to SEQ ID NO:7.

Embodiment 16 provides an ENPP1 polypeptide fusion comprising an ENPP1 polypeptide and a Fc region of an immunoglobulin, the polypeptide fusion comprising mutations M883Y, S885T, and T887E as relating to SEQ ID NO:7.

Embodiment 17 provides an ENPP1 polypeptide fusion comprising an ENPP1 polypeptide and a Fc region of an immunoglobulin, the polypeptide fusion comprising mutations P534N, V536T, M883Y, S885T, and T887E as relating to SEQ ID NO:7.

Embodiment 18 provides an ENPP1 polypeptide fusion comprising an ENPP1 polypeptide and a Fc region of an immunoglobulin, the polypeptide fusion comprising mutations E592N, H1064K, and N1065F as relating to SEQ ID NO:7.

Embodiment 19 provides an ENPP1 mutant polypeptide comprising SEQ ID NO:7, wherein the mutant polypeptide comprises a mutation selected from the group consisting of S766N, P534N, V536T, P554L, R545T, and E592N as relating to SEQ ID NO:7.

Embodiment 20 provides the mutant polypeptide of Embodiment 19, wherein the mutant polypeptide comprises at least one mutation selected from the group consisting of S766N, P534N/V536T, P554L/R545T, and E592N as relating to SEQ ID NO:7.

Embodiment 21 provides the mutant polypeptide of Embodiment 19, comprising mutations selected from the group consisting of: S885N, S766N, M883Y/S885T/T887E, P534N/V536T/H1064K/N1065F, P554L/R545T, S766N/H1064K/N1065F, E592N/H1064K/N1065F, and P534N/V536T/M883Y/S885T/T887E as relating to SEQ ID NO:7.

Embodiment 22 provides the mutant polypeptide of claim 19, comprising a S885N mutation as relating to SEQ ID NO:7.

Embodiment 23 provides the mutant polypeptide of claim 19, comprising a S766N mutation as relating to SEQ ID NO:7.

Embodiment 24 provides the mutant polypeptide of claim 19, comprising mutations M883Y, S885T, and T887E as relating to SEQ ID NO:7.

Embodiment 25 provides the mutant polypeptide of claim 19, comprising mutations P534N, V536T, H1064K, and N1065F as relating to SEQ ID NO:7.

Embodiment 26 provides the mutant polypeptide of claim 19, comprising mutations P554L and R545T as relating to SEQ ID NO:7.

Embodiment 27 provides the mutant polypeptide of claim 19, comprising mutation S766N, H1064K, and N1065F as relating to SEQ ID NO:7.

Embodiment 28 provides the mutant polypeptide of claim 19, comprising mutation E592N, H1064K, and N1065F as relating to SEQ ID NO:7.

Embodiment 29 provides the mutant polypeptide of claim 19, comprising mutations P534N, V536T, M883Y, S885T, and T887E as relating to SEQ ID NO:7.

Embodiment 30 provides the polypeptide fusion of any of Embodiments 1-18 or the mutant polypeptide of any of Embodiments 19-29, which is expressed from a CHO cell line stably transfected with human ST6 beta-galatosamide alpha-2,6-sialyltransferase (also known as ST6GAL1).

Embodiment 31 provides the polypeptide fusion of any of Embodiments 1-18 or the mutant polypeptide of any of Embodiments 19-29, which is grown in a cell culture supplemented with sialic acid and/or N-acetylmannosamine (also known as 1,3,4-O-Bu3ManNAc).

Embodiment 32 provides a method of reducing or preventing progression of pathological calcification in a subject in need thereof, the method comprising administering to the subject a therapeutically effective amount of the polypeptide fusion of any of Embodiments 1-18 and 30-31 or the mutant polypeptide of any of Embodiments 19-31.

Embodiment 33 provides a method of reducing or preventing progression of pathological ossification in a subject in need thereof, the method comprising administering to the subject a therapeutically effective amount of the polypeptide fusion of any of Embodiments 1-18 and 30-31 or the mutant polypeptide of any of Embodiments 19-31.

Embodiment 34 provides a method of reducing or preventing progression of ectopic calcification of soft tissue in a subject in need thereof, the method comprising administering to the subject a therapeutically effective amount of the polypeptide fusion of any of Embodiments 1-18 and 30-31 or the mutant polypeptide of any of Embodiments 19-31.

Embodiment 35 provides a method of treating, reversing, or preventing progression of ossification of the posterior longitudinal ligament (OPLL) in a subject in need thereof, the method comprising administering to the subject a therapeutically effective amount of the polypeptide fusion of any of Embodiments 1-18 and 30-31 or the mutant polypeptide of any of Embodiments 19-31.

Embodiment 36 provides a method of treating, reverting, or preventing progression of hypophosphatemic rickets in a subject in need thereof, the method comprising administering to the subject a therapeutically effective amount of the polypeptide fusion of any of Embodiments 1-18 and 30-31 or the mutant polypeptide of any of Embodiments 19-31.

Embodiment 37 provides a method of reducing or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of the polypeptide fusion of any of Embodiments 1-18 and 30-31 or the mutant polypeptide of any of Embodiments 19-31.

Embodiment 38 provides a method of reducing or preventing progression of aging related hardening of arteries in a subject in need thereof, the method comprising administering to the subject a therapeutically effective amount of the polypeptide fusion of any of Embodiments 1-18 and 30-31 or the mutant polypeptide of any of Embodiments 19-31.

Embodiment 39 provides the method of Embodiment 32, wherein the pathological calcification is selected from the group consisting of idiopathic infantile arterial calcification (IIAC) and calcification of atherosclerotic plaques.

Embodiment 40 provides the method of Embodiment 33, wherein the pathological ossification is selected from the group consisting of ossification of the posterior longitudinal ligament (OPLL), hypophosphatemic rickets, and osteoarthritis.

Embodiment 41 provides the method of Embodiment 34, wherein the soft tissue calcification is selected from the group consisting of IIAC and osteoarthritis.

Embodiment 42 provides the method of Embodiment 34, wherein the soft tissue is selected from the group consisting of atherosclerotic plaques, muscular arteries, joint, spine, articular cartilage, vertebral disk cartilage, vessels, and connective tissue.

Embodiment 43 provides a method of raising pyrophosphate (PPi) levels in a subject having PPi level lower than PPi normal level, the method comprising administering to the subject a therapeutically effective amount of a polypeptide of the polypeptide fusion of any of Embodiments 1-18 and 30-31 or the mutant polypeptide of any of Embodiments 19-31, whereby upon the administration the level of the PPi in the subject is elevated to a normal level of at least 2 µM and is maintained at approximately the same level.

Embodiment 44 provides a method of reducing or preventing the progression of pathological calcification or ossification in a subject having pyrophosphate (PPi) level lower than PPi normal level, the method comprising administering to the subject a therapeutically effective amount of a polypeptide fusion of any of Embodiments 1-18 and 30-31 or the mutant polypeptide of any of Embodiments 19-31, whereby pathological calcification or ossification in the subject is reduced or progression of pathological calcification or ossification in the subject is prevented.

Embodiment 45 provides a method of treating ENPP1 deficiency manifested by a reduction of extracellular pyrophosphate (PPi) concentration in a subject in need thereof, the method comprising administering to the subject a therapeutically effective amount of a polypeptide fusion of any of Embodiments 1-18 and 30-31 or the mutant polypeptide of any of Embodiments 19-31, whereby the level of the PPi in the subject is elevated.

Embodiment 46 provides the method of any of Embodiments 32-45, wherein the polypeptide fusion or mutant polypeptide is a secreted product of a ENPP1 precursor protein expressed in a mammalian cell, wherein the ENPP1 precursor protein comprises a signal peptide sequence and an ENPP1 polypeptide, wherein the ENPP1 precursor protein undergoes proteolytic processing to yield the ENPP1 polypeptide.

Embodiment 47 provides the method of Embodiment 46, wherein in the ENPP1 precursor protein the signal peptide sequence is conjugated to the N-terminus of the ENPP1 polypeptide.

Embodiment 48 provides the method of any of Embodiments 46-47, wherein the signal peptide sequence is selected from the group consisting of ENPP1 signal peptide sequence, ENPP2 signal peptide sequence, ENPP7 signal peptide sequence, and ENPP5 signal peptide sequence.

Embodiment 49 provides the method of any of Embodiments 32-48, wherein the polypeptide fusion or mutant polypeptide is administered acutely or chronically to the subject.

Embodiment 50 provides the method of any of Embodiments 32-49, wherein the polypeptide fusion or mutant polypeptide is administered locally, regionally, parenterally, or systemically to the subject.

Embodiment 51 provides the method of any of Embodiments 32-50, wherein the polypeptide fusion or mutant polypeptide is administered to the subject by at least one route selected from the group consisting of subcutaneous, oral, aerosol, inhalational, rectal, vaginal, transdermal, subcutaneous, intranasal, buccal, sublingual, parenteral, intrathecal, intragastrical, ophthalmic, pulmonary, and topical.

Embodiment 52 provides the method of any of Embodiments 32-51, wherein the polypeptide fusion or mutant polypeptide is administered to the subject as a pharmaceutical composition further comprising at least one pharmaceutically acceptable carrier.

Embodiment 53 provides the method of any of Embodiments 32-52, wherein the subject is a mammal.

Embodiment 54 provides the method of Embodiment 53, wherein the mammal is human.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An ENPP1 polypeptide fusion comprising an ENPP1 polypeptide fused to a Fc region of an immunoglobulin, wherein the ENPP1 polypeptide comprises at least one mutation selected from the group consisting of C25N, K27T, V29N, K369N, I371T, P534N, V536T, R545T, P554L, E592N, R741D, and S766N as relating to SEQ ID NO:7.

2. The polypeptide fusion of claim 1, wherein the Fc region comprises:
   (a) at least one mutation selected from the group consisting of S885N, M883Y, M883Y/S885T/T887E, and H1064K/N1065F as relating to SEQ ID NO:7, or
   (b) at least one mutation selected from the group consisting of M883Y, S885N, S885T, T887E, H1064K, N1065F, E864N and L866T as relating to SEQ ID NO: 7.

3. The polypeptide fusion of claim 1, wherein the ENPP1 polypeptide comprises at least one mutation selected from the group consisting of C25N/K27T and V29N as relating to SEQ ID NO:7.

4. The polypeptide fusion of claim 1, wherein the ENPP1 polypeptide comprises at least the mutation K369N/I371T as relating to SEQ ID NO:7.

5. The polypeptide fusion of claim 1, wherein the ENPP1 polypeptide comprises at least one mutation selected from the group consisting of P534N/V536T, P554L/R545T, E592N, E592N/R741D, and S766N as relating to SEQ ID NO: 7.

6. The polypeptide fusion of claim 1, wherein the ENPP1 polypeptide comprises at least the mutation E864N/L866T as relating to SEQ ID NO:7.

7. The polypeptide fusion of claim 1, comprising at least one mutation selected from the group consisting of C25N, K27T, V29N, C25N/K27T, K369N, I371T, K369N/I371T, P534N, V536T, R545T, P554L, E592N, R741D, S766N, P534N/V536T, P554L/R545T, E592N/R741D, E864N, L866T, E864N/L866T, M883Y, S885N, S885T, T887E, H1064K, N1065F, M883Y/S885T/T887E, H1064K/N1065F as relating to SEQ ID NO:7.

8. The polypeptide fusion of claim 1, wherein the Fc region is of an IgG.

9. The polypeptide fusion of claim 1, comprising at least one mutation selected from the group consisting of P534N, V536T, R545T, P554L, S766N, and E592N as relating to SEQ ID NO:7.

10. The polypeptide fusion of claim 1, comprising at least one mutation selected from the group consisting of S766N, P534N/V536T, P554L/R545T, and E592N as relating to SEQ ID NO:7.

11. The polypeptide fusion of claim 1, comprising at least one mutation selected from the group consisting of S885N, S766N, M883Y/S885T/T887E, E864N/L866T, P534N/V536T/H1064K/N1065F, P554L/R545T, S766N/H1064K/N1065F, E592N/H1064K/N1065F, and P534N/V536T/M883Y/S885T/T887E as relating to SEQ ID NO:7.

12. An ENPP1 polypeptide fusion comprising an ENPP1 polypeptide and a Fc region of an immunoglobulin, wherein at least two of the following apply:
   (a) the polypeptide fusion comprises mutations M883Y, S885T, and T887E as relating to SEQ ID NO:7;
   (b) the polypeptide fusion comprises mutations P534N, V536T, M883Y, S885T, and T887E as relating to SEQ ID NO:7;
   (c) the polypeptide fusion comprises mutations E592N, H1064K, and N1065F as relating to SEQ ID NO:7.

13. The polypeptide fusion of claim 1, which is expressed from a CHO cell line stably transfected with human ST6 beta-galatosamide alpha-2,6-sialyltransferase (also known as ST6GAL1).

14. The polypeptide fusion of claim 1, which is grown in a cell culture supplemented with at least one of sialic acid and N-acetylmannosamine (also known as 1,3,4-O-Bu$_3$ManNAc).

15. A method of treating, reversing, or preventing progression of at least one of ossification of the posterior longitudinal ligament (OPLL) and hypophosphatemic rickets in a subject in need thereof, the method comprising administering to the subject a therapeutically effective amount of the polypeptide fusion of claim 1.

16. A method of reducing or preventing progression of at least one disease selected from the group consisting of chronic kidney disease (CKD), end stage renal disease (ESRD), calcific uremic arteriolopathy (CUA), calciphylaxis, ossification of the posterior longitudinal ligament (OPLL), hypophosphatemic rickets, osteoarthritis, aging related hardening of arteries, idiopathic infantile arterial calcification (IIAC), Generalized Arterial Calcification of Infancy (GACI), and calcification of atherosclerotic plaques in a subject diagnosed with the at least one disease, the method comprising administering to the subject a therapeutically effective amount of the polypeptide fusion of claim 1.

17. A method of reducing or preventing progression of aging related hardening of arteries in a subject in need thereof, the method comprising administering to the subject a therapeutically effective amount of the polypeptide fusion of claim 1.

18. The polypeptide fusion of claim 1, wherein the Fc region comprises at least one mutation selected from the group consisting of M883Y, S885N, S885T, T887E, H1064K, N1065F, E864N and L866T as relating to SEQ ID NO:7.

* * * * *

SEQUENCE LISTING

```
<160> NUMBER OF SEQ ID NOS: 7

<210> SEQ ID NO 1
<211> LENGTH: 925
<212> TYPE: PRT
<213> ORGANISM: Homo sapiens

<400> SEQUENCE: 1

Met Glu Arg Asp Gly Cys Ala Gly Gly Ser Arg Gly Gly Glu Gly
1               5                   10                  15

Gly Arg Ala Pro Arg Glu Gly Pro Ala Gly Asn Gly Arg Asp Arg Gly
                20                  25                  30

Arg Ser His Ala Ala Glu Ala Pro Gly Asp Pro Gln Ala Ala Ala Ser
            35                  40                  45

Leu Leu Ala Pro Met Asp Val Gly Glu Glu Pro Leu Glu Lys Ala Ala
        50                  55                  60

Arg Ala Arg Thr Ala Lys Asp Pro Asn Thr Tyr Lys Val Leu Ser Leu
65                  70                  75                  80

Val Leu Ser Val Cys Val Leu Thr Thr Ile Leu Gly Cys Ile Phe Gly
                85                  90                  95

Leu Lys Pro Ser Cys Ala Lys Glu Val Lys Ser Cys Lys Gly Arg Cys
                100                 105                 110

Phe Glu Arg Thr Phe Gly Asn Cys Arg Cys Asp Ala Ala Cys Val Glu
            115                 120                 125

Leu Gly Asn Cys Cys Leu Asp Tyr Gln Glu Thr Cys Ile Glu Pro Glu
        130                 135                 140

His Ile Trp Thr Cys Asn Lys Phe Arg Cys Gly Glu Lys Arg Leu Thr
145                 150                 155                 160

Arg Ser Leu Cys Ala Cys Ser Asp Asp Cys Lys Asp Lys Gly Asp Cys
                165                 170                 175

Cys Ile Asn Tyr Ser Ser Val Cys Gln Gly Glu Lys Ser Trp Val Glu
            180                 185                 190

Glu Pro Cys Glu Ser Ile Asn Glu Pro Gln Cys Pro Ala Gly Phe Glu
        195                 200                 205

Thr Pro Pro Thr Leu Leu Phe Ser Leu Asp Gly Phe Arg Ala Glu Tyr
    210                 215                 220

Leu His Thr Trp Gly Gly Leu Leu Pro Val Ile Ser Lys Leu Lys Lys
225                 230                 235                 240

Cys Gly Thr Tyr Thr Lys Asn Met Arg Pro Val Tyr Pro Thr Lys Thr
                245                 250                 255

Phe Pro Asn His Tyr Ser Ile Val Thr Gly Leu Tyr Pro Glu Ser His
            260                 265                 270

Gly Ile Ile Asp Asn Lys Met Tyr Asp Pro Lys Met Asn Ala Ser Phe
        275                 280                 285
```

```
Ser Leu Lys Ser Lys Glu Lys Phe Asn Pro Glu Trp Tyr Lys Gly Glu
    290                 295                 300

Pro Ile Trp Val Thr Ala Lys Tyr Gln Gly Leu Lys Ser Gly Thr Phe
305                 310                 315                 320

Phe Trp Pro Gly Ser Asp Val Glu Ile Asn Gly Ile Phe Pro Asp Ile
                325                 330                 335

Tyr Lys Met Tyr Asn Gly Ser Val Pro Phe Glu Glu Arg Ile Leu Ala
            340                 345                 350

Val Leu Gln Trp Leu Gln Leu Pro Lys Asp Glu Arg Pro His Phe Tyr
        355                 360                 365

Thr Leu Tyr Leu Glu Glu Pro Asp Ser Ser Gly His Ser Tyr Gly Pro
    370                 375                 380

Val Ser Ser Glu Val Ile Lys Ala Leu Gln Arg Val Asp Gly Met Val
385                 390                 395                 400

Gly Met Leu Met Asp Gly Leu Lys Glu Leu Asn Leu His Arg Cys Leu
                405                 410                 415

Asn Leu Ile Leu Ile Ser Asp His Gly Met Glu Gln Gly Ser Cys Lys
            420                 425                 430

Lys Tyr Ile Tyr Leu Asn Lys Tyr Leu Gly Asp Val Lys Asn Ile Lys
        435                 440                 445

Val Ile Tyr Gly Pro Ala Ala Arg Leu Arg Pro Ser Asp Val Pro Asp
    450                 455                 460

Lys Tyr Tyr Ser Phe Asn Tyr Glu Gly Ile Ala Arg Asn Leu Ser Cys
465                 470                 475                 480

Arg Glu Pro Asn Gln His Phe Lys Pro Tyr Leu Lys His Phe Leu Pro
                485                 490                 495

Lys Arg Leu His Phe Ala Lys Ser Asp Arg Ile Glu Pro Leu Thr Phe
            500                 505                 510

Tyr Leu Asp Pro Gln Trp Gln Leu Ala Leu Asn Pro Ser Glu Arg Lys
        515                 520                 525

Tyr Cys Gly Ser Gly Phe His Gly Ser Asp Asn Val Phe Ser Asn Met
    530                 535                 540

Gln Ala Leu Phe Val Gly Tyr Gly Pro Gly Phe Lys His Gly Ile Glu
545                 550                 555                 560

Ala Asp Thr Phe Glu Asn Ile Glu Val Tyr Asn Leu Met Cys Asp Leu
                565                 570                 575

Leu Asn Leu Thr Pro Ala Pro Asn Asn Gly Thr His Gly Ser Leu Asn
            580                 585                 590

His Leu Leu Lys Asn Pro Val Tyr Thr Pro Lys His Pro Lys Glu Val
        595                 600                 605

His Pro Leu Val Gln Cys Pro Phe Thr Arg Asn Pro Arg Asp Asn Leu
    610                 615                 620

Gly Cys Ser Cys Asn Pro Ser Ile Leu Pro Ile Glu Asp Phe Gln Thr
625                 630                 635                 640

Gln Phe Asn Leu Thr Val Ala Glu Glu Lys Ile Ile Lys His Glu Thr
                645                 650                 655

Leu Pro Tyr Gly Arg Pro Arg Val Leu Gln Lys Glu Asn Thr Ile Cys
            660                 665                 670

Leu Leu Ser Gln His Gln Phe Met Ser Gly Tyr Ser Gln Asp Ile Leu
        675                 680                 685

Met Pro Leu Trp Thr Ser Tyr Thr Val Asp Arg Asn Asp Ser Phe Ser
    690                 695                 700
```

```
Thr Glu Asp Phe Ser Asn Cys Leu Tyr Gln Asp Phe Arg Ile Pro Leu
705                 710                 715                 720

Ser Pro Val His Lys Cys Ser Phe Tyr Lys Asn Asn Thr Lys Val Ser
                725                 730                 735

Tyr Gly Phe Leu Ser Pro Pro Gln Leu Asn Lys Asn Ser Ser Gly Ile
            740                 745                 750

Tyr Ser Glu Ala Leu Leu Thr Thr Asn Ile Val Pro Met Tyr Gln Ser
        755                 760                 765

Phe Gln Val Ile Trp Arg Tyr Phe His Asp Thr Leu Leu Arg Lys Tyr
770                 775                 780

Ala Glu Glu Arg Asn Gly Val Asn Val Val Ser Gly Pro Val Phe Asp
785                 790                 795                 800

Phe Asp Tyr Asp Gly Arg Cys Asp Ser Leu Glu Asn Leu Arg Gln Lys
                805                 810                 815

Arg Arg Val Ile Arg Asn Gln Glu Ile Leu Ile Pro Thr His Phe Phe
            820                 825                 830

Ile Val Leu Thr Ser Cys Lys Asp Thr Ser Gln Thr Pro Leu His Cys
        835                 840                 845

Glu Asn Leu Asp Thr Leu Ala Phe Ile Leu Pro His Arg Thr Asp Asn
850                 855                 860

Ser Glu Ser Cys Val His Gly Lys His Asp Ser Ser Trp Val Glu Glu
865                 870                 875                 880

Leu Leu Met Leu His Arg Ala Arg Ile Thr Asp Val Glu His Ile Thr
                885                 890                 895

Gly Leu Ser Phe Tyr Gln Gln Arg Lys Glu Pro Val Ser Asp Ile Leu
            900                 905                 910

Lys Leu Lys Thr His Leu Pro Thr Phe Ser Gln Glu Asp
        915                 920                 925

<210> SEQ ID NO 2
<211> LENGTH: 888
<212> TYPE: PRT
<213> ORGANISM: Homo sapiens

<400> SEQUENCE: 2

Met Ala Arg Arg Ser Ser Phe Gln Ser Cys Gln Ile Ile Ser Leu Phe
1               5                   10                  15

Thr Phe Ala Val Gly Val Asn Ile Cys Leu Gly Phe Thr Ala His Arg
            20                  25                  30

Ile Lys Arg Ala Glu Gly Trp Glu Glu Gly Pro Pro Thr Val Leu Ser
        35                  40                  45

Asp Ser Pro Trp Thr Asn Ile Ser Gly Ser Cys Lys Gly Arg Cys Phe
    50                  55                  60

Glu Leu Gln Glu Ala Gly Pro Pro Asp Cys Arg Cys Asp Asn Leu Cys
65                  70                  75                  80

Lys Ser Tyr Thr Ser Cys Cys His Asp Phe Asp Glu Leu Cys Leu Lys
                85                  90                  95

Thr Ala Arg Gly Trp Glu Cys Thr Lys Asp Arg Cys Gly Glu Val Arg
            100                 105                 110

Asn Glu Glu Asn Ala Cys His Cys Ser Glu Asp Cys Leu Ala Arg Gly
        115                 120                 125

Asp Cys Cys Thr Asn Tyr Gln Val Val Cys Lys Gly Glu Ser His Trp
    130                 135                 140

Val Asp Asp Asp Cys Glu Glu Ile Lys Ala Ala Glu Cys Pro Ala Gly
145                 150                 155                 160
```

```
Phe Val Arg Pro Pro Leu Ile Ile Phe Ser Val Asp Gly Phe Arg Ala
                165                 170                 175
Ser Tyr Met Lys Lys Gly Ser Lys Val Met Pro Asn Ile Glu Lys Leu
            180                 185                 190
Arg Ser Cys Gly Thr His Ser Pro Tyr Met Arg Pro Val Tyr Pro Thr
        195                 200                 205
Lys Thr Phe Pro Asn Leu Tyr Thr Leu Ala Thr Gly Leu Tyr Pro Glu
    210                 215                 220
Ser His Gly Ile Val Gly Asn Ser Met Tyr Asp Pro Val Phe Asp Ala
225                 230                 235                 240
Thr Phe His Leu Arg Gly Arg Glu Lys Phe Asn His Arg Trp Trp Gly
                245                 250                 255
Gly Gln Pro Leu Trp Ile Thr Ala Thr Lys Gln Gly Val Lys Ala Gly
            260                 265                 270
Thr Phe Phe Trp Ser Val Val Ile Pro His Glu Arg Arg Ile Leu Thr
        275                 280                 285
Ile Leu Gln Trp Leu Thr Leu Pro Asp His Glu Arg Pro Ser Val Tyr
    290                 295                 300
Ala Phe Tyr Ser Glu Gln Pro Asp Phe Ser Gly His Lys Tyr Gly Pro
305                 310                 315                 320
Phe Gly Pro Glu Met Thr Asn Pro Leu Arg Glu Ile Asp Lys Ile Val
                325                 330                 335
Gly Gln Leu Met Asp Gly Leu Lys Gln Leu Lys Leu His Arg Cys Val
            340                 345                 350
Asn Val Ile Phe Val Gly Asp His Gly Met Glu Asp Val Thr Cys Asp
        355                 360                 365
Arg Thr Glu Phe Leu Ser Asn Tyr Leu Thr Asn Val Asp Asp Ile Thr
    370                 375                 380
Leu Val Pro Gly Thr Leu Gly Arg Ile Arg Ser Lys Phe Ser Asn Asn
385                 390                 395                 400
Ala Lys Tyr Asp Pro Lys Ala Ile Ile Ala Asn Leu Thr Cys Lys Lys
                405                 410                 415
Pro Asp Gln His Phe Lys Pro Tyr Leu Lys Gln His Leu Pro Lys Arg
            420                 425                 430
Leu His Tyr Ala Asn Asn Arg Arg Ile Glu Asp Ile His Leu Leu Val
        435                 440                 445
Glu Arg Arg Trp His Val Ala Arg Lys Pro Leu Asp Val Tyr Lys Lys
    450                 455                 460
Pro Ser Gly Lys Cys Phe Phe Gln Gly Asp His Gly Phe Asp Asn Lys
465                 470                 475                 480
Val Asn Ser Met Gln Thr Val Phe Val Gly Tyr Gly Ser Thr Phe Lys
                485                 490                 495
Tyr Lys Thr Lys Val Pro Pro Phe Glu Asn Ile Glu Leu Tyr Asn Val
            500                 505                 510
Met Cys Asp Leu Leu Gly Leu Lys Pro Ala Pro Asn Asn Gly Thr His
        515                 520                 525
Gly Ser Leu Asn His Leu Leu Arg Thr Asn Thr Phe Arg Pro Thr Met
    530                 535                 540
Pro Glu Glu Val Thr Arg Pro Asn Tyr Pro Gly Ile Met Tyr Leu Gln
545                 550                 555                 560
Ser Asp Phe Asp Leu Gly Cys Thr Cys Asp Asp Lys Val Glu Pro Lys
                565                 570                 575
```

```
Asn Lys Leu Asp Glu Leu Asn Lys Arg Leu His Thr Lys Gly Ser Thr
            580                 585                 590

Glu Ala Glu Thr Arg Lys Phe Arg Gly Ser Arg Asn Glu Asn Lys Glu
        595                 600                 605

Asn Ile Asn Gly Asn Phe Glu Pro Arg Lys Glu Arg His Leu Leu Tyr
    610                 615                 620

Gly Arg Pro Ala Val Leu Tyr Arg Thr Arg Tyr Asp Ile Leu Tyr His
625                 630                 635                 640

Thr Asp Phe Glu Ser Gly Tyr Ser Glu Ile Phe Leu Met Pro Leu Trp
                645                 650                 655

Thr Ser Tyr Thr Val Ser Lys Gln Ala Glu Val Ser Ser Val Pro Asp
            660                 665                 670

His Leu Thr Ser Cys Val Arg Pro Asp Val Arg Val Ser Pro Ser Phe
        675                 680                 685

Ser Gln Asn Cys Leu Ala Tyr Lys Asn Asp Lys Gln Met Ser Tyr Gly
    690                 695                 700

Phe Leu Phe Pro Pro Tyr Leu Ser Ser Pro Glu Ala Lys Tyr Asp
705                 710                 715                 720

Ala Phe Leu Val Thr Asn Met Val Pro Met Tyr Pro Ala Phe Lys Arg
                725                 730                 735

Val Trp Asn Tyr Phe Gln Arg Val Leu Val Lys Lys Tyr Ala Ser Glu
            740                 745                 750

Arg Asn Gly Val Asn Val Ile Ser Gly Pro Ile Phe Asp Tyr Asp Tyr
        755                 760                 765

Asp Gly Leu His Asp Thr Glu Asp Lys Ile Lys Gln Tyr Val Glu Gly
    770                 775                 780

Ser Ser Ile Pro Val Pro Thr His Tyr Tyr Ser Ile Ile Thr Ser Cys
785                 790                 795                 800

Leu Asp Phe Thr Gln Pro Ala Asp Lys Cys Asp Gly Pro Leu Ser Val
                805                 810                 815

Ser Ser Phe Ile Leu Pro His Arg Pro Asp Asn Glu Glu Ser Cys Asn
            820                 825                 830

Ser Ser Glu Asp Glu Ser Lys Trp Val Glu Glu Leu Met Lys Met His
        835                 840                 845

Thr Ala Arg Val Arg Asp Ile Glu His Leu Thr Ser Leu Asp Phe Phe
    850                 855                 860

Arg Lys Thr Ser Arg Ser Tyr Pro Glu Ile Leu Thr Leu Lys Thr Tyr
865                 870                 875                 880

Leu His Thr Tyr Glu Ser Glu Ile
                885

<210> SEQ ID NO 3
<211> LENGTH: 227
<212> TYPE: PRT
<213> ORGANISM: Homo sapiens

<400> SEQUENCE: 3

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60
```

His Asn Ala Lys Thr Lys Pro Arg Glu Glu Gln Tyr Asn Ser Thr Tyr
 65                  70                  75                  80

Arg Val Val Ser Val Leu Thr Val Leu His Gln Asp Trp Leu Asn Gly
                 85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225

<210> SEQ ID NO 4
<211> LENGTH: 24
<212> TYPE: PRT
<213> ORGANISM: Artificial Sequence
<220> FEATURE:
<223> OTHER INFORMATION: Chemically synthesized
<220> FEATURE:
<221> NAME/KEY: MOD_RES
<222> LOCATION: (23)..(23)
<223> OTHER INFORMATION: Xaa23 is absent or L
<220> FEATURE:
<221> NAME/KEY: MOD_RES
<222> LOCATION: (24)..(24)
<223> OTHER INFORMATION: Xaa24 is absent if Xaa23 is absent, and Xaa24
      is absent or Q if Xaa23 is L

<400> SEQUENCE: 4

Met Thr Ser Lys Phe Leu Leu Val Ser Phe Ile Leu Ala Ala Leu Ser
1               5                   10                  15

Leu Ser Thr Thr Phe Ser Xaa Xaa
            20

<210> SEQ ID NO 5
<211> LENGTH: 22
<212> TYPE: PRT
<213> ORGANISM: Artificial Sequence
<220> FEATURE:
<223> OTHER INFORMATION: Chemically synthesized

<400> SEQUENCE: 5

Met Arg Gly Pro Ala Val Leu Leu Thr Val Ala Leu Ala Thr Leu Leu
1               5                   10                  15

Ala Pro Gly Ala Gly Ala
            20

<210> SEQ ID NO 6
<211> LENGTH: 20
<212> TYPE: PRT

```
<213> ORGANISM: Artificial Sequence
<220> FEATURE:
<223> OTHER INFORMATION: Chemically synthesized

<400> SEQUENCE: 6

Met Arg Gly Pro Ala Val Leu Leu Thr Val Ala Leu Ala Thr Leu Leu
1               5                   10                  15

Ala Pro Gly Ala
            20

<210> SEQ ID NO 7
<211> LENGTH: 1078
<212> TYPE: PRT
<213> ORGANISM: Artificial Sequence
<220> FEATURE:
<223> OTHER INFORMATION: ENPP1-Fc

<400> SEQUENCE: 7

Met Arg Gly Pro Ala Val Leu Leu Thr Val Ala Leu Ala Thr Leu Leu
1               5                   10                  15

Ala Pro Gly Ala Gly Ala Pro Ser Cys Ala Lys Glu Val Lys Ser Cys
            20                  25                  30

Lys Gly Arg Cys Phe Glu Arg Thr Phe Gly Asn Cys Arg Cys Asp Ala
        35                  40                  45

Ala Cys Val Glu Leu Gly Asn Cys Cys Leu Asp Tyr Gln Glu Thr Cys
    50                  55                  60

Ile Glu Pro Glu His Ile Trp Thr Cys Asn Lys Phe Arg Cys Gly Glu
65                  70                  75                  80

Lys Arg Leu Thr Arg Ser Leu Cys Ala Cys Ser Asp Asp Cys Lys Asp
                85                  90                  95

Lys Gly Asp Cys Cys Ile Asn Tyr Ser Ser Val Cys Gln Gly Glu Lys
            100                 105                 110

Ser Trp Val Glu Glu Pro Cys Glu Ser Ile Asn Glu Pro Gln Cys Pro
        115                 120                 125

Ala Gly Phe Glu Thr Pro Pro Thr Leu Leu Phe Ser Leu Asp Gly Phe
    130                 135                 140

Arg Ala Glu Tyr Leu His Thr Trp Gly Gly Leu Leu Pro Val Ile Ser
145                 150                 155                 160

Lys Leu Lys Lys Cys Gly Thr Tyr Thr Lys Asn Met Arg Pro Val Tyr
                165                 170                 175

Pro Thr Lys Thr Phe Pro Asn His Tyr Ser Ile Val Thr Gly Leu Tyr
            180                 185                 190

Pro Glu Ser His Gly Ile Ile Asp Asn Lys Met Tyr Asp Pro Lys Met
        195                 200                 205

Asn Ala Ser Phe Ser Leu Lys Ser Lys Glu Lys Phe Asn Pro Glu Trp
    210                 215                 220

Tyr Lys Gly Glu Pro Ile Trp Val Thr Ala Lys Tyr Gln Gly Leu Lys
225                 230                 235                 240

Ser Gly Thr Phe Phe Trp Pro Gly Ser Asp Val Glu Ile Asn Gly Ile
                245                 250                 255

Phe Pro Asp Ile Tyr Lys Met Tyr Asn Gly Ser Val Pro Phe Glu Glu
            260                 265                 270

Arg Ile Leu Ala Val Leu Gln Trp Leu Gln Leu Pro Lys Asp Glu Arg
        275                 280                 285

Pro His Phe Tyr Thr Leu Tyr Leu Glu Glu Pro Asp Ser Ser Gly His
    290                 295                 300
```

-continued

```
Ser Tyr Gly Pro Val Ser Glu Val Ile Lys Ala Leu Gln Arg Val
305                 310                 315                 320

Asp Gly Met Val Gly Met Leu Met Asp Gly Leu Lys Glu Leu Asn Leu
            325                 330                 335

His Arg Cys Leu Asn Leu Ile Leu Ile Ser Asp His Gly Met Glu Gln
            340                 345                 350

Gly Ser Cys Lys Lys Tyr Ile Tyr Leu Asn Lys Tyr Leu Gly Asp Val
            355                 360                 365

Lys Asn Ile Lys Val Ile Tyr Gly Pro Ala Ala Arg Leu Arg Pro Ser
370                 375                 380

Asp Val Pro Asp Lys Tyr Tyr Ser Phe Asn Tyr Glu Gly Ile Ala Arg
385                 390                 395                 400

Asn Leu Ser Cys Arg Glu Pro Asn Gln His Phe Lys Pro Tyr Leu Lys
            405                 410                 415

His Phe Leu Pro Lys Arg Leu His Phe Ala Lys Ser Asp Arg Ile Glu
            420                 425                 430

Pro Leu Thr Phe Tyr Leu Asp Pro Gln Trp Gln Leu Ala Leu Asn Pro
            435                 440                 445

Ser Glu Arg Lys Tyr Cys Gly Ser Gly Phe His Gly Ser Asp Asn Val
450                 455                 460

Phe Ser Asn Met Gln Ala Leu Phe Val Gly Tyr Gly Pro Gly Phe Lys
465                 470                 475                 480

His Gly Ile Glu Ala Asp Thr Phe Glu Asn Ile Glu Val Tyr Asn Leu
            485                 490                 495

Met Cys Asp Leu Leu Asn Leu Thr Pro Ala Pro Asn Asn Gly Thr His
            500                 505                 510

Gly Ser Leu Asn His Leu Leu Lys Asn Pro Val Tyr Thr Pro Lys His
            515                 520                 525

Pro Lys Glu Val His Pro Leu Val Gln Cys Pro Phe Thr Arg Asn Pro
530                 535                 540

Arg Asp Asn Leu Gly Cys Ser Cys Asn Pro Ser Ile Leu Pro Ile Glu
545                 550                 555                 560

Asp Phe Gln Thr Gln Phe Asn Leu Thr Val Ala Glu Glu Lys Ile Ile
            565                 570                 575

Lys His Glu Thr Leu Pro Tyr Gly Arg Pro Arg Val Leu Gln Lys Glu
            580                 585                 590

Asn Thr Ile Cys Leu Leu Ser Gln His Gln Phe Met Ser Gly Tyr Ser
            595                 600                 605

Gln Asp Ile Leu Met Pro Leu Trp Thr Ser Tyr Thr Val Asp Arg Asn
610                 615                 620

Asp Ser Phe Ser Thr Glu Asp Phe Ser Asn Cys Leu Tyr Gln Asp Phe
625                 630                 635                 640

Arg Ile Pro Leu Ser Pro Val His Lys Cys Ser Phe Tyr Lys Asn Asn
            645                 650                 655

Thr Lys Val Ser Tyr Gly Phe Leu Ser Pro Pro Gln Leu Asn Lys Asn
            660                 665                 670

Ser Ser Gly Ile Tyr Ser Glu Ala Leu Leu Thr Thr Asn Ile Val Pro
            675                 680                 685

Met Tyr Gln Ser Phe Gln Val Ile Trp Arg Tyr Phe His Asp Thr Leu
            690                 695                 700

Leu Arg Lys Tyr Ala Glu Glu Arg Asn Gly Val Asn Val Val Ser Gly
705                 710                 715                 720
```

-continued

Pro Val Phe Asp Phe Asp Tyr Asp Gly Arg Cys Asp Ser Leu Glu Asn
            725                 730                 735

Leu Arg Gln Lys Arg Arg Val Ile Arg Asn Gln Glu Ile Leu Ile Pro
            740                 745                 750

Thr His Phe Ile Val Leu Thr Ser Cys Lys Asp Thr Ser Gln Thr
            755                 760                 765

Pro Leu His Cys Glu Asn Leu Asp Thr Leu Ala Phe Ile Leu Pro His
            770                 775                 780

Arg Thr Asp Asn Ser Glu Ser Cys Val His Gly Lys His Asp Ser Ser
785                 790                 795                 800

Trp Val Glu Glu Leu Leu Met Leu His Arg Ala Arg Ile Thr Asp Val
                805                 810                 815

Glu His Ile Thr Gly Leu Ser Phe Tyr Gln Gln Arg Lys Glu Pro Val
                820                 825                 830

Ser Asp Ile Leu Lys Leu Lys Thr His Leu Pro Thr Phe Ser Gln Glu
                835                 840                 845

Asp Arg Ser Asp Lys Thr His Thr Cys Pro Pro Cys Pro Ala Pro Glu
                850                 855                 860

Leu Leu Gly Gly Pro Ser Val Phe Leu Phe Pro Pro Lys Pro Lys Asp
865                 870                 875                 880

Thr Leu Met Ile Ser Arg Thr Pro Glu Val Thr Cys Val Val Val Asp
                885                 890                 895

Val Ser His Glu Asp Pro Glu Val Lys Phe Asn Trp Tyr Val Asp Gly
                900                 905                 910

Val Glu Val His Asn Ala Lys Thr Lys Pro Arg Glu Glu Gln Tyr Asn
                915                 920                 925

Ser Thr Tyr Arg Val Val Ser Val Leu Thr Val Leu His Gln Asp Trp
            930                 935                 940

Leu Asn Gly Lys Glu Tyr Lys Cys Lys Val Ser Asn Lys Ala Leu Pro
945                 950                 955                 960

Ala Pro Ile Glu Lys Thr Ile Ser Lys Ala Lys Gly Gln Pro Arg Glu
                965                 970                 975

Pro Gln Val Tyr Thr Leu Pro Pro Ser Arg Glu Glu Met Thr Lys Asn
                980                 985                 990

Gln Val Ser Leu Thr Cys Leu Val Lys Gly Phe Tyr Pro Ser Asp Ile
            995                 1000                1005

Ala Val Glu Trp Glu Ser Asn Gly Gln Pro Glu Asn Asn Tyr Lys
        1010                1015                1020

Thr Thr Pro Pro Val Leu Asp Ser Asp Gly Ser Phe Phe Leu Tyr
        1025                1030                1035

Ser Lys Leu Thr Val Asp Lys Ser Arg Trp Gln Gln Gly Asn Val
        1040                1045                1050

Phe Ser Cys Ser Val Met His Glu Ala Leu His Asn His Tyr Thr
        1055                1060                1065

Gln Lys Ser Leu Ser Leu Ser Pro Gly Lys
        1070                1075